US012622977B2

(12) United States Patent
Zhang et al.

(10) Patent No.: US 12,622,977 B2
(45) Date of Patent: May 12, 2026

(54) ANTIBODY DRUG CONJUGATE

(71) Applicants: CHIA TAI TIANQING PHARMACEUTICAL GROUP CO., LTD., Lianyungang City (CN); NANJING SHUNXIN PHARMACEUTICALS CO., LTD. OF CHIATAI TIANQING PHARMACEUTICAL GROUP, Nanjing City (CN)

(72) Inventors: Xiquan Zhang, Nanjing City (CN); Tianxi Chen, Nanjing City (CN); Weiwei Feng, Nanjing City (CN); Bing Zhang, Nanjing City (CN); Xiaoqi Tang, Nanjing City (CN); Tongjie Xu, Nanjing City (CN); Xiaojin Wang, Nanjing City (CN); Huace Sheng, Nanjing City (CN); Zhengping Zhang, Nanjing City (CN); Hua Wang, Lianyungang City (NA); Yong Gao, Nanjing City (CN)

(73) Assignees: Chia Tai Tianqing Pharmaceutical Group Co., Ltd., Lianyungang City (CN); Nanjing Shunxin Pharmaceuticals Co., Ltd. of Chitai Tianqing Pharmaceutical Group, Nanjing City (CN)

(*) Notice: Subject to any disclaimer, the term of this patent is extended or adjusted under 35 U.S.C. 154(b) by 561 days.

(21) Appl. No.: 18/040,498

(22) PCT Filed: Aug. 13, 2021

(86) PCT No.: PCT/CN2021/112462
§ 371 (c)(1),
(2) Date: Feb. 3, 2023

(87) PCT Pub. No.: WO2022/033578
PCT Pub. Date: Feb. 17, 2022

(65) Prior Publication Data

US 2023/0405141 A1 Dec. 21, 2023

(30) Foreign Application Priority Data

Aug. 13, 2020 (CN) ........................ 202010814877.X

(51) Int. Cl.

| | |
|---|---|
| ***A61K 47/68*** | (2017.01) |
| ***A61K 47/54*** | (2017.01) |
| ***A61K 47/65*** | (2017.01) |
| ***A61P 35/00*** | (2006.01) |

(52) U.S. Cl.
CPC ........ *A61K 47/6855* (2017.08); *A61K 47/545* (2017.08); *A61K 47/65* (2017.08); *A61K 47/6803* (2017.08); *A61P 35/00* (2018.01)

(58) Field of Classification Search
CPC .......... A61K 47/68037; A61K 47/6803; C07B 2200/05; C07B 59/00; C07B 59/001; C07B 59/002; C07B 59/008
See application file for complete search history.

(56) References Cited

U.S. PATENT DOCUMENTS

| | | | | |
|---|---|---|---|---|
| 7,960,516 | B2 * | 6/2011 | Matheus ............ | C07K 16/2863 530/387.3 |
| 8,840,896 | B2 | 9/2014 | Lowman | |
| 9,745,382 | B1 | 8/2017 | Li | |
| 9,849,191 | B2 | 12/2017 | Yurkovetskiy et al. | |
| 10,000,576 | B1 | 6/2018 | Weisser | |

(Continued)

FOREIGN PATENT DOCUMENTS

| | | | |
|---|---|---|---|
| CN | 103319599 | A | 9/2013 |
| CN | 104610453 | A | 5/2015 |

(Continued)

OTHER PUBLICATIONS

Ke et al, International Journal of Pharmaceutics, 2015, vol. 548, pp. 682-688 (Year: 2015).*

(Continued)

*Primary Examiner* — Karen A. Canella
(74) *Attorney, Agent, or Firm* — NIXON PEABODY LLP

(57) ABSTRACT

Provided is an antibody drug conjugate, specifically comprising a therapeutic antibody moiety, an intermediate linker moiety and a cytotoxic drug moiety which are linked. The therapeutic antibody moiety is an antibody against an HER2 target. The cytotoxic drug moiety is a camptothecin topoisomerase I inhibitor. The cytotoxic drug moiety or the linker-cytotoxic drug moiety is modified by means of deuterium substitution. The antibody drug conjugate can be used for the prevention or treatment of cancers.

VII

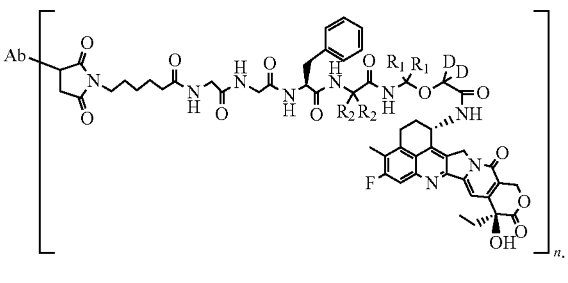

12 Claims, 5 Drawing Sheets

Specification includes a Sequence Listing.

(56) References Cited

U.S. PATENT DOCUMENTS

| | | | |
|---|---|---|---|
| 2016/0279259 | A1 | 9/2016 | Masuda |
| 2016/0289328 | A1 | 10/2016 | Ng |
| 2017/0029529 | A1 | 2/2017 | Croasdale |
| 2020/0093861 | A1 | 3/2020 | Klein |
| 2020/0385486 | A1 | 12/2020 | Naito |
| 2021/0347894 | A1 | 11/2021 | Ying |
| 2021/0353764 | A1 | 11/2021 | Xu |
| 2022/0143178 | A1 | 5/2022 | Wang |
| 2023/0405141 | A1 | 12/2023 | Zhang |

FOREIGN PATENT DOCUMENTS

| | | | | |
|---|---|---|---|---|
| CN | 104755494 | A | 7/2015 | |
| CN | 105829346 | A | 8/2016 | |
| CN | 105829347 | A | 8/2016 | |
| CN | 105940113 | A | 9/2016 | |
| CN | 109715671 | A | 5/2019 | |
| CN | 110461360 | A | 11/2019 | |
| JP | 2005522514 | A | 7/2005 | |
| JP | 2016535728 | A | 11/2016 | |
| WO | 2013168918 | A1 | 11/2013 | |
| WO | 2015077891 | A1 | 6/2015 | |
| WO | WO-2016077505 | A2 * | 5/2016 | ......... A61K 47/6803 |
| WO | 2018014864 | A1 | 1/2018 | |
| WO | WO 2019034176 | A1 | 2/2019 | |
| WO | 2020063676 | A1 | 4/2020 | |
| WO | WO 2020063673 | A1 | 4/2020 | |
| WO | 2020156555 | A1 | 8/2020 | |
| WO | 2022033578 | A1 | 2/2022 | |

OTHER PUBLICATIONS

Morissette et al (Advanced Drug Delivery Reviews, 2004, vol. 56, pp. 275-300) (Year: 2004).*

Lewis et al (Nature Biotechnology, 2014, vol. 32, pp. 191-198) (Year: 2014).*

Ahmad et al. "scFv Antibody: Principles and Clinical Application." Clinical and Developmental Immunology, vol. 2012, Jan. 1, 2012, doi:10.1155/2012/980250, (15 pages).

Pirali et al. "Applications of Deuterium in Medicinal Chemistry," Journal of Medicinal Chemistry , doi: 10.1021/acs.jmedchem.8b01808, 2019, (22 pages).

Shang et al., "Characterization of the Native and Denatured Herceptin by ELISA and QCM using a High-Affinity Single Chain Fragment Variable (scFv) Recombinant Antibody," NIH Public Access, Oct. 2, 2012, doi:10.1021/ac301235a, (17 pages).

Extended European Search Report in EP Application No. 21855628.0-1111, mailed Mar. 21, 2025, (14 pages).

International Search Report in International Patent Application No. PCT/CN2021/112462, mailed Nov. 3, 2021 (13 pages w/English translation).

International Written Opinion in International Patent Application No. PCT/CN2021/112462, mailed Nov. 3, 2021 (6 pages).

Li et al. "Antibody aggregation: insights from sequence and structure." Antibodies 5.3. dated 2016 (23 pages).

Ogitani et al. "DS-8201a, a novel HER2-targeting ADC with a novel DNA topoisomerase I inhibitor, demonstrates a promising antitumor efficacy with differentiation from T-DM1." Clinical Cancer Research 22.20, dated Mar. 29, 2016 (27 pages).

Syroeshkin et al. "The Influence of Deuterium on the Properties of Pharmaceutical Substances (Review)." Development and Registration of Medicinal Products vol. 9, No. 2, dated 2020 (pp. 24-32).

Safdari. "Engineering of single chain antibodies for solubility." International Immunopharmacology 55, dated 2018 (pp. 86-97).

Honegger et al. "The influence of the framework core residues on the biophysical properties of immunoglobulin heavy chain variable domains." Protein Engineering, Design & Selection 22.3, dated Jan. 10, 2009 (pp. 121-134).

* cited by examiner

ANTIBODY DRUG CONJUGATE

CROSS-REFERENCE TO RELATED APPLICATIONS

The present application is a U.S. National Stage Entry of International Application No. PCT/CN2021/112462 filed on Aug. 13, 2021, which claims the benefit of and priority to Chinese Patent Application No. 202010814877.X filed with China National Intellectual Property Administration on Aug. 13, 2020, which are incorporated herein by reference in their entireties.

SEQUENCE LISTING

The instant application contains a Sequence Listing that has been submitted in ASCII format via EFS-Web and is hereby incorporated by reference in its entirety. Said ASCII copy, created on Feb. 2, 2023, is named "059541-000099USPX_SL.txt" and is 89,398 bytes in size.

TECHNICAL FIELD

The present application relates to an antibody-drug conjugate comprising a therapeutic antibody moiety, an intermediate linker moiety and a cytotoxic drug moiety which are linked. The present application further relates to use of the antibody-drug conjugate in preparing a medicament for preventing and treating cancer.

BACKGROUND

Antibody-drug conjugates (ADCs) are a class of drugs that combine the high specificity of therapeutic antibodies and the high killing activity of cytotoxic drugs, where the therapeutic antibody moiety is linked to the cytotoxic drug moiety via an intermediate linker moiety. Currently, at least eight ADC drugs are marketed globally, among which antibody moieties of brentuximab vedotin, polatuzumab vedotin and enfortumab vedotin are directed against targets CD30, CD79b and Nectin-4, respectively; antibody moieties of trastuzumab emtansine and trastuzumab deruxtecan are directed against target HER2; antibody moieties of gemtuzumab ozogamicin and inotuzumab ozogamicin are directed against targets CD33 and CD22, respectively; antibody moiety of sacituzumab govitecan is directed against target TROP2. For the cytotoxic drug moieties, brentuximab vedotin, polatuzumab vedotin and enfortumab vedotin adopt auristatin toxin molecules acting on microtubules, trastuzumab emtansine adopts maytansinoid toxin molecules acting on microtubules, gemtuzumab ozogamicin and inotuzumab ozogamicin adopts calicheamicin toxin molecules acting on DNA, and the lastest marketed trastuzumab deruxtecan and sacituzumab govitecan adopt camptothecin analog toxin molecules. For the intermediate linker moiety, trastuzumab emtansine adopts a non-cleavable linker, while the remaining seven of the above ADC drugs adopt cleavable linkers.

Camptothecin (CPT) analogs and derivatives exert anti-tumor activity by binding to topoisomerase I, which exhibits significant activity against a wide variety of tumor types. To overcome the poor water solubility of CPT, researchers have synthesized a variety of CPT derivatives, of which irinotecan hydrochloride (CPT-11) is a water-soluble prodrug that has been approved for the treatment of metastatic colorectal cancer. However, CPT-11 must be catalyzed by carboxylesterase in vivo before it can be converted to its active form SN-38 (formula I), this conversion is extremely inefficient, and SN38 itself is difficult to be prepared as drugs due to its poor solubility. Exatecan (formula II), another water-soluble CPT derivative, had been attempted for development as an anti-tumor drug, however, the development had been ceased by 2004, and exatecant does not need to be activated by enzymes. In addition, compared with SN-38, which is the pharmacodynamic ontology of irinotecan, exatecan has a stronger inhibitory effect on the activity of topoisomerase I.

I

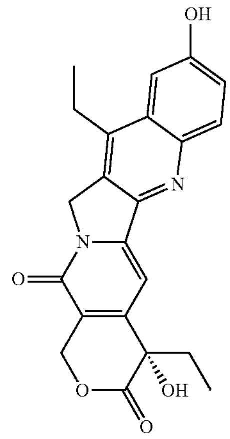

II

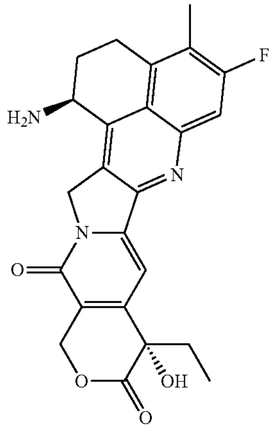

ADC drugs combine the dual advantages of high potency of cytotoxic small molecules and high selectivity of antibodies to specific tumor cells, however, there is still a need to develop highly potent and low-toxic ADC drugs that can target more indications.

BRIEF SUMMARY

In one aspect, the present application provides an antibody-drug conjugate containing a deuterated modification, or a pharmaceutically acceptable salt or a solvate thereof, and specifically relates to a deuterated modification of a linker or a cytotoxic drug moiety.

In one aspect, the present application provides an antibody-drug conjugate of general formula Ab-(L-U)n, or a pharmaceutically acceptable salt or a solvate thereof, wherein Ab represents an antibody moiety, L represents a linker moiety, U represents a cytotoxic drug moiety, and n is an integer or a decimal selected from the group consisting of 1 to 10.

In one aspect, the present application provides an antibody-drug conjugate of general formula Ab-(L-U)n, or a pharmaceutically acceptable salt or a solvate thereof, wherein Ab (an antibody moiety) can specifically bind to a tumor antigen (including a tumor specific antigen and a tumor-associated antigen), which can be selected from any tumor prevention or treatment target known in the art, for example, can be selected from the group consisting of HER2, EGFR, CD20, CD30, CD33, CD47, CD79b, VEGF, VEGFR, MET, RET, PD-1, PD-L1, and the like.

In some embodiments, the present application provides an antibody-drug conjugate of general formula Ab-(L-U)n, or a pharmaceutically acceptable salt or a solvate thereof, wherein Ab (an antibody moiety) may be modifiable, for example, comprises changes, additions or subtractions of one or more amino acids.

In some embodiments, the present application provides an antibody-drug conjugate of general formula Ab-(L-U)n, or a pharmaceutically acceptable salt or a solvate thereof, wherein the antibody moiety Ab is an antibody capable of specifically binding to HER2.

In some embodiments, the antibody moiety Ab of the antibody-drug conjugate of general formula Ab-(L-U)n, or the pharmaceutically acceptable salt or the solvate thereof provided herein, is trastuzumab having a sequence shown in Table S1 below.

TABLE S1

| Trastuzumab sequence | |
|---|---|
| Heavy chain variable region | EVQLVESGGG LVQPGGSLRL SCAASGFNIK DTYIHWVRQA PGKGLEWVAR IYPTNGYTRY ADSVKGRFTI SADTSKNTAY LQMNSLRAED TAVYYCSRWG GDGFYAMDYW GQGTLVTVSS (SEQ ID NO: 40) |
| Heavy chain CDR1 | GFNIKDTYIH (SEQ ID NO: 44) |
| Heavy chain CDR2 | RIYPTNGYTRYADSVKG (SEQ ID NO: 28) |
| Heavy chain CDR3 | WGGDGFYAMDYW (SEQ ID NO: 29) |
| Light chain variable region | DIQMTQSPSS LSASVGDRVT ITCRASQDVN TAVAWYQQKP GKAPKLLIYS ASFLYSGVPS RFSGSRSGTD FTLTISSLQP EDFATYYCQQ HYTTPPTFGQ GTKVEIK (SEQ ID NO: 39) |
| Light chain CDR1 | CRASQDVNTAVAW (SEQ ID NO: 30) |
| Light chain CDR2 | SASFLYS (SEQ ID NO: 33) |
| Light chain CDR3 | QQHYTTPPT (SEQ ID NO: 32) |

In some embodiments, the antibody moiety Ab of the antibody-drug conjugate of general formula Ab-(L-U)n provided herein, or the pharmaceutically acceptable salt or the solvate thereof, is pertuzumab having a sequence shown in Table S2 below.

TABLE S2

| Pertuzumab sequence | |
|---|---|
| Heavy chain variable region | EVQLVESGGG LVQPGGSLRL SCAASGFTFT DYTMDWVRQA PGKGLEWVAD VNPNSGGSIY NQRFKGRFTL SVDRSKNTLY LQMNSLRAED TAVYYCARNL GPSFYFDYWG QGTLVTVSS (SEQ ID NO: 37) |
| Heavy chain CDR1 | GFTFTDYTMD (SEQ ID NO: 45) |
| Heavy chain CDR2 | DVNPNSGGSIYNQRFKG (SEQ ID NO: 46) |
| Heavy chain CDR3 | NLGPSFYFDY (SEQ ID NO: 47) |
| Light chain variable region | DIQMTQSPSS LSASVGDRVT ITCKASQDVS IGVAWYQQKP GKAPKLLIYS ASYRYTGVPS RFSGSGSGTD FTLTISSLQP EDFATYYCQQ YYIYPYTFGQ GTKVEIK (SEQ ID NO: 38) |
| Light chain CDR1 | KASQDVSIGVA (SEQ ID NO: 48) |
| Light chain CDR2 | SASYRYT (SEQ ID NO: 49) |
| Light chain CDR3 | QQYYIYPYT (SEQ ID NO: 50) |

In some embodiments, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv comprising a VH and a VL, the VH having a K30 mutation, and/or the VL having an F53 mutation. In some embodiments, the amino acid at position 30 in the sequence of VH is mutated from K to an acidic amino acid, e.g., E. In some embodiments, the amino acid at position 53 in the sequence of VL is mutated from F to a neutral or basic amino acid, e.g., Y, A, or R. For example, the scFv may comprise or be a sequence having a K30 mutation and/or a F53 mutation in the amino acid sequence set forth in SEQ ID NO: 1. In one aspect, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 27, 28 and 29, respectively, and the light chain CDR1, the light chain CDR2 and the light chain CDR3 comprising amino acid sequences set forth in SEQ ID NOs: 30, 34 and 32, respectively; wherein the sequence set forth in SEQ ID NO: 27 is GFNI$X_2$ DTYIH, where $X_2$ is K or E; the sequence set forth in SEQ ID NO: 34 is SAS$X_1$LYS, where $X_1$ is F or Y.

In one aspect, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 43, 28 and 29, respectively, and the light chain CDR1, the light chain CDR2 and the light chain CDR3 comprising amino acid sequences set forth in SEQ ID NOs: 30, 31 and 32, respectively.

In one aspect, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv and is selected from the group consisting of:

i. the first antigen-binding fragment comprising a heavy chain variable region and a light chain variable region which comprise amino acid sequences set forth in SEQ ID NOs: 41 and 42, respectively; and ii. the first antigen-binding fragment comprising a heavy chain variable region and a light chain variable region which comprise amino acid sequences having at least 80% identity to the amino acid sequences set forth in SEQ ID NOs: 41 and 42, respectively;

wherein the sequence set forth in SEQ ID NO: 41 is:

EVQLVESGGGLVQPGGSLRLSCAASGFNI$X_2$DTYIHWVRQAPGKGLEW

VARIYPTNGYTRYADSVKGRFTISADTSKNTAYLQMNSLRAEDTAVYY

CSRWGGDGFYAMDYWGQGTLVTVSS, where $X_2$ is K or E;

the sequence set forth in SEQ ID NO: 42 is:

DIQMTQSPSSLSASVGDRVTITCRASQDVNTAVAWYQQKPGKAPKLLI

YSAS$X_1$LYSGVPSRFSGSRSGTDFTLTISSLQPEDFATYYCQQHYTTP

PTFGQGTKVEIK, where $X_1$ is F or Y.

In one aspect, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv and comprises a heavy chain variable region and a light chain variable region comprising amino acid sequences set forth in SEQ ID NOs: 35 and 36, respectively.

In one aspect, the present application provides an antibody-drug conjugate of general formula Ab-(L-U)n, or a pharmaceutically acceptable salt or a solvate thereof, wherein the antibody moiety Ab comprises a first antigen-binding fragment that is monovalent and specifically binds to an ECD4 epitope of HER2 on an HER2-expressing cell, wherein the first antigen-binding fragment is an scFv, and a VH and VL of the first antigen-binding fragment is arranged from N-terminus to C-terminus in the following order: VH-linker-VL.

In one aspect, the present application provides an antibody-drug conjugate of general formula Ab-(L-U)n, or a pharmaceutically acceptable salt or a solvate thereof, wherein the antibody moiety Ab further comprises a second antigen-binding fragment that is monovalent and specifically binds to an ECD2 epitope of HER2 on an HER2-expressing cell, the second antigen-binding fragment being an Fab.

In one aspect, the present application provides an antibody-drug conjugate of general formula Ab-(L-U)n, or a pharmaceutically acceptable salt or a solvate thereof, wherein the antibody moiety Ab further comprises a second antigen-binding fragment that is monovalent and specifically binds to an ECD2 epitope of HER2 on an HER2-expressing cell, wherein the second antigen-binding fragment is an Fab and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 45, 46 and 47, respectively, and the light chain CDR1, the light chain CDR2 and the light chain CDR3 comprising amino acid sequences set forth in SEQ ID NOs: 48, 49 and 50, respectively.

In one aspect, the present application provides an antibody-drug conjugate of general formula Ab-(L-U)n, or a pharmaceutically acceptable salt or a solvate thereof, wherein the antibody moiety Ab further comprises a second antigen-binding fragment that is monovalent and specifically binds to an ECD2 epitope of HER2 on an HER2-expressing cell, wherein the second antigen-binding fragment is an scFv, and comprises a heavy chain variable region and a light chain variable region comprising amino acid sequences set forth in SEQ ID NOs: 37 and 38, respectively.

In some specific embodiments, the antibody moiety Ab of the antibody-drug conjugate of general formula Ab-(L-U)n, or the pharmaceutically acceptable salt or the solvate thereof provided herein, is shown in Table S3.

TABLE S3

Antibody moiety of exemplary antibody-drug conjugate, or pharmaceutically acceptable salt or solvate thereof

| Name | Description | First antigen-binding fragment (According to the Kabat numbering system) | Second antigen-binding fragment |
|---|---|---|---|
| / | Epitope-containing domain | ECD4 | ECD2 |
| | Form | scFV | Fab |
| | Original sequence | Trastuzumab | Pertuzumab |
| 1 | Sequence substitution | VL: F53Y | / |
| 2 | Sequence substitution | VH: K30E | / |
| 3 | Sequence substitution | VL: F53Y<br>VH: K30E | / |

In one aspect, the present application provides an antibody-drug conjugate of general formula Ab-(L-U)n, or a pharmaceutically acceptable salt or a solvate thereof, wherein the antibody moiety Ab comprises an immunoglobulin functional domain operably linked to a first antigen-binding fragment and/or a second antigen-binding fragment, the immunoglobulin functional domain comprising: i. one or more of CL, CH1, CH2 or CH3, or ii. an Fc.

In one aspect, the present application provides an antibody-drug conjugate of general formula Ab-(L-U)n, or a pharmaceutically acceptable salt or a solvate thereof, wherein the antibody moiety Ab comprises an immunoglobulin functional domain operably linked to a first antigen-binding fragment and/or a second antigen-binding fragment, the immunoglobulin functional domain comprising: i. one or more of CL, CH1, CH2 or CH3, or ii. an Fc, wherein the CL, CH1, CH2, CH3 and Fc are derived from CL, CH1, CH2, CH3 and Fc of human IgG, respectively.

In one aspect, the present application provides an antibody-drug conjugate of general formula Ab-(L-U)n, or a pharmaceutically acceptable salt or a solvate thereof, wherein the antibody moiety Ab comprises an immunoglobulin functional domain operably linked to a first antigen-binding fragment and/or a second antigen-binding fragment, the immunoglobulin functional domain comprising: i. one or more of CL, CH1, CH2 or CH3, or ii. an Fc, wherein the CL, CH1, CH2, CH3 or Fc has a modification or does not have a modification; preferably, the CH3 or Fc has a modification that is, e.g., an amino acid substitution at position 435 or/and position 436 according to the Kabat numbering system.

In one aspect, the present application provides an antibody-drug conjugate of general formula Ab-(L-U)n, or a pharmaceutically acceptable salt or a solvate thereof, wherein the antibody moiety Ab comprises an immunoglobulin functional domain operably linked to a first antigen-binding fragment and/or a second antigen-binding fragment, the immunoglobulin functional domain comprising: i. one or more of CL, CH1, CH2 or CH3, or ii. an Fc, wherein the Fc is a dimeric Fc comprising a first Fc polypeptide and a second Fc polypeptide, the first antigen-binding fragment is operably linked to the first Fc polypeptide, and the second antigen-binding fragment is operably linked to the second Fc polypeptide.

In one aspect, the present application provides an antibody-drug conjugate of general formula Ab-(L-U)n, or a pharmaceutically acceptable salt or a solvate thereof, wherein the antibody moiety Ab comprises a constant region operably linked to a first antigen-binding fragment and/or a second antigen-binding fragment, wherein the constant region may be a native sequence constant region or a mutated constant region of an immunoglobulin, e.g., one or more of native or mutated CL, CH1, CH2 and/or CH3 functional domains; in some examples, these functional domains are operably linked in a conventional manner in the art, the constant region may be derived from a constant region of a human immunoglobulin, such as from IgG1, IgG2, IgG3 or IgG4, and in some examples, the constant region may have modifications to improve its ability to mediate effector functions.

In one aspect, the present application provides an antibody-drug conjugate of general formula Ab-(L-U)n, or a pharmaceutically acceptable salt or a solvate thereof, wherein the antibody moiety Ab comprises an immunoglobulin functional domain or skeleton, e.g., an Fc, operably linked to a first antigen-binding fragment or/and a second antigen-binding fragment; the term Fc includes native sequence Fc regions and variant Fc regions, the Fc may be a human Fc, for example, it is derived from IgG1, IgG2, IgG3 or IgG4, and the Fc may have a modification so that its ability to mediate effector functions is improved. For example, in some embodiments, the skeleton has modifications, such as knob into hole, H435R, Y436F, defucosylation and the like; in some embodiments, the mutation sites of knob into hole in above skeleton include such as Y349C, T366S, L368A, Y407V, S354C, T366W and the like.

In one aspect, the present application provides an antibody-drug conjugate of general formula Ab-(L-U)n, or a pharmaceutically acceptable salt or a solvate thereof, wherein the antibody moiety Ab comprises a skeleton operably linked to a first antigen-binding fragment and/or a second antigen-binding fragment. In some embodiments, the skeleton described herein is a dimeric Fc comprising a first Fc polypeptide and a second Fc polypeptide. In some embodiments, the dimeric Fc described herein has a modification. In some embodiments, the dimeric Fc has an H435R modification or/and a Y436F modification, which may occur in one or both of polypeptide chain of the first Fc polypeptide and the second Fc polypeptide. In some specific embodiments, the dimeric Fc has an H435R modification or/and a Y436F modification, which only occur in one Fc polypeptide rather than in the other Fc polypeptide. In some embodiments, the dimeric Fc has mutation sites of knob-into-hole, such as Y349C, T366S, L368A, Y407V, S354C, T366W and the like. In some embodiments, one chain of the dimeric Fc has T366W or/and S354C, and the other chain has Y407V, Y349C, T366S or/and L368A.

In one aspect, the present application provides an antibody-drug conjugate of general formula Ab-(L-U)n, or a pharmaceutically acceptable salt or a solvate thereof, wherein the antibody moiety Ab is a bivalent bispecific antibody comprising: a heavy chain comprising SEQ ID NO: 11, a heavy chain comprising SEQ ID NO: 13, and a light chain comprising SEQ ID NO: 15.

In some specific embodiments, the antibody moiety Ab of the antibody-drug conjugate of general formula Ab-(L-U)n, or the pharmaceutically acceptable salt or the solvate thereof provided herein, is shown in Table S4.

TABLE S4

Antibody moiety of exemplary antibody-drug conjugate, or pharmaceutically acceptable salt or solvate thereof

| Name | | Description | Amino acid sequence |
|---|---|---|---|
| Expi Her2-2/ 23C-HER2-2 | First antigen-binding fragment (scFV) | Heavy chain CDR1 | GFNIEDTYIH (SEQ ID NO: 43) |
| | | Heavy chain CDR2 | RIYPTNGYTRYADSVKG (SEQ ID NO: 28) |
| | | Heavy chain CDR3 | WGGDGFYAMDYW (SEQ ID NO: 29) |
| | | Heavy chain variable region | EVQLVESGGGLVQPGGSLRLSCAASGFNIEDTYIHWVRQAPGK GLEWVARIYPTNGYTRYADSVKGRFTISADTSKNTAYLQMNSL RAEDTAVYYCSRWGGDGFYAMDYWGQGTLVTVSS (SEQ ID NO: 35) |
| | | Light chain CDR1 | CRASQDVNTAVAW (SEQ ID NO: 30) |
| | | Light chain CDR2 | SASYLYS (SEQ ID NO: 31) |
| | | Light chain | QQHYTTPPT |

TABLE S4-continued

Antibody moiety of exemplary antibody-drug conjugate, or pharmaceutically acceptable salt or solvate thereof

| Name | | Description | Amino acid sequence |
|---|---|---|---|
| | | CDR3 | (SEQ ID NO: 32) |
| | | Light chain variable region | DIQMTQSPSSLSASVGDRVTITCRASQDVNTAVAWYQQKPGKAPKLLIYSASYLYSGVPSRFSGSRSGTDFTLTISSLQPEDFATYYCQQHYTTPPTFGQGTKVEIK (SEQ ID NO: 36) |
| | anti-Her2-scFv-VH-K30E-VL-F53Y-Fc | | EVQLVESGGGLVQPGGSLRLSCAASGFNIEDTYIHWVRQAPGKGLEWVARIYPTNGYTRYADSVKGRFTISADTSKNTAYLQMNSLRAEDTAVYYCSRWGGDGFYAMDYWGQGTLVTVSSGGGGSGGGGSGGGGSGGGGSDIQMTQSPSSLSASVGDRVTITCRASQDVNTAVAWYQQKPGKAPKLLIYSASYLYSGVPSRFSGSRSGTDFTLTISSLQPEDFATYYCQQHYTTPPTFGQGTKVEIKGEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 11) |
| | Second antigen-binding fragment (Fab) | Heavy chain variable region | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSS (SEQ ID NO: 37) |
| | | Light chain variable region | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGQGTKVEIK (SEQ ID NO: 38) |
| | anti-Her2-domain2-HC-Fc | | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPGK (SEQ ID NO: 13) |
| | anti-Her2-domain2-LC | | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 15) |
| Expi Her2-3/23C-HER2-3 | First antigen-binding fragment (scFV) | Heavy chain CDR1 | GFNIEDTYIH (SEQ ID NO: 43) |
| | | Heavy chain CDR2 | RIYPTNGYTRYADSVKG (SEQ ID NO: 28) |
| | | Heavy chain CDR3 | WGGDGFYAMDYW (SEQ ID NO: 29) |
| | | Heavy chain variable region | EVQLVESGGGLVQPGGSLRLSCAASGFNIEDTYIHWVRQAPGKGLEWVARIYPTNGYTRYADSVKGRFTISADTSKNTAYLQMNSLRAEDTAVYYCSRWGGDGFYAMDYWGQGTLVTVSS (SEQ ID NO: 35) |
| | | Light chain CDR1 | CRASQDVNTAVAW (SEQ ID NO: 30) |
| | | Light chain CDR2 | SASFLYS (SEQ ID NO: 33) |
| | | Light chain CDR3 | QQHYTTPPT (SEQ ID NO: 32) |
| | | Light chain variable region | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK (SEQ ID NO: 39) |
| | Second antigen-binding fragment (Fab) | Heavy chain variable region | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSS (SEQ ID NO: 37) |
| | | Light chain variable region | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGQGTKVEIK (SEQ ID NO: 38) |

TABLE S4-continued

Antibody moiety of exemplary antibody-drug conjugate, or pharmaceutically acceptable salt or solvate thereof

| Name | | Description | Amino acid sequence |
|---|---|---|---|
| Expi Her2-4/ 23C-HER2-4 | First antigen-binding fragment (scFV) | Heavy chain CDR1 | GFNIKDTYIH (SEQ ID NO: 44) |
| | | Heavy chain CDR2 | RIYPTNGYTRYADSVKG (SEQ ID NO: 28) |
| | | Heavy chain CDR3 | WGGDGFYAMDYW (SEQ ID NO: 29) |
| | | Heavy chain variable region | EVQLVESGGGLVQPGGSLRLSCAASGFNIKDTYIHWVRQAPGK GLEWVARIYPTNGYTRYADSVKGRFTISADTSKNTAYLQMNSL RAEDTAVYYCSRWGGDGFYAMDYWGQGTLVTVSS (SEQ ID NO: 40) |
| | | Light chain CDR1 | CRASQDVNTAVAW (SEQ ID NO: 30) |
| | | Light chain CDR2 | SASYLYS (SEQ ID NO: 31) |
| | | Light chain CDR3 | QQHYTTPPT (SEQ ID NO: 32) |
| | | Light chain variable region | DIQMTQSPSSLSASVGDRVTITCRASQDVNTAVAWYQQKPGKA PKLLIYSASYLYSGVPSRFSGSRSGTDFTLTISSLQPEDFATY YCQQHYTTPPTFGQGTKVEIK (SEQ ID NO: 36) |
| | Second antigen-binding fragment (Fab) | Heavy chain variable region | EVQLVESGGGLVQPGGSLRLSCAASGFTFTDYTMDWVRQAPGK GLEWVADVNPNSGGSIYNQRFKGRFTLSVDRSKNTLYLQMNSL RAEDTAVYYCARNLGPSFYFDYWGQGTLVTVSS (SEQ ID NO: 37) |
| | | Light chain variable region | DIQMTQSPSSLSASVGDRVTITCKASQDVSIGVAWYQQKPGKA PKLLIYSASYRYTGVPSRFSGSGSGTDFTLTISSLQPEDFATY YCQQYYIYPYTFGQGTKVEIK (SEQ ID NO: 38) |

In one aspect, the present application provides an antibody-drug conjugate of general formula Ab-(L-U)n, or a pharmaceutically acceptable salt or a solvate thereof, wherein the cytotoxic drug moiety U is conjugated to the antibody moiety Ab via a linker moiety L. The linker moiety L disclosed herein may be linked to the antibody moiety by any method known in the art, preferably the linker moiety is linked to the antibody moiety via a sulfydryl group and/or amino group. In some more preferred embodiments, the linker moiety disclosed herein is linked to the antibody moiety via a sulfydryl group.

In one aspect, the present application provides an antibody-drug conjugate of general formula Ab-(L-U)n, or a pharmaceutically acceptable salt or a solvate thereof, wherein the cytotoxic drug moiety U is conjugated to the antibody moiety Ab via a linker moiety L, which may be a cleavable linker or a non-cleavable linker; in some embodiments, the linker moiety disclosed herein is a cleavable linker, which may be of, e.g., a low pH-dependent degradation type (including a hydrazone bond, a carbonate bond, and the like), a proteolytic type (including a peptide-based bond), a high glutathione concentration-dependent degradation type (including a disulfide bond), or the like; in other embodiments, the linker moiety disclosed herein is a non-cleavable linker, for example, may be maleimidocaproyl, and the like.

In one aspect, the present application provides an antibody-drug conjugate of general formula Ab-(L-U)n, or a pharmaceutically acceptable salt or a solvate thereof, wherein the antibody moiety Ab is conjugated to one or more cytotoxic drug moieties U, which may be selected from the group consisting of, e.g., alkaloids, antimetabolites, anti-tumor antibiotics, alkylating agents, platinum-based drugs, and the like, preferably the cytotoxic drug is a microtubule inhibitor (including maytansinoid, auristatin) or a DNA-acting cytotoxic drug (including calicheamicin, duocarmycin, PBD (pyrrolobenzodiazepine), a topoisomerase I inhibitor, and the like).

In some specific embodiments, the cytotoxic drug moiety U of the antibody-drug conjugate of general formula Ab-(L-U)n, or the pharmaceutically acceptable salt or the solvate thereof provided herein, is a topoisomerase I inhibitor.

In some specific embodiments, the cytotoxic drug moiety U of the antibody-drug conjugate of general formula Ab-(L-U)n, or the pharmaceutically acceptable salt or the solvate thereof provided herein, is a camptothecin analog topoisomerase I inhibitor.

In some preferred specific embodiments, the cytotoxic drug moiety U of the antibody-drug conjugate of general formula Ab-(L-U)n, or the pharmaceutically acceptable salt or the solvate thereof provided herein, is selected from the group consisting of SN-38, an SN-38 derivative, exatecan, and an exatecan derivative.

In some embodiments, the present application provides an antibody-drug conjugate of general formula Ab-(L-U)n, or a pharmaceutically acceptable salt or a solvate thereof, wherein Ab represents an antibody moiety, L represents a linker moiety, U represents a camptothecin topoisomerase I inhibitor, and n is an integer or a decimal selected from 1 to 10, wherein the L moiety and/or the U moiety has a deuterated modification. In some embodiments, n is an integer or a decimal selected from the group consisting of 2 to 10, e.g., 2 to 9, 2 to 8, 3 to 9, 3 to 8, 4 to 9, 4 to 8, 5 to 9, and 5 to 8.

In some embodiments, the present application provides an antibody-drug conjugate of general formula Ab-(L-U)n, or a pharmaceutically acceptable salt or a solvate thereof, wherein Ab represents an antibody moiety, L represents a linker moiety, U represents a camptothecin topoisomerase I inhibitor, and n is an integer or a decimal selected from the group consisting of 1 to 10, wherein the L moiety and/or the U moiety has a deuterated modification, and the cytotoxic drug moiety U is selected from the group consisting of SN-38, an SN-38 derivative, exatecan, and an exatecan derivative.

In some embodiments, the antibody-drug conjugate of general formula Ab-(L-U)n, or the pharmaceutically acceptable salt or the solvate thereof provided herein, comprises a structure of formula III below:

III

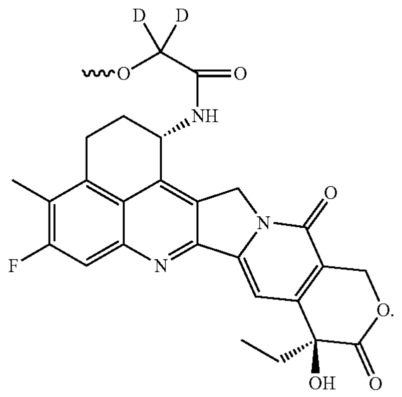

In some embodiments, the antibody-drug conjugate of general formula Ab-(L-U)n, or the pharmaceutically acceptable salt or the solvate thereof provided herein, comprises a structure of formula IV below:

IV

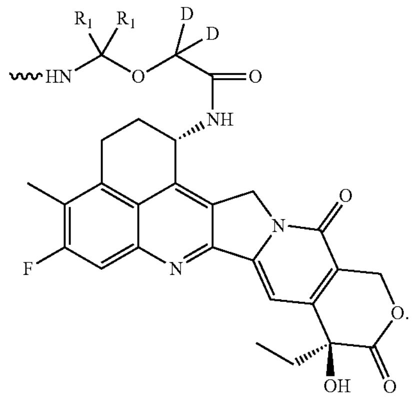

wherein $R_1$ is selected from the group consisting of hydrogen (H) and deuterium (D).

In some embodiments, the antibody-drug conjugate of general formula Ab-(L-U)n, or the pharmaceutically acceptable salt or the solvate thereof provided herein, comprises a structure of formula IV-1 or IV-2 below:

IV-1

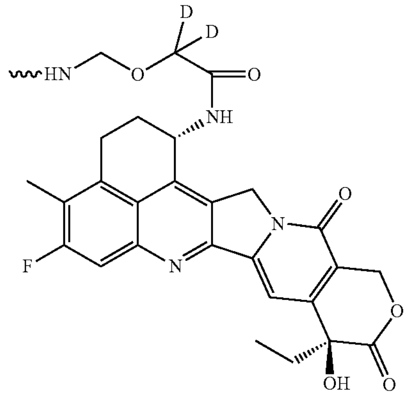

IV-2

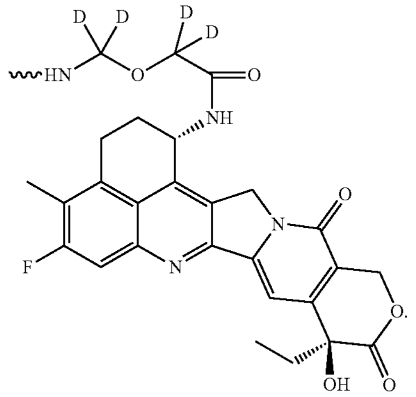

In some embodiments, the antibody-drug conjugate of general formula Ab-(L-U)n, or the pharmaceutically acceptable salt or the solvate thereof provided herein, comprises a structure of formula V below:

V

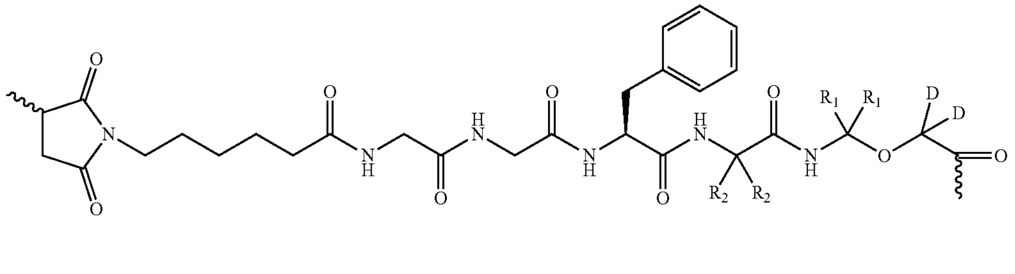

wherein $R_1$ and $R_2$ are each independently selected from the group consisting of hydrogen (H) and deuterium (D), and the left succinimide terminus of the structure is a site linking to the antibody moiety and the right carbonyl terminus is a site linking to the cytotoxic drug moiety.

In some embodiments, the antibody-drug conjugate of general formula Ab-(L-U)n, or the pharmaceutically acceptable salt or the solvate thereof provided herein, comprises a structure of formula V-1, V-2, V-3, or V-4 below, and the structures of formulas V-1 to V-4 are linked to the antibody moiety by the left succinimide terminus and the cytotoxic drug moiety by the right carbonyl terminus, respectively:

V-1

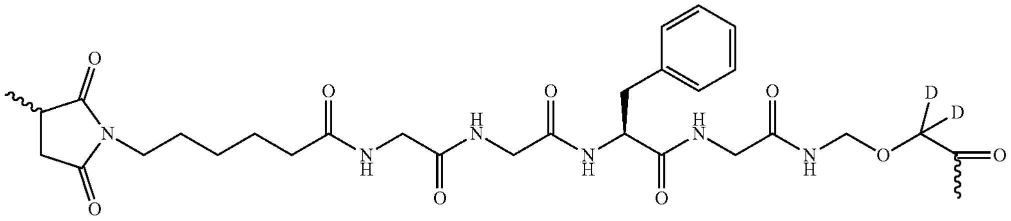

V-2

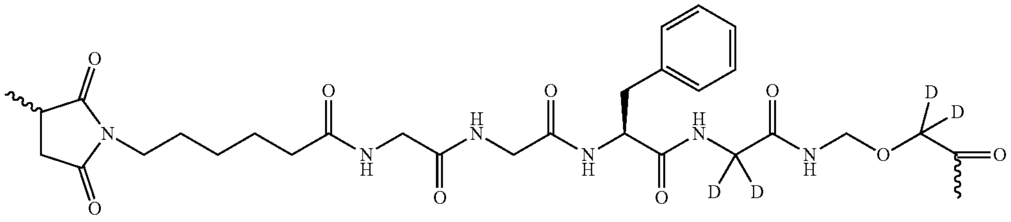

V-3

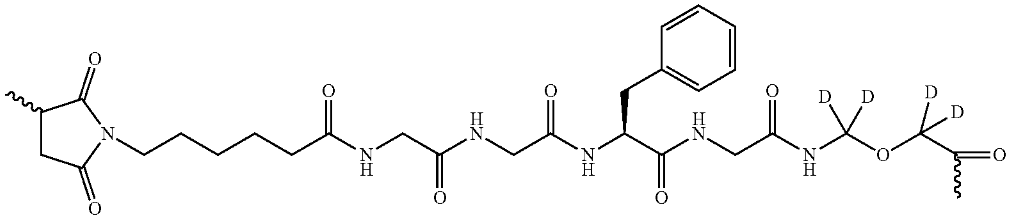

V-4

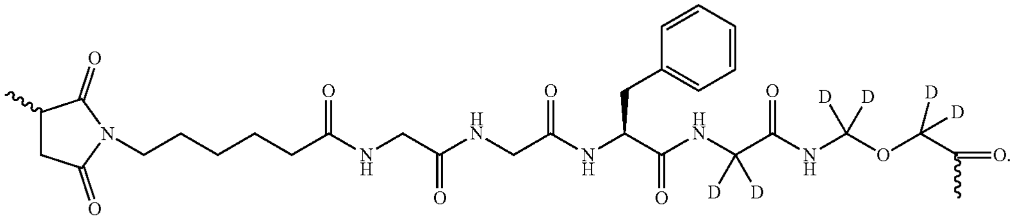

In some embodiments, the antibody-drug conjugate of general formula Ab-(L-U)n, or the pharmaceutically acceptable salt or the solvate thereof provided herein, comprises a structure of formula VI below:

VI

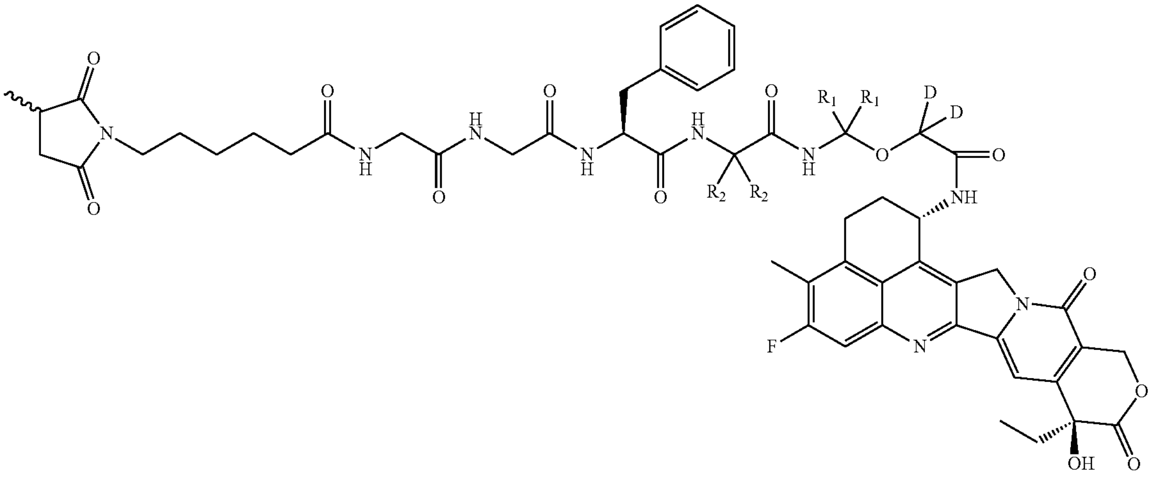

wherein, $R_1$ and $R_2$ are each independently selected from the group consisting of hydrogen (H) and deuterium (D).

In some embodiments, the antibody-drug conjugate of general formula Ab-(L-U)n, or the pharmaceutically acceptable salt or the solvate thereof provided herein, comprises a structure of formula VI-1, VI-2, VI-3, or VI-4 below:

VI-1

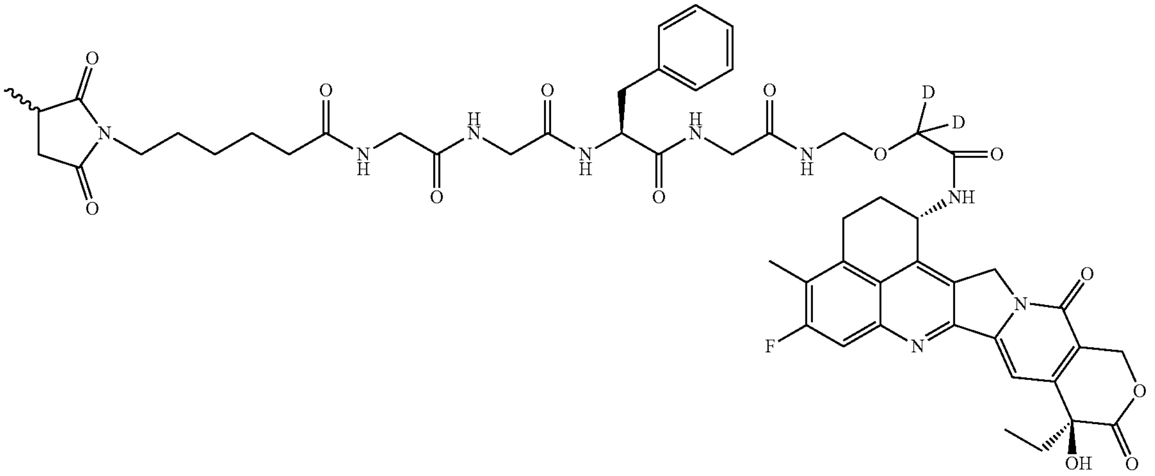

-continued
VI-2
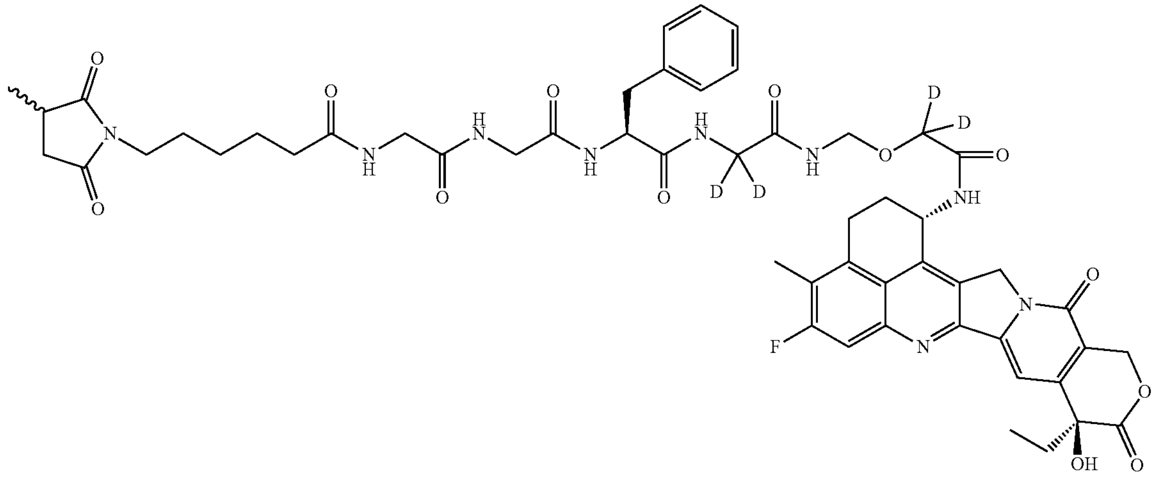
VI-3
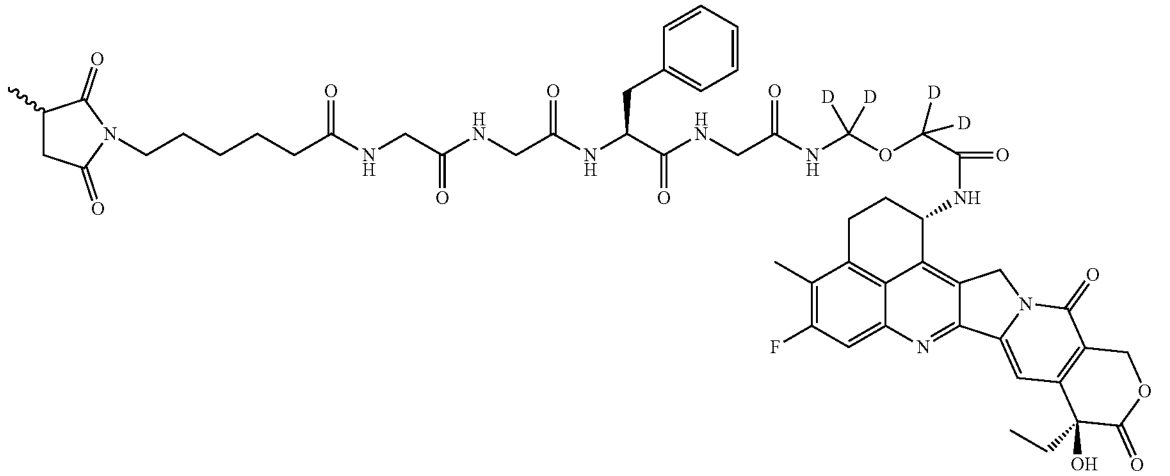
VI-4
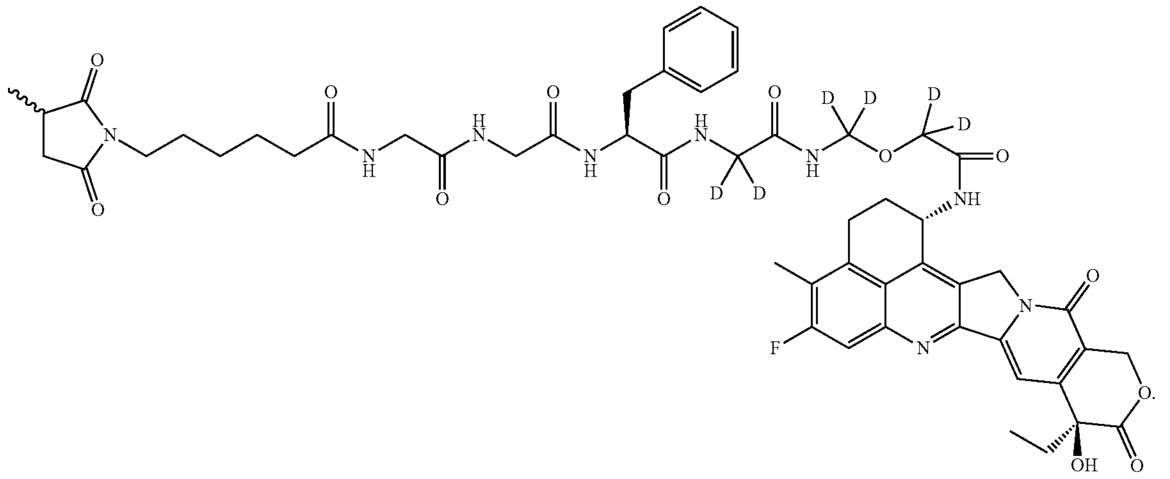

In some specific embodiments, the present application provides an antibody-drug conjugate, or a pharmaceutically acceptable salt or a solvate thereof, having a structure of formula VII:

VII

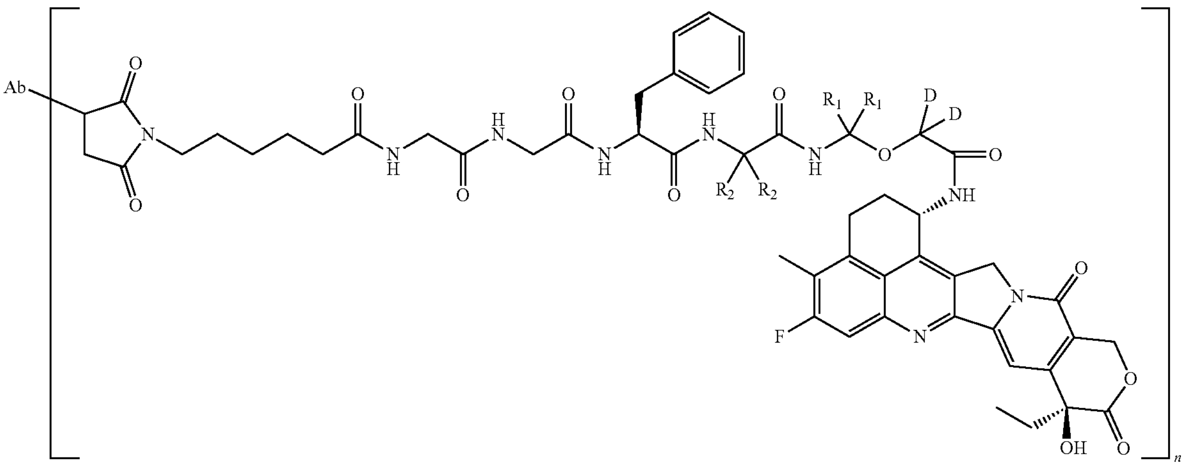

wherein,

Ab represents an antibody moiety comprising a first antigen-binding fragment and a second antigen-binding fragment, wherein the first antigen-binding fragment is an scFv, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 43, 28 and 29, respectively, and the light chain CDR1, the light chain CDR2 and the light chain CDR3 comprising amino acid sequences set forth in SEQ ID NOs: 30, 31 and 32, respectively;

the second antigen-binding fragment is an Fab, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 45, 46 and 47, respectively, and the light chain CDR1, the light chain CDR2 and the light chain CDR3 comprising amino acid sequences set forth in SEQ ID NOs: 48, 49 and 50, respectively;

n is an integer or a decimal selected from the group consisting of 1 to 10, and $R_1$ and $R_2$ are each independently selected from the group consisting of hydrogen (H) and deuterium (D).

In some specific embodiments, the present application provides an antibody-drug conjugate, or a pharmaceutically acceptable salt or a solvate thereof, having a structure of formula VII-1, VII-2, VII-3, or VII-4 below,

VII-1

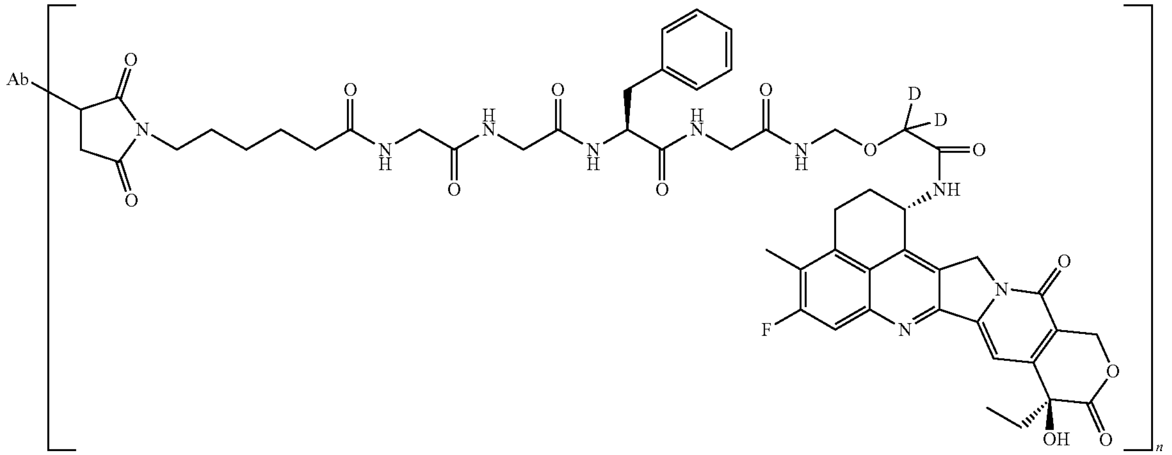

-continued
VII-2
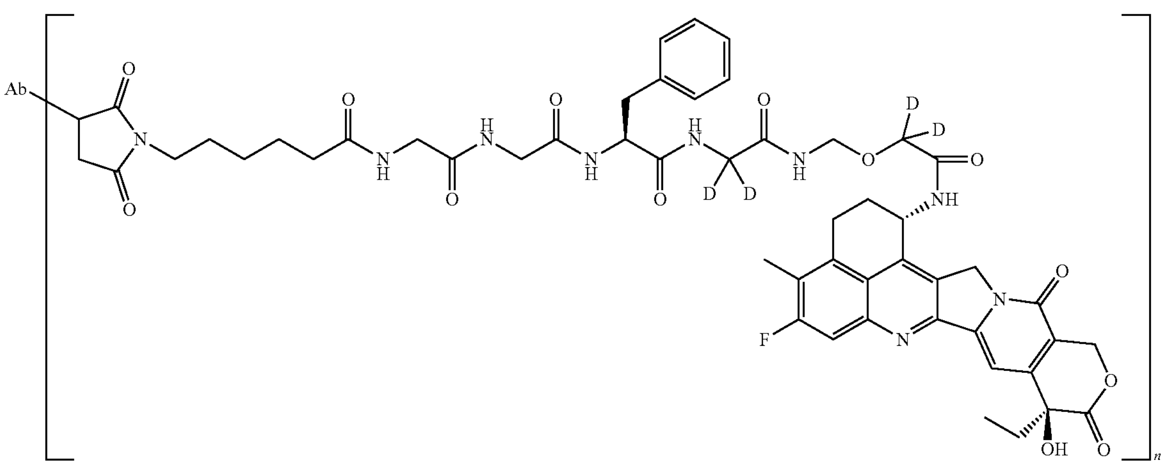
VII-3
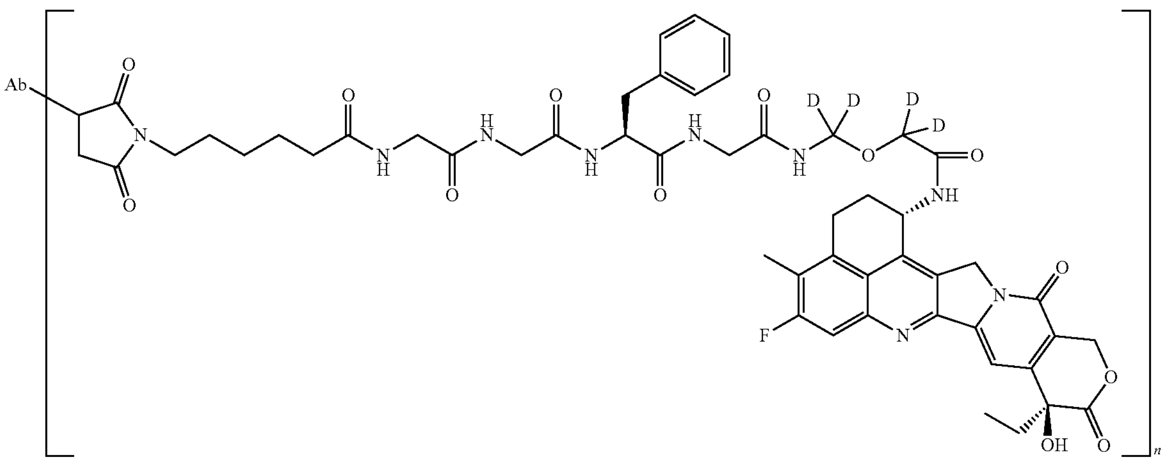
VII-4
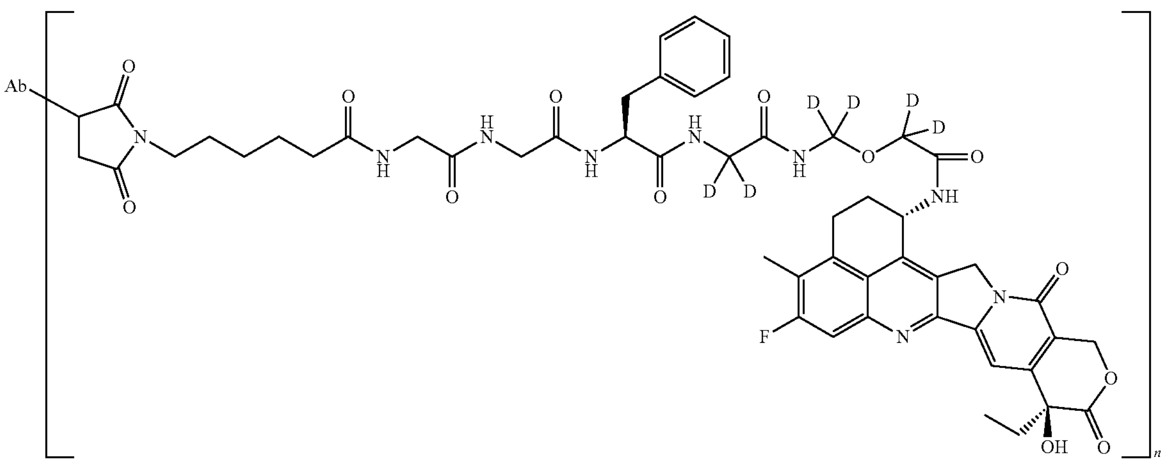

wherein,

Ab represents an antibody moiety comprising a first antigen-binding fragment and a second antigen-binding fragment, wherein the first antigen-binding fragment is an scFv, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 43, 28 and 29, respectively, and the light chain CDR1, the light chain CDR2 and the light chain CDR3 comprising amino acid sequences set forth in SEQ ID NOs: 30, 31 and 32, respectively;

the second antigen-binding fragment is an Fab, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 45, 46 and 47, respectively, and the light chain CDR1, the light chain CDR2 and the light chain CDR3 comprising amino acid sequences set forth in SEQ ID NOs: 48, 49 and 50, respectively;

n is an integer or a decimal selected from the group consisting of 1 to 10.

In one specific embodiment, the present application provides an antibody-drug conjugate, or a pharmaceutically acceptable salt or a solvate thereof, having a structure of formula VII-1 below,

VII-1

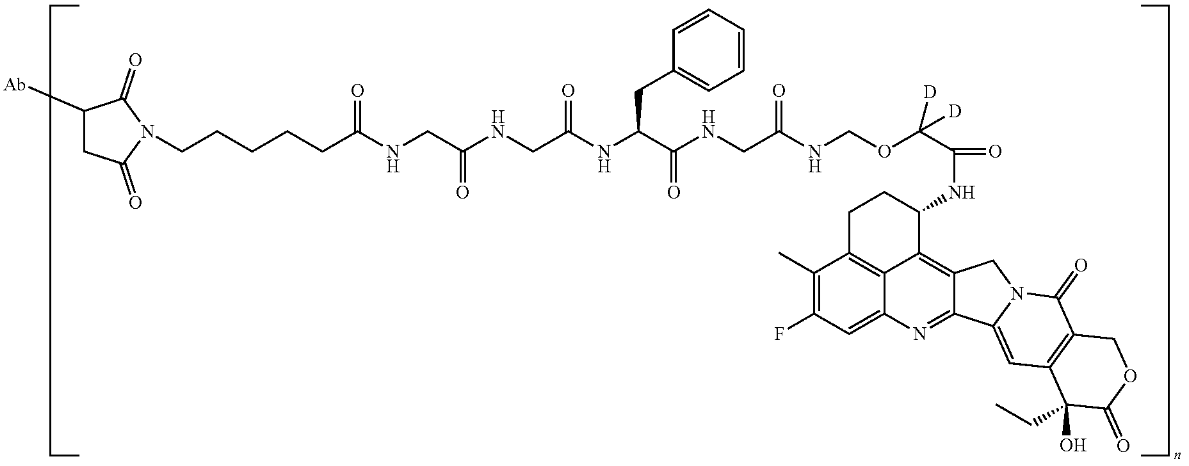

wherein,

Ab represents an antibody moiety comprising a first antigen-binding fragment and a second antigen-binding fragment, wherein the first antigen-binding fragment is an scFv, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 43, 28 and 29, respectively, and the light chain CDR1, the light chain CDR2 and the light chain CDR3 comprising amino acid sequences set forth in SEQ ID NOs: 30, 31 and 32, respectively;

the second antigen-binding fragment is an Fab, and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 45, 46 and 47, respectively, and the light chain CDR1, the light chain CDR2 and the light chain CDR3 comprising amino acid sequences set forth in SEQ ID NOs: 48, 49 and 50, respectively;

n is an integer or a decimal selected from the group consisting of 1 to 10.

In one specific embodiment, the present application provides an antibody-drug conjugate, or a pharmaceutically acceptable salt or a solvate thereof, having a structure of formula VII below,

VII

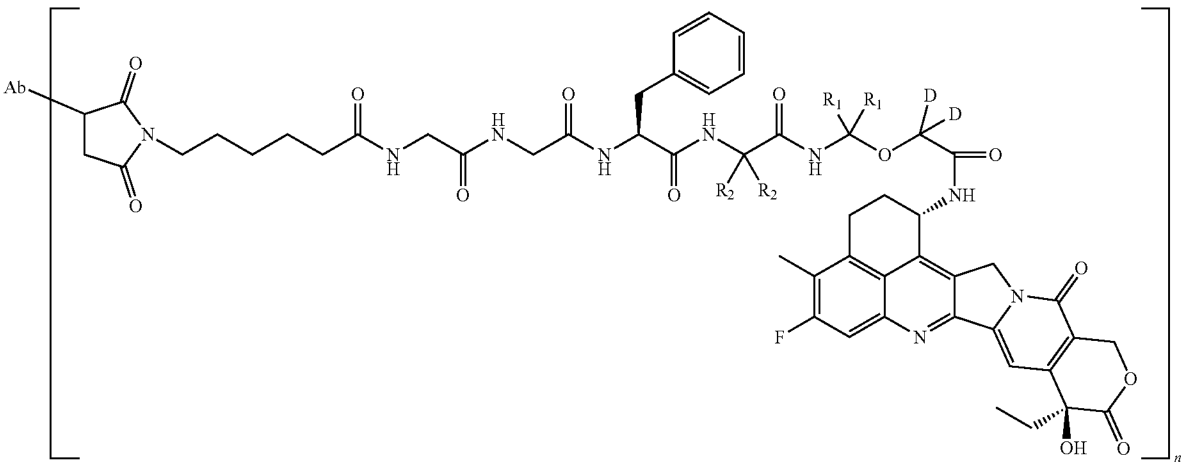

wherein,

Ab is trastuzumab, n is an integer or a decimal selected from the group consisting of 1 to 10, and $R_1$ and $R_2$ are each independently selected from the group consisting of hydrogen (H) and deuterium (D).

In one specific embodiment, the present application provides an antibody-drug conjugate, or a pharmaceutically acceptable salt or a solvate thereof, having a structure of formula VII-1 below,

VII-1

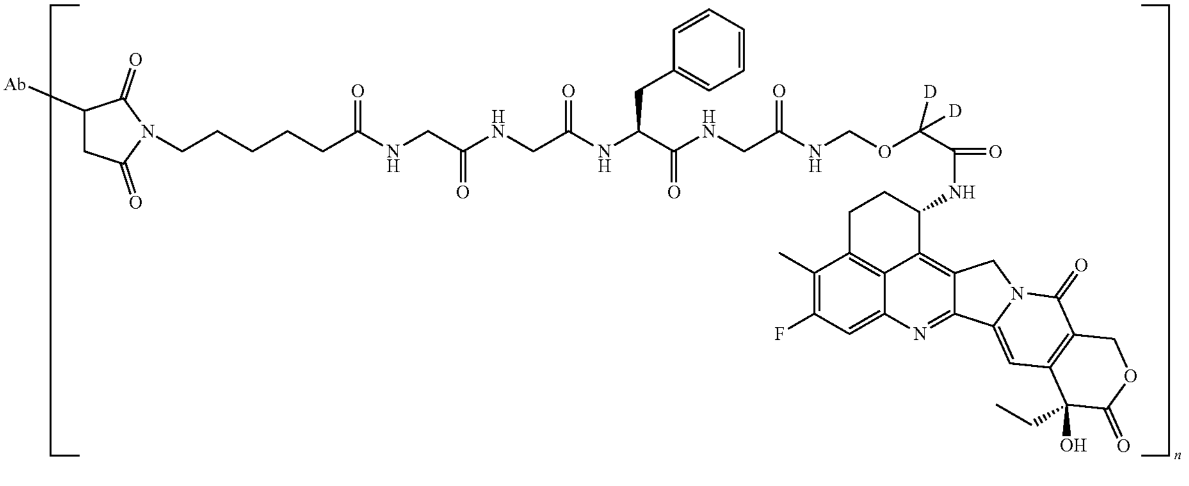

wherein,

Ab is trastuzumab, n is an integer or a decimal selected from the group consisting of 1 to 10.

In one aspect, the present application provides a pharmaceutical composition comprising the antibody-drug conjugate, or the pharmaceutically acceptable salt or the solvate thereof according to the present application, and a pharmaceutically acceptable carrier.

In one aspect, the present application provides use of the antibody-drug conjugate, or the pharmaceutically acceptable salt or the solvate thereof according to the present application, in preparing a medicament for preventing and treating cancer.

In one aspect, the present application provides use of a pharmaceutical composition comprising the antibody-drug conjugate, or the pharmaceutically acceptable salt or the solvate thereof according to the present application, and a pharmaceutically acceptable carrier in preparing a medicament for preventing and treating cancer.

In one aspect, the present application provides an antibody-drug conjugate, or a pharmaceutically acceptable salt or a solvate thereof for use in preventing and treating cancer.

In one aspect, the present application provides a method for treating or preventing cancer, the method comprising administering to a patient in need thereof a therapeutically effective amount of the antibody-drug conjugate, or the pharmaceutically acceptable salt or the solvate thereof according to the present application, or a pharmaceutical composition comprising the antibody-drug conjugate, or the pharmaceutically acceptable salt or the solvate thereof according to the present application, and a pharmaceutically acceptable carrier.

In some embodiments, the antibody-drug conjugate, or the pharmaceutically acceptable salt or the solvate thereof according to the present application, may be used for preventing or treating HER2 positive cancer, HER2 negative cancer (including triple-negative breast cancer), and cancer that shows HER2 expression as IHC2+ detected by immunohistochemical assay.

In some aspects, the present application provides a linker-drug intermediate compound having a structure of formula VI below, for use in obtaining an antibody-drug conjugate that links an antibody to the intermediate compound:

VI

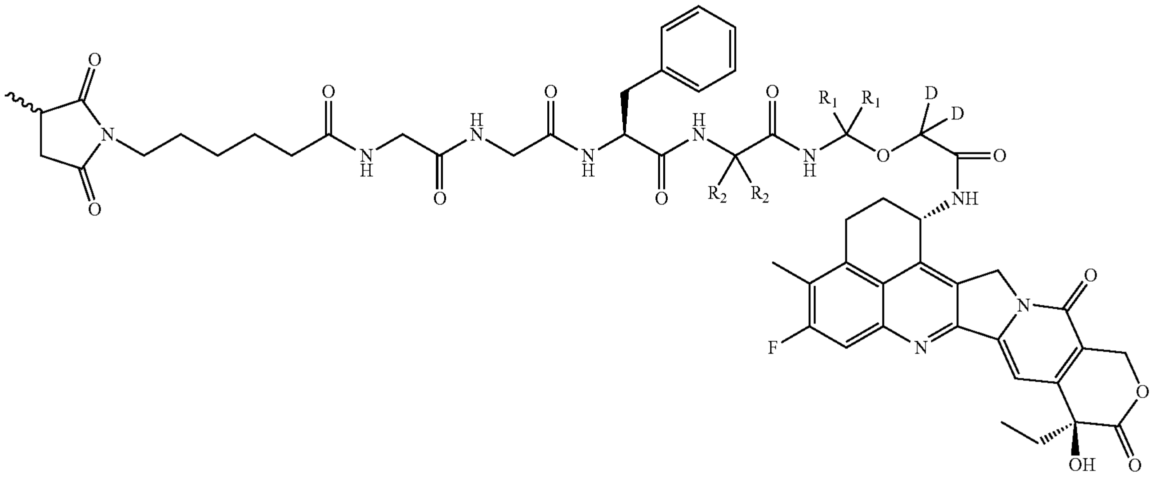

wherein $R_1$ and $R_2$ are each independently selected from the group consisting of hydrogen (H) and deuterium (D).

In some aspects, the present application provides a linker-drug intermediate compound having a structure of formula VI-1, VI-2, VI-3 or VI-4 below, for use in obtaining an antibody-drug conjugate that links an antibody to the intermediate compound:

VI-1

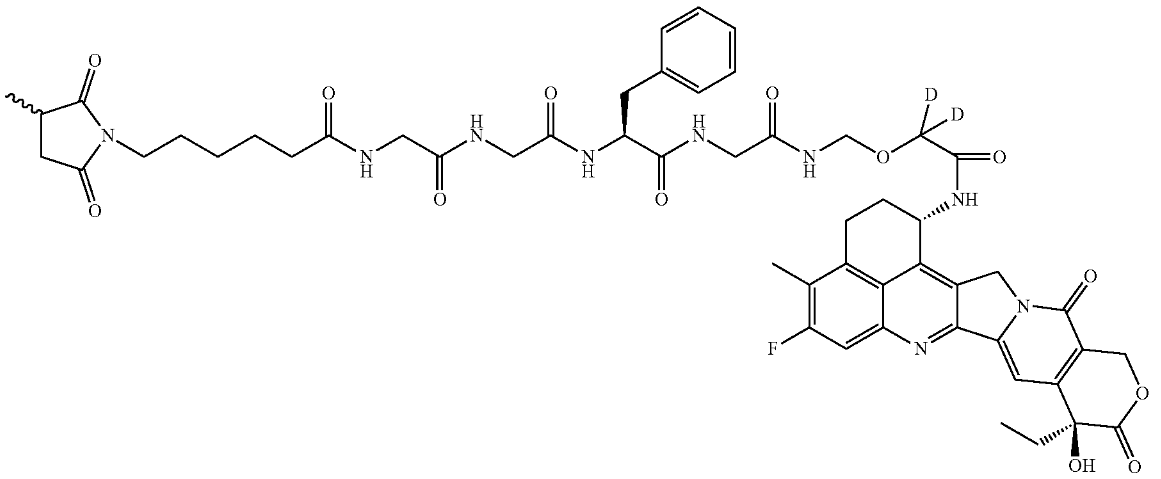

-continued
VI-2
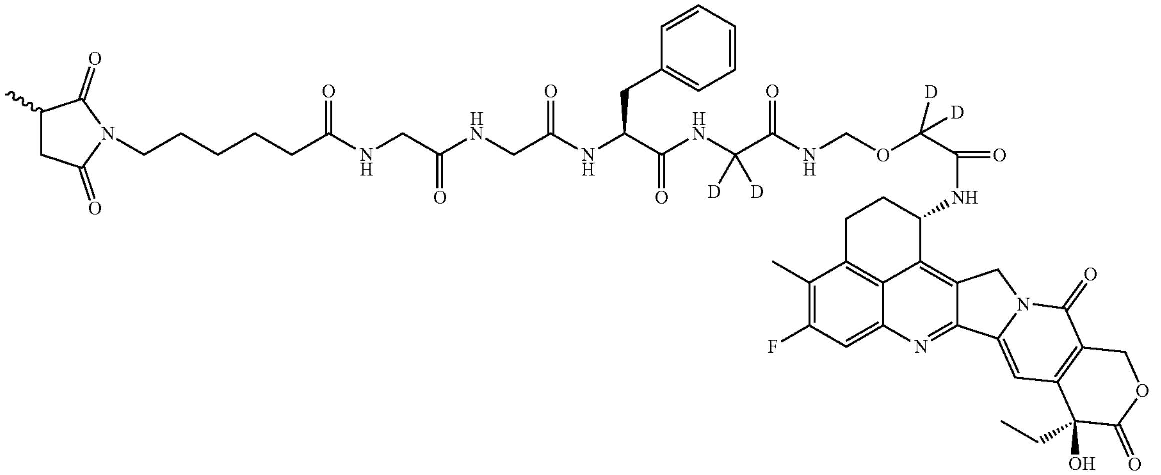
VI-3
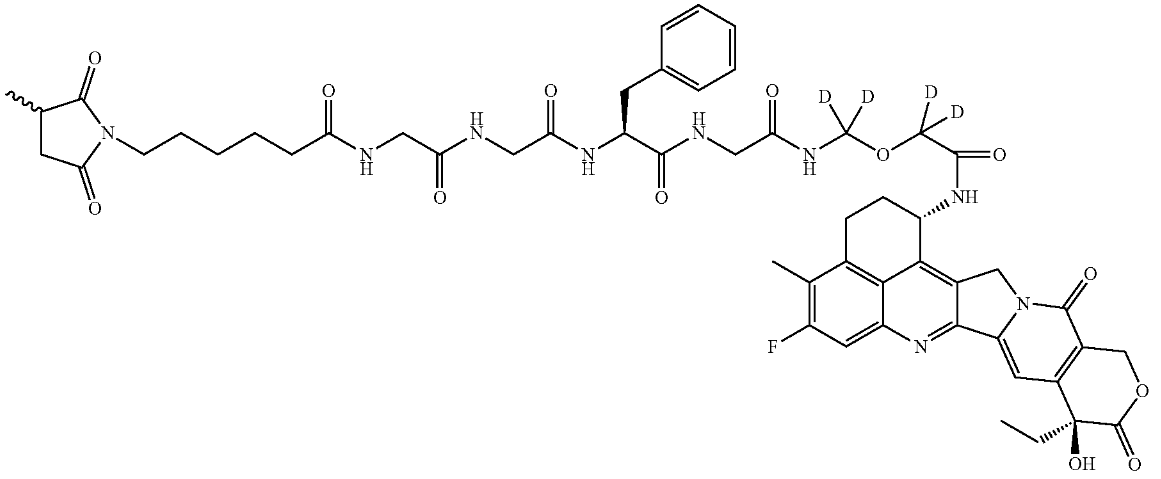
VI-4
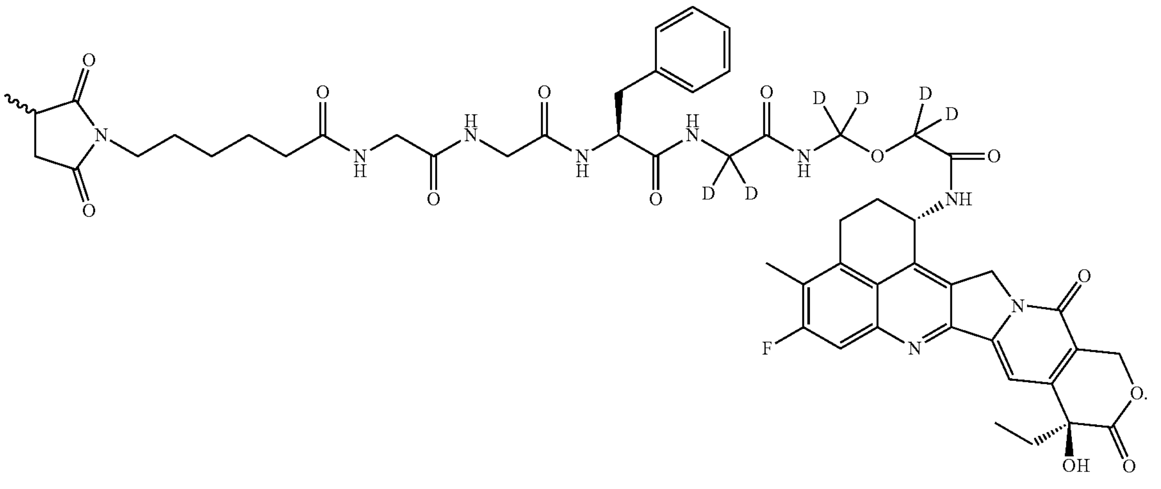

In some aspects, the present application provides a linker compound having a structure of formula V below, for use in obtaining an antibody-drug conjugate that links a drug to an antibody via the linker:

V

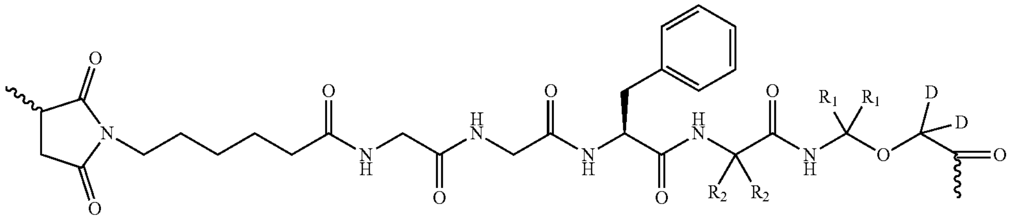

wherein $R_1$ and $R_2$ are each independently selected from the group consisting of hydrogen (H) and deuterium (D), and the left succinimide terminus of the structure is a site linking to the antibody moiety and the right carbonyl terminus is a site linking to the cytotoxic drug moiety.

In some aspects, the present application provides a linker compound having a structure of formula V-1, V-2, V-3, or V-4 below, for use in obtaining an antibody-drug conjugate that links a drug to an antibody via the linker, and the structures of formulas V-1 to V-4 are linked to the antibody moiety by the left succinimide terminus and the cytotoxic drug moiety by the right carbonyl terminus, respectively:

V-1

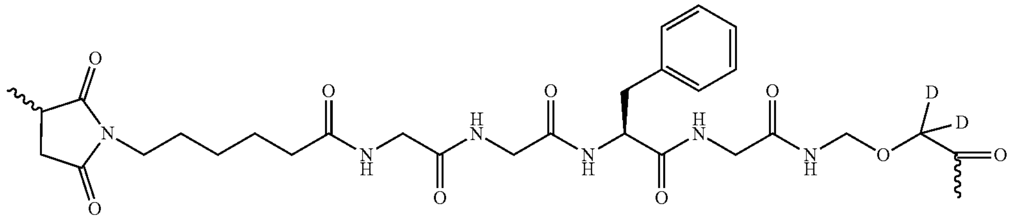

V-2

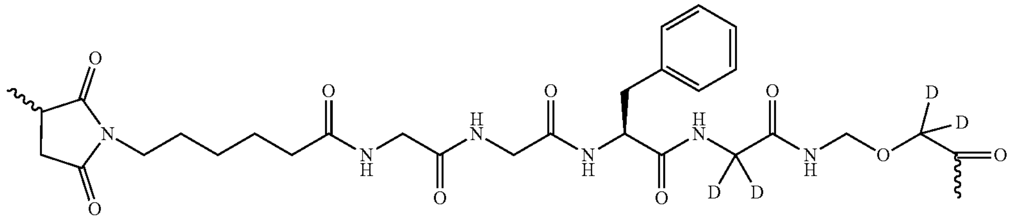

V-3

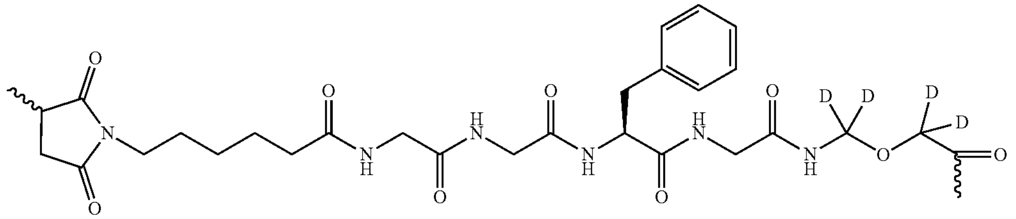

V-4

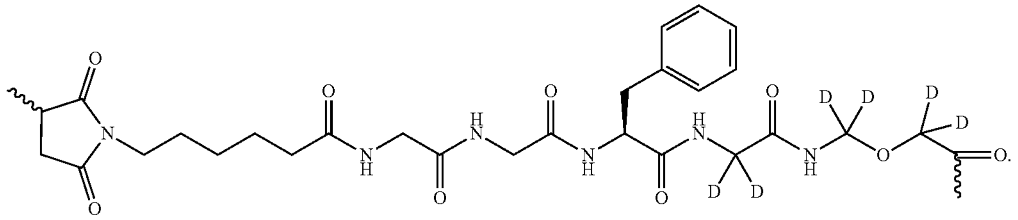

In some aspects, the present application provides a compound having a structure of formula IV(a) below:

IV(a)

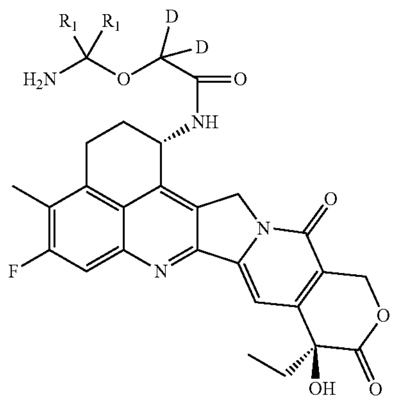

wherein $R_1$ is selected from the group consisting of hydrogen (H) and deuterium (D).

In some aspects, the present application provides a compound having a structure of formula IV(a)-1 or formula IV(a)-2 below:

IV(a)-1

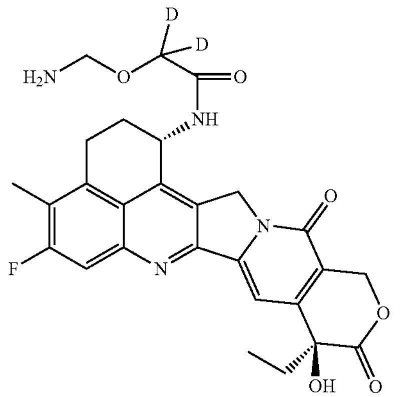

IV(a)-2

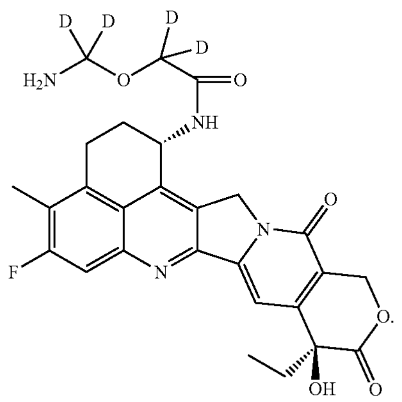

In some aspects, the present application provides a compound having a structure of formula III(a) below:

III(a)

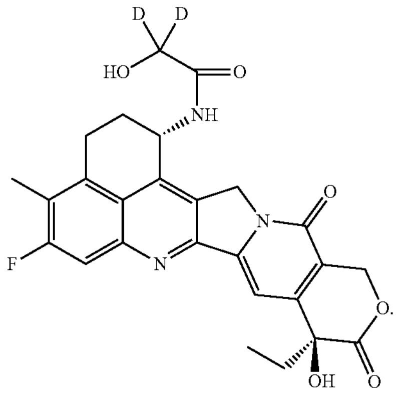

The present application provides an antibody-drug conjugate, or a pharmaceutically acceptable salt or a solvate thereof having improved pharmacokinetic properties. An improvement in pharmacokinetic properties will result in a reduction in toxicity of the target compound, an increase in safety and/or tolerability, an increase in efficacy and an improvement in the final therapeutic window.

EXPLANATION AND DEFINITIONS

Figure 1:
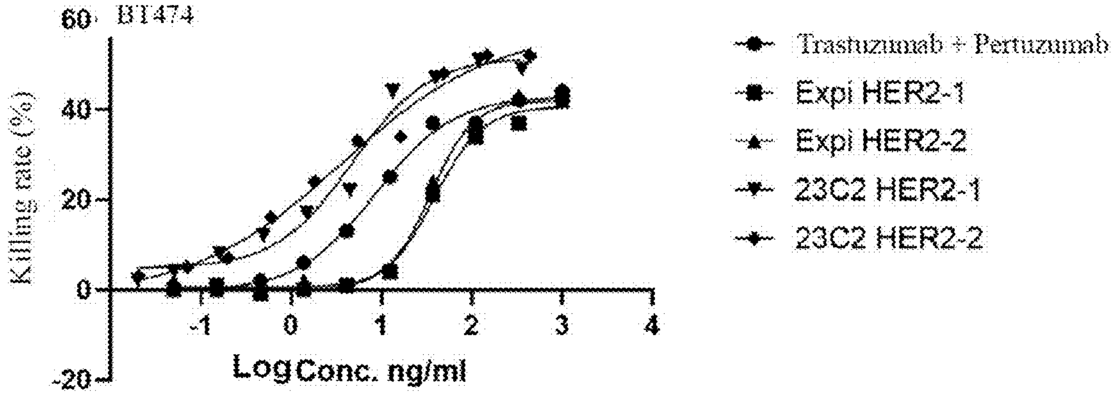
FIG. 1 shows the killing rates of anti-HER2 bispecific antibodies (Expi HER2-1, Expi HER2-2, 23C2 HER2-1 and 23C2 HER2-2) and the combination of trastuzumab+pertuzumab against BT474 tumor cells.

Unless otherwise stated, the following terms used herein shall have the following meanings. A certain term, unless otherwise specifically defined, should not be considered uncertain or unclear, but construed according to its common meaning in the field. Reference is made to, for example, Singleton et al., *Dictionary of Microbiology and Molecular Biology,* 2nd ed., J. Wiley & Sons (New York, NY 1994); Sambrook et al., *Molecular Cloning: A Laboratory Manual*, Cold Springs Harbor Press (Cold Springs Harbor, NY 1989); Davis et al., Basic Methods in Molecular Biology, Elsevier Science Publishing Inc., New York, USA (2012); Abbas et al., Cellular and Molecular Immunology, Elsevier Science Health Science div (2009); He Wei et al., *Medical Immunology*, (2nd ed), People's Medical Publishing House, 2010. When referring to a trade name herein, it is intended to refer to its corresponding commercial product or its active ingredient.

The term "substituted" means that any one or more hydrogen atoms on a specific atom are substituted by substituents, as long as the valence of the specific atom is normal and the resulting compound is stable. When the substituent is oxo (namely =O), it means that two hydrogen atoms are substituted, and oxo is not available on an aromatic group.

The term "optional" or "optionally" means that the subsequently described event or circumstance may, but not necessarily, occur. The description includes instances where the event or circumstance occurs and instances where the event or circumstance does not occur. A certain group being "optionally substituted" means that the group may be substituted or unsubstituted, for example, ethyl being "optionally" substituted with halogen means that the ethyl may be unsubstituted ($CH_2CH_3$), monosubstituted (for example, $CH_2CH_2F$), polysubstituted (for example, $CHFCH_2F$, $CH_2CHF_2$ and the like), or fully substituted ($CF_2CF_3$). It will be understood by those skilled in the art that for any groups comprising one or more substituents, any substitutions or substituting patterns which may not exist or cannot be synthesized spatially are not introduced.

$C_{m-n}$ used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms, or 6 carbon atoms.

When any variable (e.g., R) occurs more than once in the constitution or structure of a compound, the variable is independently defined in each case. Therefore, for example, if a group is substituted with 2 R, the definition of each R is independent.

When a connecting group has a number of 0, for example, $-(CH_2)_0-$, it means that the connecting group is a covalent bond.

When a variable is a single bond, it means that the two groups are directly connected. For example, in A-L-Z, when L represents a single bond, it means that the structure is actually A-Z.

The term "halo-" or "halogen" refers to fluorine, chlorine, bromine and iodine.

The term "hydroxy" refers to —OH group.

The term "cyano" refers to —CN group.

The term "sulfydryl" refers to —SH group.

The term "amino" refers to $-NH_2$ group.

The term "nitro" refers to $-NO_2$ group.

The term "alkyl" refers to hydrocarbyl with a general formula of $CH_nH_{2n+1}$. The alkyl can be linear or branched. For example, the term "$C_{1-6}$ alkyl" refers to alkyl containing 1 to 6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl and the like). The alkyl moieties (namely alkyl) of alkoxy, alkylamino, dialkylamino, alkylsulfonyl and alkylthio are similarly defined as above.

The term "alkoxyl" refers to —O-alkyl.

The term "alkylamino" refers to —NH-alkyl.

The term "dialkylamino" refers to $-N(alkyl)_2$.

The term "alkylsulfonyl" refers to $-SO_2$-alkyl.

The term "alkylthio" refers to —S-alkyl.

The term "alkenyl" refers to linear or branched unsaturated aliphatic hydrocarbyl consisting of carbon atoms and hydrogen atoms with at least one double bond. Non-limiting examples of alkenyl include, but are not limited to, ethenyl, 1-propenyl, 2-propenyl, 1-butenyl, isobutenyl, 1,3-butadienyl, and the like.

The term "alkynyl" refers to linear or branched unsaturated aliphatic hydrocarbyl consisting of carbon atoms and hydrogen atoms with at least one triple bond. Non-limiting examples of alkynyl include, but are not limited to, ethynyl ($-C\equiv CH$), 1-propinyl ($-C\equiv C-CH_3$), 2-propinyl ($-CH_2C\equiv CH$), 1,3-butadiynyl ($-C\equiv C-C\equiv CH$), and the like.

The term "cycloalkyl" refers to a carbon ring that is fully saturated and may exist in the form of a monocyclic, bridged cyclic, or spiro cyclic structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl(bicyclo[2.2.1]heptyl), bicyclo[2.2.2]octyl, adamantyl, and the like.

The term "cycloalkenyl" refers to a non-aromatic carbon ring that is not fully saturated and may exist in the form of a monocyclic, bridged cyclic, or spiro cyclic structure. Unless otherwise specified, the carbon ring is generally a 5-8 membered ring. Non-limiting examples of cycloalkenyl include, but are not limited to, cyclopentenyl, cyclopentadienyl, cyclohexenyl, cyclohexadienyl, cycloheptenyl, cycloheptadienyl, and the like.

The term "heterocyclyl" refers to a fully saturated or partially unsaturated (but not fully unsaturated heteroaromatic group) nonaromatic ring which may exist in the form of a monocyclic, bridged cyclic, or spiro cyclic structure. Unless otherwise specified, the heterocyclyl is usually a 3-7 membered ring containing 1-3 heteroatoms (preferably 1 or 2 heteroatoms) independently selected from the group consisting of sulfur, oxygen, and/or nitrogen. Non-limiting examples of heterocyclyl include, but are not limited to, oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl, and the like.

The term "heterocycloalkyl" refers to a fully saturated cyclic group that may exist in the form of a monocyclic, bridged cyclic, or Spiro cyclic structure. Unless otherwise specified, the heterocyclyl is usually a 3-7 membered ring containing 1-3 heteroatoms (preferably 1 or 2 heteroatoms) independently selected from the group consisting of sulfur, oxygen, and/or nitrogen. Examples of 3 membered heterocycloalkyl include, but are not limited to, oxiranyl, thiiranyl, and aziranyl; non-limiting examples of 4 membered heterocycloalkyl include, but are not limited to, azetidinyl, oxetanyl, and thietanyl; examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; examples of 6 membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,3-dithianyl, and 1,4-dithianyl; examples of 7 membered heterocycloalkyl include, but are not limited to, azacycloheptanyl, oxacycloheptanyl and thiocycloheptanyl. Preferably, the heterocycloalkyl is a monocyclic heterocycloalkyl having 5 or 6 ring atoms.

The term “aryl” refers to an aromatic monocyclic or fused polycyclic group of carbon atoms with the conjugated pi-electron system. For example, aryl may have 6-20 carbon atoms, 6-14 carbon atoms or 6-12 carbon atoms. Non-limiting examples of aryl include, but are not limited to, phenyl, naphthyl, anthryl, 1,2,3,4-tetrahydronaphthalene, and the like.

The term “heteroaryl” refers to a monocyclic or fused polycyclic system containing at least one ring atom selected from the group consisting of N, O and S, with the remaining ring atoms being C, and having at least one aromatic ring. Preferably, the heteroaryl has a single 4-8 membered ring, in particular, a 5-8 membered ring, or is a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The “derivative”: a compound formed by substituting atoms or atom groups in the molecule of the parent compound with other atoms or atom groups is referred to as a derivative of the parent compound.

Any atom of a compound labeled and synthesized herein may represent any stable isotope of the atom, if not specifically designated. Unless otherwise specified, when a position in a structure is defined as H, i.e., hydrogen (H-1), this position contains only the naturally occurring isotope. Similarly, unless otherwise specified, when a position in a structure is defined as D, i.e., deuterium (H-2), this position contains an isotope having an amount that is at least 3340 times greater than the amount of the naturally occurring isotope (0.015%) (i.e., at least 50.1% deuterium isotope), when one or more positions in the structure of the labeled synthetic compound are defined as D, i.e., deuterium (H-2), the content of the compound represented by the structure may be at least 52.5%, at least 60%, at least 67.5%, at least 75%, at least 82.5%, at least 90%, at least 95%, at least 97%, at least 98.5%, at least 99%, or at least 99.5%. The deuterated ratio of a compound labeled and synthesized herein refers to a ratio of the amount of the labeled synthetic isotope to the amount of the naturally occurring isotope. The deuterated ratio per designated deuterium atom of the compound labeled and synthesized herein may be at least 3500 times (52.5%), at least 4000 times (60%), at least 4500 times (67.5%), at least 5000 times (75%), at least 5500 times (82.5%), at least 6000 times (90%), at least 6333.3 times (95%), at least 6466.7 times (97%), at least 6566.7 times (98.5%), at least 6600 times (99%), at least 6633.3 times (99.5%). Isotopologues herein refer to compounds that differ only in isotopic composition in terms of chemical structure. The compound labeled and synthesized herein has the same chemical structure, with only isotopic changes in the atomic composition of its molecules. Therefore, the deuterium-containing compound at a specific position labeled and synthesized herein also contains very little hydrogen isotope at this position, and the amount of hydrogen isotopologue at a certain position in the compound labeled and synthesized herein depends on many factors, including the deuterium isotopic purity of the deuterated agent ($D_2O$, $D_2$, $NaBD_4$, $LiAlD_4$, and the like) and the effectiveness of introducing deuterium isotope synthesis methods. However, as previously mentioned, the total amount of such hydrogen isotopologue at a certain position will be less than 49.9%. The total amount of hydrogen isotopologue at a certain position in the compound labeled and synthesized herein will be less than 47.5%, 40%, 32.5%, 25%, 17.5%, 10%, 5%, 3%, 1%, or 0.5%.

In the present application, any individual atom not designated as deuterium is present at its natural isotopic abundance.

The term “treating” or “treatment” means administering the compound or formulation described herein to prevent, ameliorate, or eliminate a disease or one or more symptoms associated with the disease, including: (i) preventing the occurrence of the disease or disease state in a mammal, particularly when such a mammal is predisposed to the disease state but has not yet been diagnosed with it; (ii) inhibiting a disease or disease state, i.e., arresting its development; (iii) alleviating a disease or disease state, i.e., causing its regression.

The term “therapeutically effective amount” refers to an amount of the compound of the present application for (i) treating or preventing a specific disease, condition or disorder; (ii) alleviating, ameliorating or eliminating one or more symptoms of a specific disease, condition or disorder, or (iii) preventing or delaying onset of one or more symptoms of a specific disease, condition or disorder described herein. The amount of the compound of the present application composing the “therapeutically effective amount” varies dependently on the compound, the disease state and its severity, the route of administration, and the age of the mammal to be treated, but can be determined routinely by those skilled in the art in accordance with their knowledge and the present disclosure.

The term “pharmaceutically acceptable” is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term “solvate” refers to a substance formed by association of a compound with a solvent molecule. The term “pharmaceutical composition” refers to a mixture consisting of one or more of the compounds or the salts thereof disclosed herein and a pharmaceutically acceptable excipient. The pharmaceutical composition is intended to facilitate the administration of the compound to an organic entity.

The term “pharmaceutically acceptable excipients” refers to those which do not have a significant irritating effect on an organic entity and do not impair the biological activity and properties of the active compound. Suitable excipients are well known to those skilled in the art, for example carbohydrate, wax, water-soluble and/or water-swellable polymers, hydrophilic or hydrophobic material, gelatin, oil, solvent, water and the like.

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerism and imine-enamine isomerism. A specific example of a proton tautomer is an imidazole moiety where a proton can transfer between two ring nitrogens. A valence tautomer includes the interconversion via recombination of some bonding electrons.

The term "antibody" is used in its broadest sense and specifically encompasses intact monoclonal antibodies, polyclonal antibodies, multispecific antibodies (e.g., bispecific antibodies) formed from at least two intact antibodies, multifunctional antibodies, and antibody fragments so long as they possess the desired biological activity.

The term "humanized antibody" refers to an antibody comprising CDRs derived from a non-human antibody, and the remainder of the antibody molecule is derived from one or more human antibodies.

The term "mutant" is used to refer to a peptide comprising an amino acid sequence derived from the amino acid sequence of the peptide as follows: substitution of one or two or more amino acids with amino acids different from the original peptide, deletion of one or two or more wild-type amino acids, insertion of one or two or more amino acids that do not exist in the wild type, and/or addition of amino acids that do not exist in the wild type to the amino terminus (N-terminus) and/or the carboxy terminus (C-terminus) of the wild type (hereinafter, collectively referred to as "mutation"). In the present application, "insertion" may also be included in "addition".

The term "CDR" (complementarity-determining region), also known as "hypervariable region", refers to each region of an antibody variable domain which is highly variable in sequence and/or forms a structurally defined loop. Natural four-chain antibodies typically comprise six CDRs, three in the heavy chain variable region and three in the light chain variable region.

The term "variable region": the antibody structural unit is composed of two pairs of polypeptide chains, each pair having one heavy chain and one light chain, and the N-terminal domain of each chain defining a region of about 100 to 110 or more amino acids primarily responsible for antigen recognition is the variable region.

The term "Fab" means comprising the constant domain (CL) of the light chain and the first constant domain (CH1) of the heavy chain, together with the variable domains VL (light chain variable region) and VH (heavy chain variable region) in the light chain and heavy chain, respectively. The variable domain comprises complementarity-determining regions (CDRs) that are involved in antigen-binding.

The term "scFv" includes the VH and VL domains of an antibody, wherein these domains are present in a single polypeptide chain. In some embodiments, scFv further comprises a polypeptide linker between the VH and VL domains that enables the scFv to form the required structure for antigen-binding.

The term "ECD" refers to an extracellular domain. HER receptors are receptor protein tyrosine kinases belonging to the human epidermal growth factor receptor (HER) family and include EGFR, HER2, HER3, and HER4 receptors, wherein the HER2 receptor generally comprises an extracellular domain that may bind HER ligand, a lipophilic transmembrane domain, a conserved intracellular tyrosine kinase domain, and a carboxy-terminal signaling domain with several tyrosine residues that can be phosphorylated, and the extracellular domain of HER2 comprises four domains that are ECD1, ECD2, ECD3 and ECD4, respectively.

The term "antibody moiety" refers to an antibody moiety in an antibody-drug conjugate, which, in certain embodiments, is linked to an intermediate linker moiety via a specific functional group, and the antibody moiety can specifically bind to an antigen.

The term "linker moiety" refers to a part of the antibody-drug conjugate which links an antibody moiety with a cytotoxic drug moiety and may be cleavable or uncleavable, wherein the cleavable linker refers to a part which may be cleaved in a target cell so as to release the cytotoxic drug.

The term "cytotoxic drug moiety" refers to a cytotoxic drug moiety in an antibody-drug conjugate, and in certain specific embodiments, the cytotoxic drug moiety is linked to an intermediate linker moiety via a functional group, so that cytotoxic drug molecules can be liberated in tumor cells to exert an anti-tumor effect.

Generic term "trastuzumab" refers to a recombinant humanized monoclonal antibody that selectively acts on the extracellular site of human epidermal growth factor receptor-4 (HER4) and can be used to treat HER2 positive cancer, an example of which is the commercially available therapeutic monoclonal antibody product under the trade name HERCEPTIN®.

Generic term "pertuzumab" refers to a recombinant humanized monoclonal antibody that selectively acts on the extracellular site of human epidermal growth factor receptor-2 (HER2) and can be used to treat HER2 positive cancer.

The term "HER2" is a second member of the EGFR family having a tyrosine kinase activity, wherein HER2 expression levels can be detected by immunohistochemical assay, HER2 positive refers to IHC3+, HER2 negative refers to IHC1+/0, and for IHC2+, ISH assay should be performed for further clarification.

The term "cancer" refers to a physiological condition in mammals that is typically characterized by unregulated cell growth.

The term "triple-negative breast cancer" is a breast cancer that is negative for expression of estrogen receptors, progesterone receptors, and human epidermal growth factor receptor-2.

As used herein, unless otherwise stated, the terms "comprise", "comprises" and "comprising" or equivalents thereof (contain, contains, containing, include, includes, including) are open-ended statements and mean that elements, components and steps that are not specified may be included in addition to those listed.

As used herein, unless otherwise indicated, all numbers expressing the amounts of ingredients, measurements, or reaction conditions used herein are to be understood as being modified in all instances by the term "about". The term "about" when connected to a percentage may mean, for example, ±0.1%, preferably, ±0.05%, and more preferably, ±0.01%.

Unless otherwise specified clearly herein, singular terms encompass plural referents, and vice versa. Similarly, unless otherwise specified clearly herein, the word "or" is intended to include "and".

As used herein, the percent identity (degree of homology) between sequences can be determined by comparing the two sequences, for example, using freely available computer programs (e.g., BLASTp or BLASTn with default settings) typically used for this purpose on the World Wide Web (e.g., www.ncbi.nlm.nih.gov).

DETAILED DESCRIPTION

For clarity, the present application is further described with the following examples, which are, however, not intended to limit the scope of the present application. The reagents used herein are commercially available and can be used without further purification.

Trastuzumab and Pertuzumab used in the examples of the present application were prepared according to the conventional methods for antibodies, wherein vectors were constructed first, and eukaryotic cells were transfected and then purified for expression, with the sequence of Trastuzumab being referenced to WHO DRUG INFORMATION INN RL78, and the sequence of Pertuzumab being referenced to the examples of WO0100245. DS-8201 is the active ingredient of Enhertu, a commercially available formulation from Daiichi Sankyo Co., Ltd, and has the same structure as Trastuzumab-DXD prepared in the present application (see Example 15 for structure).

Example 1

Construction, Expression and Purification of Anti-Her2 scFv-Fc and Variants Thereof In constructing anti-Her2 scFv-Fc, human IgG1 was used as the Fc portion, and the variable region sequence of the anti-Her2 arm was a sequence based on the monoclonal antibody Herceptin®. The light and heavy chain variable regions of the monoclonal antibody Herceptin® were linked in series by a designed linker 1 (i.e., $(GGGGS)_3$) to form anti-Her2 scFv-Fc (SEQ ID NO: 1), the amino acid sequence of which is as follows:

```
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSGGGGSGGGGSGGGGSDIQMTQSPSSLSASV
GDRVTITCRASQDVNTAVAWYQQKPGKAPKLLIYSASFLYSGVPSRFSGS
RSGTDFTLTISSLQPEDFATYYCQQHYTTPPTFGQGTKVEIKGEPKSSDK
THTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNV
FSCSVMHEALHNHYTQKSLSLSPGK.
```

Further, point mutations were constructed in the anti-Her2 scFv-Fc sequence to construct the following variants:

anti-Her2-scFv-VL-F53Y-Fc (SEQ ID NO: 3): derived from wild-type anti-Her2 scFv-Fc, with an F53Y mutation in the VL region; the amino acid sequence is as follows:

```
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSGGGGSGGGGSGGGGSDIQMTQSPSSLSASV
GDRVTITCRASQDVNTAVAWYQQKPGKAPKLLIYSASYLYSGVPSRFSGS
RSGTDFTLTISSLQPEDFATYYCQQHYTTPPTFGQGTKVEIKGEPKSSDK
```

-continued

```
THTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNV
FSCSVMHEALHNHYTQKSLSLSPGK.
```

anti-Her2-scFv-VL-F53A-Fc (SEQ ID NO: 5): derived from wild-type anti-Her2 scFv-Fc, with an F53A mutation in the VL region; the amino acid sequence is as follows:

```
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSGGGGSGGGGSGGGGSDIQMTQSPSSLSASV
GDRVTITCRASQDVNTAVAWYQQKPGKAPKLLIYSASALYSGVPSRFSGS
RSGTDFTLTISSLQPEDFATYYCQQHYTTPPTFGQGTKVEIKGEPKSSDK
THTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNV
FSCSVMHEALHNHYTQKSLSLSPGK.
```

anti-Her2-scFv-VL-F53R-Fc (SEQ ID NO: 7): derived from wild-type anti-Her2 scFv-Fc, with an F53R mutation in the VL region; the amino acid sequence is as follows:

```
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSGGGGSGGGGSGGGGSDIQMTQSPSSLSASV
GDRVTITCRASQDVNTAVAWYQQKPGKAPKLLIYSASRLYSGVPSRFSGS
RSGTDFTLTISSLQPEDFATYYCQQHYTTPPTFGQGTKVEIKGEPKSSDK
THTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNV
FSCSVMHEALHNHYTQKSLSLSPGK.
```

anti-Her2-scFv-VH-K30E-Fc (SEQ ID NO: 9): derived from wild-type anti-Her2 scFv-Fc, with a K30E mutation in the VH region; the amino acid sequence is as follows:

```
EVQLVESGGGLVQPGGSLRLSCAASGFNIEDTYIHWVRQAPGKGLEWVAR
IYPTNGYTRYADSVKGRFTISADTSKNTAYLQMNSLRAEDTAVYYCSRWG
GDGFYAMDYWGQGTLVTVSSGGGGSGGGGSGGGGSDIQMTQSPSSLSASV
GDRVTITCRASQDVNTAVAWYQQKPGKAPKLLIYSASFLYSGVPSRFSGS
```

-continued

```
RSGTDFTLTISSLQPEDFATYYCQQHYTTPPTFGQGTKVEIKGEPKSSDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK.
```

The DNA sequences of anti-Her2 scFv-Fc and the variants thereof (SEQ ID NOs: 2, 4, 6, 8, and 10) were synthesized and each cloned into the pcDNA3.1 expression vector. The expression vector of anti-Her2 scFv-Fc or the variants thereof was transfected into ExpiCHO cells (CHO-S, Thermo) by using an ExpiCHO™ expression kit (Thermo Fisher, Cat. No. A29133). The cells were cultured in ExpiCHO expression medium in a humidified atmosphere in an incubator at 37° C. with 8% $CO_2$ on an orbital shaker spinning at 130 rpm. The culture supernatant was collected, and protein purification was performed using protein A magnetic beads (Genscript, Cat. No. L00273). The protein concentration was measured using a UV-Vis spectrophotometer (NanoDrop lite, Thermo Scientific).

TABLE 1

Sequence information about anti-Her2 scFv-Fc and the variants thereof

| Name | Amino acid sequence (SEQ ID NO) | Encoding DNA sequence (SEQ ID NO) | Mutation site in variable region |
|---|---|---|---|
| anti-Her2 scFv-Fc | 1 | 2 | None |
| anti-Her2-scFv-VL-F53Y-Fc | 3 | 4 | F53Y |
| anti-Her2-scFv-VL-F53A-Fc | 5 | 6 | F53A |
| anti-Her2-scFv-VL-F53R-Fc | 7 | 8 | F53R |
| anti-Her2-scFv-VH-K30E-Fc | 9 | 10 | K30E |

Example 2

Aggregate Verification and Human Her2 Antigen-Binding Assay of Anti-Her2 scFv-Fc and Variants Thereof For the expressed and purified anti-Her2 scFv-Fc and variants thereof, the affinity of the test molecules for human Her2 protein was determined by Biacore T200 (GE) as follows:

an amount of anti-Her2 scFv-Fc or a variant thereof was captured by a chip conjugated to Anti-hIgG, and then an antigen human HER2 protein (Sino Biological, Cat. No. 10004-H08H) was allowed to flow over the chip surface. The response signals were detected in real time using Biacore T200, and association and dissociation curves were obtained. The buffer used in the experiment was Biacore universal buffer (137 mM NaCl, 2.7 mM KCl, 10 mM $Na_2HPO_4 \cdot 12H_2O$, 1.8 mM $KH_2PO_4$, 0.05% surfactant P20 (GE, Cat. No. BR-1000-54), pH 7.4). Anti-hIgG (captured by human antibody capture kit, GE, Cat. No. 29-2346-00) was conjugated to a CM5 chip surface at a response value of up to about 9000 RU, and the response value after anti-Her2 scFv-Fc or a variant thereof captured was about 200 RU. Then the signal values of the interaction of different concentrations of human HER2 protein (100 nM, 50 nM, 25 nM, 12.5 nM, 6.25 nM, and 3.125 nM) with anti-Her2 scFv-Fc or the variant thereof were measured. The flow rate in the flow cell was at 50 μL/min, the association was performed for 240 s, the dissociation was performed for 1400 s, the regeneration was performed using 3 M $MgCl_2$ (GE) for 60 s, and the baseline was stable. Results were obtained by calculation according to the affinity and kinetics 1:1 binding mode in biacore evaluation software. The affinity of anti-Her2 scFv-Fc or the variants for the antigen human Her2 protein is shown in Table 2. Compared to anti-Her2 scFv-Fc (KD=0.77 nM), F53A mutation had a greater effect on the binding affinity of the variant anti-Her2-scFv-VL-F53A-Fc (KD=1.26 nM) for the antigen human Her2 protein. The variant anti-Her2-scFv-VL-F53Y-Fc (KD=0.8 nM) and anti-Her2 scFv-Fc (KD=0.77 nM) showed similar binding affinity for the antigen human Her2 protein. The variant anti-Her2-scFv-VH-K30E-Fc has a binding KD of 0.54 nM for the antigen human Her2 protein. It is known that the introduction of mutations F53Y and K30E does not reduce the binding affinity for the antigen human Her2 protein.

Components of anti-Her2 scFv-Fc or the variants thereof were separated by gel column chromatography, wherein the components were eluted out in descending order according to their molecular weights. The gel chromatography column used was an ACQUITY UPLC Protein BEH SEC Column 200 Å, 1.7 μm, 4.6×300 mm, and the column temperature was at 25° C. The mobile phase was 50 mmol/L phosphate-buffered saline-200 mmol/L sodium chloride at pH 7.0 (2.33 g of sodium dihydrogen phosphate dihydrate, 12.53 g of disodium hydrogen phosphate dodecahydrate and 11.69 g of sodium chloride were weighed into about 800 mL of ultrapure water and completely dissolved by stirring; ultrapure water was added until the volume reached 1000 mL; the mixture was well mixed and then filtered through a 0.22 μfilter membrane). The sample was diluted with the mobile phase to obtain a 10 mg/mL test solution, 2 μL of which was precisely measured out and injected into a liquid chromatograph (adjusting the volume of injection so that 20 μg of protein was injected if the sample concentration was less than 10 mg/mL) for detected at 280 nm. The flow rate was at 0.30 mL/min, and isocratic elution was performed for 15 min. Data was processed, and the results were quantitatively analyzed using the area normalization method. The peak area percentages for the aggregate, immunoglobulin monomer and low molecular weight impurities were calculated. The aggregate peak appeared before the main peak, which represents the immunoglobulin monomer, and the low molecular weight impurity peaks appeared after the main peak. The main peak and aggregate content percentages in anti-Her2 scFv-Fc or the variants thereof are shown in Table 2. The variants anti-Her2-scFv-VL-F53Y-Fc and anti-Her2-scFv-VH-K30E-Fc have significantly reduced aggregate, wherein the aggregate content was reduced from 6.31% (in anti-Her2 scFv-Fc) to 4.94% and 3.39%, respectively.

TABLE 2

| Aggregate content and binding affinity of anti-Her2 scFv-Fc and variants thereof for antigen Her2 | | | | | |
|---|---|---|---|---|---|
| Name | anti-Her2 scFv-Fc | anti-Her2-scFv-VL-F53Y-Fc | anti-Her2-scFv-VL-F53A-Fc | anti-Her2-scFv-VL-F53R-Fc | anti-Her2-scFv-VH-K30E-Fc |
| Aggregate | 6.31% | 4.94% | 6.96% | 7.83% | 3.39% |
| Monomer | 93.43% | 94.83% | 92.80% | 91.90% | 96.32% |
| Low molecular weight fragments | 0.25% | 0.24% | 0.23% | 0.26% | 0.28% |
| Antigen Her2 (KD) | 0.77 nM | 0.8 nM | 1.26 nM | Not measured | 0.54 nM |

Example 3

Construction, Expression and Purification of Anti-Her2 Bispecific Antibodies Anti-Her2 bispecific antibodies were produced as human IgG1 by knobs-into-holes (Ridgway, et al., 1996) Fc engineering. H435R and Y436F mutations (Jendeberg et al., 1997) were designed in the Fc region sequence of one heavy chain to reduce the affinity of Fc for protein A, which was favorable for removing the homodimers formed during the assembly of bispecific antibodies in the protein A affinity purification (U.S. Pat. No. 5,945,311A). It can be seen from Example 2 that anti-Her2-scFv-VL-F53Y-Fc mutation and anti-Her2-scFv-VH-K30E-Fc mutation could significantly reduce the anti-Her2-scFv aggregate while the affinity for Her2 antigen remained unchanged. The antigen-binding domain of one anti-Her2 arm of the anti-Her2 bispecific antibodies in this Example was in scFv (VH-linker-VL structure) form, and the variable region sequences comprised a mutation K30E (b-anti-Her2-scFv-VH-K30E-Fc, SEQ ID NO: 21), a mutation F53Y (b-anti-Her2-scFv-VL-F53Y-Fc, SEQ ID NO: 23), or both of the point mutations (anti-Her2-scFv-VH-K30E-VL-F53Y-Fc, SEQ ID NO: 11). The antigen-binding domain of another anti-Her2 arm of the anti-Her2 bispecific antibodies in this Example was in Fab form, including anti-Her2-domain2-HC-Fc (SEQ ID NO: 13) and anti-Her2-domain2-LC (SEQ ID NO: 15). Additionally, an anti-Her2 bispecific antibody without mutations was constructed in scFv form (VH-linker-VL structure or VL-linker-VH structure) as a control.

TABLE 3

| Sequence information about anti-Her2 bispecific antibodies | | | |
|---|---|---|---|
| Name | Composition | Amino acid sequence (SEQ ID NO) | Nucleotide sequence (SEQ ID NO) |
| Expi Her2-1 | anti-Her2-scFv-VL-VH-Fc | DIQMTQSPSSLSASVGDRVTITCRASQDVNTAVA WYQQKPGKAPKLLIYSASFLYSGVPSRFSGSRSGT DFTLTISSLQPEDFATYYCQQHYTTPPTFGQGTKV EIKGGSGGGSGGGSGGGSGGGSGEVQLVESGGGL VQPGGSLRLSCAASGFNIKDTYIHWVRQAPGKGL EWVARIYPTNGYTRYADSVKGRFTISADTSKNTA YLQMNSLRAEDTAVYYCSRWGGDGFYAMDYW GQGTLVTVSSAAEPKSSDKTHTCPPCPAPELLGGP SVFLFPPKPKDTLMISRTPEVTCVVVDVSHEDPEV KFNWYVDGVEVHNAKTKPREEQYNSTYRVVSVL TVLHQDWLNGKEYKCKVSNKALPAPIEKTISKAK GQPREPQVYTLPPSRDELTKNQVSLICLVKGFYPS DIAVEWESNGQPENRYMTWPPVLDSDGSFFLYSK LTVDKSRWQQGNVFSCSVMHEALHNHYTQKSLS LSPGK (SEQ ID NO: 17) | 18 |
| | anti-Her2-domain2-HC-Fc-2 | EVQLVESGGGLVQPGGSLRLSCAASGFTFTDYTM DWVRQAPGKGLEWVADVNPNSGGSIYNQRFKGR FTLSVDRSKNTLYLQMNSLRAEDTAVYYCARNL GPSFYFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNV NHKPSNTKVDKKVEPKSCDKTHTCPPCPAPELLG GPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPQVYVYPPSRDELTKNQVSLTCLVKGF YPSDIAVEWESNGQPENNYKTTPPVLDSDGSFAL VSKLTVDKSRWQQGNVFSCSVMHEALHNRFTQK SLSLSPG (SEQ ID NO: 19) | 20 |
| | anti-Her2-domain2-LC | DIQMTQSPSSLSASVGDRVTITCKASQDVSIGVAW YQQKPGKAPKLLIYSASYRYTGVPSRFSGSGSGTD FTLTISSLQPEDFATYYCQQYYIYPYTFGQGTKVEI KRTVAAPSVFIFPPSDEQLKSGTASVVCLLNNFYP REAKVQWKVDNALQSGNSQESVTEQDSKDSTYS | 16 |

TABLE 3-continued

Sequence information about anti-Her2 bispecific antibodies

| Name | Composition | Amino acid sequence (SEQ ID NO) | Nucleotide sequence (SEQ ID NO) |
|---|---|---|---|
| | | LSSTLTLSKADYEKHKVYACEVTHQGLSSPVTKS FNRGEC (SEQ ID NO: 15) | |
| Expi Her2-2 | anti-Her2-scFv-VH-K30E-VL-F53Y-Fc | EVQLVESGGGLVQPGGSLRLSCAASGFNIEDTYIH WVRQAPGKGLEWVARIYPTNGYTRYADSVKGRF TISADTSKNTAYLQMNSLRAEDTAVYYCSRWGG DGFYAMDYWGQGTLVTVSSGGGGSGGGGSGGG GSGGGGSDIQMTQSPSSLSASVGDRVTITCRASQD VNTAVAWYQQKPGKAPKLLIYSASYLYSGVPSRF SGSRSGTDFTLTISSLQPEDFATYYCQQHYTTPPTF GQGTKVEIKGEPKSSDKTHTCPPCPAPELLGGPSV FLFPPKPKDTLMISRTPEVTCVVVDVSHEDPEVKF NWYVDGVEVHNAKTKPREEQYNSTYRVVSVLTV LHQDWLNGKEYKCKVSNKALPAPIEKTISKAKGQ PREPQVYTLPPCREEMTKNQVSLWCLVKGFYPSD IAVEWESNGQPENNYKTTPPVLDSDGSFFLYSKLT VDKSRWQQGNVFSCSVMHEALHNHYTQKSLSLS PGK (SEQ ID NO: 11) | 12 |
| | anti-Her2-domain2-HC-Fc | EVQLVESGGGLVQPGGSLRLSCAASGFTFTDYTM DWVRQAPGKGLEWVADVNPNSGGSIYNQRFKGR FTLSVDRSKNTLYLQMNSLRAEDTAVYYCARNL GPSFYFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNV NHKPSNTKVDKKVEPKSCDKTHTCPPCPAPELLG GPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPQVCTLPPSREEMTKNQVSLSCAVKGF YPSDIAVEWESNGQPENNYKTTPPVLDSDGSFFLV SKLTVDKSRWQQGNVFSCSVMHEALHNRFTQKS LSLSPGK (SEQ ID NO: 13) | 14 |
| | anti-Her2-domain2-LC | DIQMTQSPSSLSASVGDRVTITCKASQDVSIGVAW YQQKPGKAPKLLIYSASYRYTGVPSRFSGSGSGTD FTLTISSLQPEDFATYYCQQYYIYPYTFGQGTKVEI KRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC (SEQ ID NO: 15) | 16 |
| Expi Her2-3 | b-anti-Her2-scFv-VH-K30E-Fc | EVQLVESGGGLVQPGGSLRLSCAASGFNIEDTYIH WVRQAPGKGLEWVARIYPTNGYTRYADSVKGRF TISADTSKNTAYLQMNSLRAEDTAVYYCSRWGG DGFYAMDYWGQGTLVTVSSGGGGSGGGGSGGG GSGGGGSDIQMTQSPSSLSASVGDRVTITCRASQD VNTAVAWYQQKPGKAPKLLIYSASFLYSGVPSRF SGSRSGTDFTLTISSLQPEDFATYYCQQHYTTPPTF GQGTKVEIKGEPKSSDKTHTCPPCPAPELLGGPSV FLFPPKPKDTLMISRTPEVTCVVVDVSHEDPEVKF NWYVDGVEVHNAKTKPREEQYNSTYRVVSVLTV LHQDWLNGKEYKCKVSNKALPAPIEKTISKAKGQ PREPQVYTLPPCREEMTKNQVSLWCLVKGFYPSD IAVEWESNGQPENNYKTTPPVLDSDGSFFLYSKLT VDKSRWQQGNVFSCSVMHEALHNHYTQKSLSLS PGK (SEQ ID NO: 21) | 22 |
| | anti-Her2-domain2-HC-Fc | SEQ ID NO: 13 | 14 |
| | anti-Her2-domain2-LC | SEQ ID NO: 15 | 16 |
| Expi Her2-4 | b-anti-Her2-scFv-VL-F53Y-Fc | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGG DGFYAMDYWGQGTLVTVSSGGGGSGGGGSGGG GSGGGGSDIQMTQSPSSLSASVGDRVTITCRASQD VNTAVAWYQQKPGKAPKLLIYSASYLYSGVPSRF SGSRSGTDFTLTISSLQPEDFATYYCQQHYTTPPTF GQGTKVEIKGEPKSSDKTHTCPPCPAPELLGGPSV FLFPPKPKDTLMISRTPEVTCVVVDVSHEDPEVKF NWYVDGVEVHNAKTKPREEQYNSTYRVVSVLTV | 24 |

TABLE 3-continued

Sequence information about anti-Her2 bispecific antibodies

| Name | Composition | Amino acid sequence (SEQ ID NO) | Nucleotide sequence (SEQ ID NO) |
|---|---|---|---|
| | | LHQDWLNGKEYKCKVSNKALPAPIEKTISKAKGQ PREPQVYTLPPCREEMTKNQVSLWCLVKGFYPSD IAVEWESNGQPENNYKTTPPVLDSDGSFFLYSKLT VDKSRWQQGNVFSCSVMHEALHNHYTQKSLSLS PGK (SEQ ID NO: 23) | |
| | anti-Her2-domain2-HC-Fc | SEQ ID NO: 13 | 14 |
| | anti-Her2-domain2-LC | SEQ ID NO: 15 | 16 |
| Expi Her2-5 | anti-Her2-scFv-VH-VL-Fc | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGG DGFYAMDYWGQGTLVTVSSGGGGSGGGGSGGG GSGGGGSDIQMTQSPSSLSASVGDRVTITCRASQD VNTAVAWYQQKPGKAPKLLIYSASFLYSGVPSRF SGSRSGTDFTLTISSLQPEDFATYYCQQHYTTPPTF GQGTKVEIKGEPKSSDKTHTCPPCPAPELLGGPSV FLFPPKPKDTLMISRTPEVTCVVVDVSHEDPEVKF NWYVDGVEVHNAKTKPREEQYNSTYRVVSVLTV LHQDWLNGKEYKCKVSNKALPAPIEKTISKAKGQ PREPQVYTLPPCREEMTKNQVSLWCLVKGFYPSD IAVEWESNGQPENNYKTTPPVLDSDGSFFLYSKLT VDKSRWQQGNVFSCSVMHEALHNHYTQKSLSLS PGK (SEQ ID NO: 25) | 26 |
| | anti-Her2-domain2-HC-Fc | SEQ ID NO: 13 | 14 |
| | anti-Her2-domain2-LC | SEQ ID NO: 15 | 16 |

The DNA sequences of anti-Her2 bispecific antibodies (SEQ ID NOs: 12, 14 and 16) were synthesized and each cloned into the pcDNA3.1 expression vector. The expression vectors of anti-Her2-scFv-VH-K30E-VL-F53Y-Fc (SEQ ID NO: 11), anti-Her2-domain2-HC-Fc (SEQ ID NO: 13) and anti-Her2-domain2-LC (SEQ ID NO: 15) were co-transfected into ExpiCHO cells in a transfection ratio of 1:1:1.5 using a CHOgro® high yield expression system (Cat. No. $MIR_{6270}$). The transfection density was $6\times10^6$ cells/mL. The medium was CHOgro® expression medium (Cat. No. $MIR_{6200}$, manufacturer: Mirus). The culture was continued until day 10 after transfection, and the cell culture supernatant was collected by centrifugation. Protein purification was performed using protein A magnetic beads (Genscript, Cat. No. L00273). The protein concentration was measured using a UV-Vis spectrophotometer (NanoDrop lite, Thermo Scientific). This sample was designated as Expi Her2-2. With reference to this method, other bispecific antibodies, Expi Her2-1, Expi Her2-3, Expi Her2-4, and Expi Her2-5, were obtained by expression and purification.

Example 4

Preparation and Verification of Fucose Knockout Bispecific Antibodies

The interaction of IgG1 with FcgRIIIa can be improved by knocking out the fucose expression-related gene FUT8, and thereby the ADCC of the antibody is enhanced (Shields et al., 2002; Yamane-Ohnuki et al., 2004). In this example, fucose knockout anti-Her2 bispecific antibodies were prepared using FUT8− knockout CHO-S cells (designated as CHO FUT8−/− cells). The DNA sequences of anti-Her2 bispecific antibodies (SEQ ID NOs: 12, 14 and 16) were synthesized and each cloned into the pcDNA3.1 expression vector, respectively. The expression vectors of anti-Her2-scFv-VH-K30E-VL-F53Y-Fc, anti-Her2-domain2-HC-Fc and anti-Her2-domain2-LC were co-transfected into the FUT8-knockout CHO-S cells in a transfection ratio of 1:1:1.5 using a CHOgro® high yield expression system (Cat. No. $MIR_{6270}$). The transfection density was $6\times10^6$ cells/mL. The medium was CHOgro® expression medium (Cat. No. $MIR_{6200}$, manufacturer: Mirus). The culture was continued until day 10 after transfection, and the cell culture supernatant was collected by centrifugation. Protein purification was performed using protein A magnetic beads (Genscript, Cat. No. L00273). The protein concentration was measured using a UV-Vis spectrophotometer (NanoDrop lite, Thermo Scientific). This sample was designated as 23C2 Her2-2. With reference to this method, the sequences of Expi Her2-1, Expi Her2-3, Expi Her2-4, and Expi Her2-5 were expressed in the CHO FUT8−/− cells to obtain corresponding fucose knockout anti-Her2 bispecific antibodies 23C2 Her2-1, 23C2 Her2-3, 23C2 Her2-4, and 23C2 Her2-5.

The anti-Her2 bispecific antibody samples expressed by the CHO FUT8−/− cells and CHO-S cells were processed using a GlycoWorks RapiFluor-MS N-Glycan kit (Waters, Milford, Mass., USA). The N-glycans were released from protein and labeled. After column chromatography separation, analysis was performed using an FLR detector (Waters, Milford, Mass., USA), and the structure and content of N-glycan could be obtained. The glycan content percentages are shown in Table 4. In the normal anti-Her2 bispecific antibody Expi HER2-2, the percentage of de-fucosylated glycans was 21.85%, and in the anti-Her2 bispecific antibody 23C2 HER2-2 expressed by FUT8− knockout CHO-S cells, the percentage of de-fucosylated glycans was 99.40%.

TABLE 4

Glycan content analysis of anti-Her2 bispecific antibodies

| Component name | Content (%) Expi HER2-2 | 23C2 HER2-2 |
|---|---|---|
| A1(M3B) | 1.81 | 9.84 |
| A1G(4)1 | 0.16 | 0.17 |
| A2 | 1.14 | 70.33 |
| A2[3]G(4)1 | / | 2.34 |
| A2[6]G(4)1 | / | 4.19 |
| A2[3]BG(4)1 | / | 0.11 |
| A2G(4)2 | / | 0.55 |
| A2G(4)2S(3)1 | / | 0.21 |
| A2G(4)2S(3,3)2 | / | 0.46 |
| F(6)A1G(4)1 | / | / |
| F(6)A1[3]G(4)1S(3)1 | / | / |
| F(6)A1 | 12.77 | / |
| F(6)A2 | 60.69 | 0.60 |
| F(6)A2[3]G(4)1 | 1.20 | / |
| F(6)A2[6]G(4)1 | 0.70 | / |
| F(6)A2G(4)2 | / | / |
| F(6)A2G(4)2S(3)1 | / | / |
| M3 | / | 0.26 |
| M4 | / | 0.07 |
| M4A1G(4)1 | / | 0.36 |
| M4 D1 | / | 0.08 |
| M5 | 12.31 | 5.67 |
| M5A1G(4)1 | / | 0.05 |
| M6 D1 | 2.11 | 0.75 |
| M6 D3 | 0.73 | 0.18 |
| M7 D1 | 0.80 | 0.44 |
| M8 | 0.20 | 0.15 |
| De-fucosylated glycans | 21.85 | 99.40 |
| Di-sialylated glycans | / | 0.46 |
| High mannose glycans | 20.07 | 7.24 |
| Mono-sialylated glycans | 0.18 | 0.21 |
| Non-sialylated glycans | 99.82 | 99.33 |

Example 5

Aggregate Verification of Bispecific Antibodies

This example relates to aggregate verification of anti-her2 bispecific antibodies 23C2 Her2-1, 23C2 Her2-2, 23C2 Her2-3, 23C2 Her2-4, and 23C2 Her2-5.

The anti-her2 bispecific antibodies were separated by gel column chromatography, and the aggregate content was verified, wherein the components were eluted out in descending order according to their molecular weights. The gel chromatography column used was an ACQUITY UPLC Protein BEH SEC Column 200 Å, 1.7 μm, 4.6×300 mm, and the column temperature was at 25° C. The mobile phase was 50 mmol/L phosphate-buffered saline-200 mmol/L sodium chloride at pH 7.0 (2.33 g of sodium dihydrogen phosphate dihydrate, 12.53 g of disodium hydrogen phosphate dodecahydrate and 11.69 g of sodium chloride were weighed into about 800 mL of ultrapure water and completely dissolved by stirring; ultrapure water was added until the volume reached 1000 mL; the mixture was well mixed and then filtered through a 0.22 μm filter membrane). The sample was diluted with the mobile phase to obtain a 10 mg/mL test solution, 2 μL of which was precisely measured out and injected into a liquid chromatograph (adjusting the volume of injection so that 20 jug of protein was injected if the sample concentration was less than 10 mg/mL) for detected at 280 nm. The flow rate was at 0.30 mL/min, and isocratic elution was performed for 15 min. Data was processed, and the results were quantitatively analyzed using the area normalization method. The peak area percentages for the aggregate, immunoglobulin monomer and low molecular weight impurities were calculated. The aggregate peak appeared before the main peak, which represents the immunoglobulin monomer, and the low molecular weight impurity peaks appeared after the main peak.

TABLE 5

Aggregate content of anti-Her2 bispecific antibodies

| Sample name | Aggregate | Monomer | Low molecular weight fragments |
|---|---|---|---|
| 23C2 Her2-2 | 8.51% | 91.02% | 0.47% |
| 23C2 Her2-1 | 19.55% | 80.05% | 0.40% |

The results show that after scFVs were assembled into bispecific antibodies, the assembled bispecific antibodies still produced a large amount of aggregate; however, the aggregate content in the bispecific antibodies can be reduced by introducing mutations. The aggregate content in 23C2 Her2-2 can be reduced to 8.51% compared to that in 23C2 Her2-1 comprising no mutation (Table 5).

Example 6

Antigen-Binding Assay of Anti-Her2 Bispecific Antibodies

For the expressed and purified anti-Her2 bispecific antibodies, the affinity of the test molecules for HER2 protein was determined by Biacore T200 (GE) as follows:

An amount of an anti-Her2 bispecific antibody was captured by a chip coupled to Anti-hIgG, and then human Her2 (Sino Biological, Cat. No. 10004-H08H) was allowed to flow over the chip surface. The response signals were detected in real time using Biacore T200, and association and dissociation curves were obtained. The buffer used in the experiment was Biacore universal buffer (137 mM NaCl, 2.7 mM KCl, 10 mM $Na_2HPO_4 \cdot 12H_2O$, 1.8 mM $KH_2PO_4$, 0.05% surfactant P20, pH 7.4). Anti-hIgG (captured by human antibody capture kit, GE, Cat. No. 29-2346-00) was conjugated to a CMS chip surface at a response value of up to about 9000 RU, and the response value of the captured anti-Her2 bispecific antibody was about 200 RU. Then the signal values of the interaction of different concentrations of Her2 protein (100 nM, 50 nM, 25 nM, 12.5 nM, 6.25 nM, and 3.125 nM) with the anti-Her2 bispecific antibody were measured. The flow rate in the flow cell was at 50 μL/min, the association was performed for 240 s, the dissociation was performed for 1400 s, the regeneration was performed using 3 M MgCl 2 (GE) for 60 s, and the baseline was stable.

The results were obtained by calculation according to biacore evaluation software. The binding affinity of the anti-Her2 bispecific antibody 23C2 Her2-2, as well as the controls trastuzumab and pertuzumab, for antigen Her2 is shown in Table 6. The binding KD of the anti-Her2 bispecific antibody 23C2 Her2-2 for antigen Her2 is 6.11E-10 M, the binding KD of trastuzumab for antigen Her2 is 1.22E-09 M, and the binding KD of pertuzumab for antigen Her2 is 2.35E-09 M. The anti-Her2 bispecific antibody 23C2 Her2-2 showed higher affinity than trastuzumab and pertuzumab for antigen Her2.

TABLE 6

| Affinity of anti-Her2 bispecific antibodies for human Her2 antigen | | | |
|---|---|---|---|
| | ka (1/Ms) | kd (1/s) | KD (M) |
| 23C2 Her2-2 | 1.79E+05 | 1.09E−04 | 6.11E−10 |
| Trastuzumab control sample | 1.73E+05 | 2.12E−04 | 1.22E−09 |
| Pertuzumab control sample | 1.15E+05 | 2.69E−04 | 2.35E−09 |

Example 7

Antigen-Binding Assay of Anti-Her2 Bispecific Antibodies

With reference to the procedures in Example 6, the affinity of the expressed and purified anti-Her2 bispecific antibodies 23C2 Her2-1, 23C2 Her2-2, 23C2 Her2-3, 23C2 Her2-4, and 23C2 Her2-5 for HER2 protein was determined by Biacore T200 (GE).

The result of the affinity determination of the anti-Her2 bispecific antibody 23C2 Her2-1 for the antigen human Her2 protein is shown in Table 7. It can be seen from the results in Tables 6 and 7 that the binding affinity of the anti-Her2 bispecific antibodies for the antigen human Her2 protein can be improved by introducing F53Y and K30E mutations.

TABLE 7

| Affinity of anti-Her2 bispecific antibodies for human Her2 antigen | |
|---|---|
| Sample name | 23C2 Her2-1 |
| Antigen Her2 KD | 4.02 nM |

Example 8

Killing of Her2 Positive Target Cell BT474 by Anti-Her2 Bispecific Antibodies The killing effects of the anti-Her2 bispecific antibodies on target cells (BT474 Her2+++, source: the Cell Bank of Type Culture Collection Committee of the Chinese Academy of Sciences) were studied using NK cells provided by human PBMCs (peripheral blood mononuclear cells), and the in vitro activity of the anti-Her2 bispecific antibodies was assessed by EC 50 value.

The specific procedures are as follows: BT474 cells were adjusted to a cell density of $3\times10^5$ cells/mL using 1640 medium containing 2% FBS (fetal bovine serum) and seeded in a 96-well cell culture plate (eppendorf, Cat. No. 0030730199) at 50 μL per well. Different concentrations of the anti-Her2 bispecific antibodies (1000 ng/mL, 333 ng/mL, 111 ng/mL, 37 ng/mL, 12.3 ng/mL, 4.11 ng/mL, 1.37 ng/mL, 0.46 ng/mL, 0.15 ng/mL and 0.05 ng/mL) were prepared using 1640 medium and added to the above 96-well cell culture plate at 50 μL per well. Human PBMCs were adjusted to a cell density of $1.5\times10^6$ cells/mL using 1640 medium and added at 100 μL per well. An administration group (target cell+effector cell+antibody), a target cell group (BT474 cell), an effector cell group (human PBMC), a target cell+effector cell group, a blank control group (medium) and a lysis solution control group, and a target cell maximum release group (target cell+lysis solution) were set, with the effector-to-target cell ratio being 10:1. 45 min prior to the assay, 20 μL/well of lysis solution (Promega, Cat. No. G182A) was added to the target cell maximum release group and the lysis solution control group. After 45 min, the cell lysis rates were measured using a CytoTox96® nonradioactive cytotoxicity assay (Promega, G1780).

$$\text{Rate of lysis }(\%)=(OD_{administration\ group}-OD_{target\ cell+effector\ cell\ group})/(OD_{target\ cell\ maximum\ release\ group}-OD_{target\ cell\ group})\times100\%$$

FIG. 1 shows the killing rate of the anti-Her2 bispecific antibodies against BT474 Her2+++ tumor cells. The ADCC-enhanced anti-Her2 bispecific antibodies (represented as 23C2 HER2-1 and 23C2 HER2-2 in FIG. 1) had better killing effects on BT474 tumor cells than the combination of trastuzumab and pertuzumab and than the anti-Her2 bispecific antibodies (Expi HER2-1 and Expi HER2-2) expressed by CHO-S cells; wherein the $EC_{50}$ of the combination of trastuzumab and pertuzumab (1:1) is 8.627 ng/mL, the $EC_{50}$ of Expi HER2-1 is 38.05 ng/mL, and the $EC_{50}$ of Expi HER2-2 is 35.17 ng/mL, so that the Expi HER2-2 is superior to Expi HER2-1; the $EC_{50}$ of the ADCC-enhanced 23C2 HER2-1 is 4.728 ng/mL, and the $EC_{50}$ of ADCC-enhanced 23C2 HER2-2 is 3.658 ng/mL, so that the ADCC-enhanced 23C2 HER2-2 is superior to 23C2 HER2-1.

Example 9

Killing of Her2 Positive Target Cell NCI-N87 by Anti-Her2 Bispecific Antibodies The killing effects of the anti-Her2 bispecific antibodies on target cells (NCI-N87 Her2++, source: the Cell Bank of Type Culture Collection Committee of the Chinese Academy of Sciences) were studied using NK cells provided by human PBMCs (peripheral blood mononuclear cells), and the in vitro activity of the anti-Her2 bispecific antibodies was assessed by $EC_{50}$ value.

The specific procedures are as follows: NCI-N87 cells were adjusted to a cell density of $3\times10^5$ cells/mL using 1640 medium containing 2% FBS (fetal bovine serum) and seeded in a 96-well cell culture plate (eppendorf, Cat. No. 0030730199) at 50 μL per well. Different concentrations of the anti-Her2 bispecific antibodies or control drugs (8.1 nM, 2.7 nM, 0.9 nM, 0.3 nM, 0.1 nM, 0.03 nM, 0.01 nM, 0.003 nM, 0.001 nM and 0.0004 nM) were prepared using medium for experiment and added to the above 96-well cell culture plate at 50 μL per well. Human PBMCs were adjusted to a cell density of $1.5\times10^6$ cells/mL using medium for experiment and added at 100 μL per well. An administration group (target cell+effector cell+antibody or control drug), a target cell group (NCI-N87 cell), an effector cell group (human PBMC), a target cell+effector cell group, a blank control group (medium) and a lysis solution control group, and a target cell maximum release group (target cell+lysis solution) were set, with the effector-to-target cell ratio being 10:1. 45 min prior to the assay, 20 μL/well of lysis solution (Promega, Cat. No. G182A) was added to the target cell maximum release group and the lysis solution control group. After 45 min, the cell lysis rates were measured using a CytoTox96® nonradioactive cytotoxicity assay (Promega, G1780). Trastuzumab, T-DM1 (trastuzumab-emtansine conjugate, under trade name Kadcyla®), the trastuzumab and pertuzumab (1:1), and Expi HER2-1 were used as the control drugs.

$$\text{Rate of lysis }(\%)=(OD_{administration\ group}-OD_{target\ cell+effector\ cell\ group})/(OD_{target\ cell\ maximum\ release\ group}-OD_{target\ cell\ group})\times 100\%$$

Figure 2:
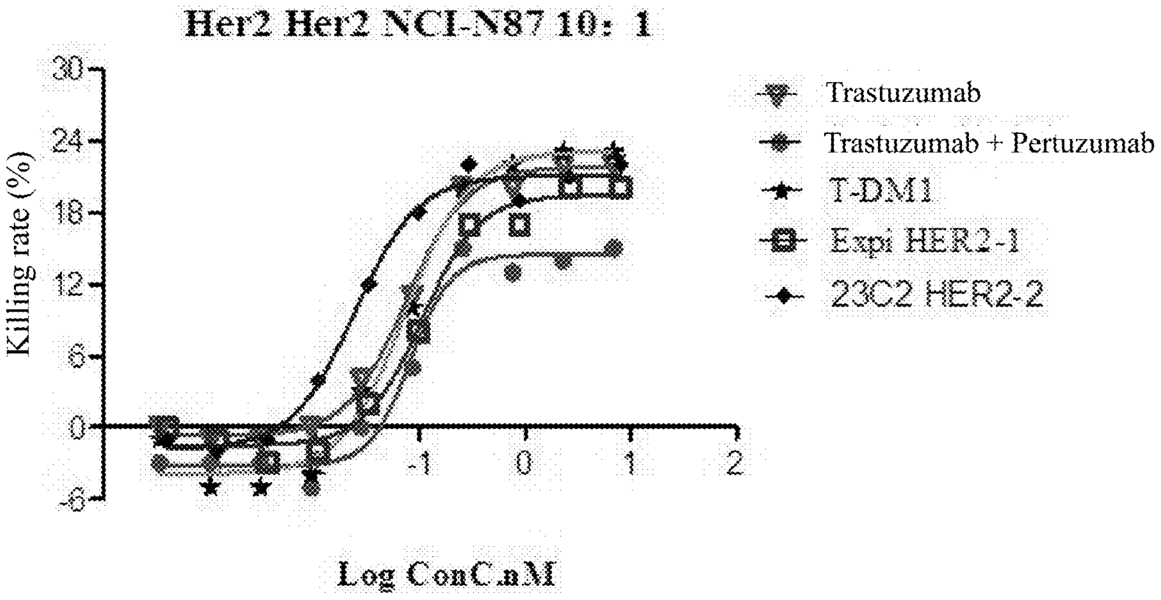
FIG. 2 shows the killing rates of anti-HER2 bispecific antibody, trastuzumab, T-DM1, and the combination of trastuzumab+pertuzumab against NCI-N87 tumor cells.

FIG. 2 shows the killing rate of anti-Her2 bispecific antibodies against NCI-N87 tumor cells. The ADCC-enhanced anti-Her2 bispecific antibody 23C2 HER2-2 had a better killing effect on NCI-N87 tumor cells than the combination of trastuzumab and pertuzumab, trastuzumab, T-DM1, and Expi HER2-1; wherein the EC 50 of the ADCC-enhanced 23C2 HER2-2 is 0.02447 nM, the EC 50 of the combination of trastuzumab and pertuzumab is 0.08267 nM, the $EC_{50}$ of Expi HER2-1 is 0.1048 nM, the $EC_{50}$ of T-DM1 is 0.07392 nM, and the $EC_{50}$ of trastuzumab is 0.07468 nM.

Example 10

Killing of Trastuzumab-Resistant Cell JIMT-1 by Anti-Her2 Bispecific Antibodies The killing effects of the anti-Her2 bispecific antibodies on target cells (JIMT-1, source: AddexBio, Cat. No. C0006005) were studied using NK cells provided by human PBMCs (peripheral blood mononuclear cells), and the in vitro activity of the anti-Her2 bispecific antibodies was assessed by $EC_{50}$ value.

The specific procedures are as follows: JIMT-1 cells were adjusted to a cell density of $3\times10^5$ cells/mL using 1640 medium containing 2% FBS (fetal bovine serum) and seeded in a 96-well cell culture plate (eppendorf, Cat. No. 0030730199) at 50 μL per well. Different concentrations of the anti-Her2 bispecific antibodies or control drugs (8.1 nM, 2.7 nM, 0.9 nM, 0.3 nM, 0.1 nM, 0.03 nM, 0.01 nM, 0.003 nM, 0.001 nM and 0.0004 nM) were prepared using medium for experiment and added to the above 96-well cell culture plate at 50 μL per well. Human PBMCs were adjusted to a cell density of $1.5\times10^6$ cells/mL using medium for experiment and added at 100 μL per well. An administration group (target cell+effector cell+antibody or control drug), a target cell group (JIMT-1BT474 cell), an effector cell group (human PBMC), a target cell+effector cell group, a blank control group (medium) and a lysis solution control group, and a target cell maximum release group (target cell+lysis solution) were set, with the effector-to-target cell ratio being 20:1. 45 min prior to the assay, 20 μL/well of lysis solution (Promega, Cat. No. G182A) was added to the target cell maximum release group and the lysis solution control group. After 45 min, the cell lysis rates were measured using a CytoTox96® nonradioactive cytotoxicity assay (Promega, G1780). Trastuzumab, T-DM1, the combination of trastuzumab and pertuzumab (1:1), and Expi HER2-1 were used as the control drugs.

$$\text{Rate of lysis }(\%)=(OD_{administration\ group}-OD_{target\ cell+effector\ cell\ group})/(OD_{target\ cell\ maximum\ release\ group}-OD_{target\ cell\ group})\times 100\%$$

Figure 3:
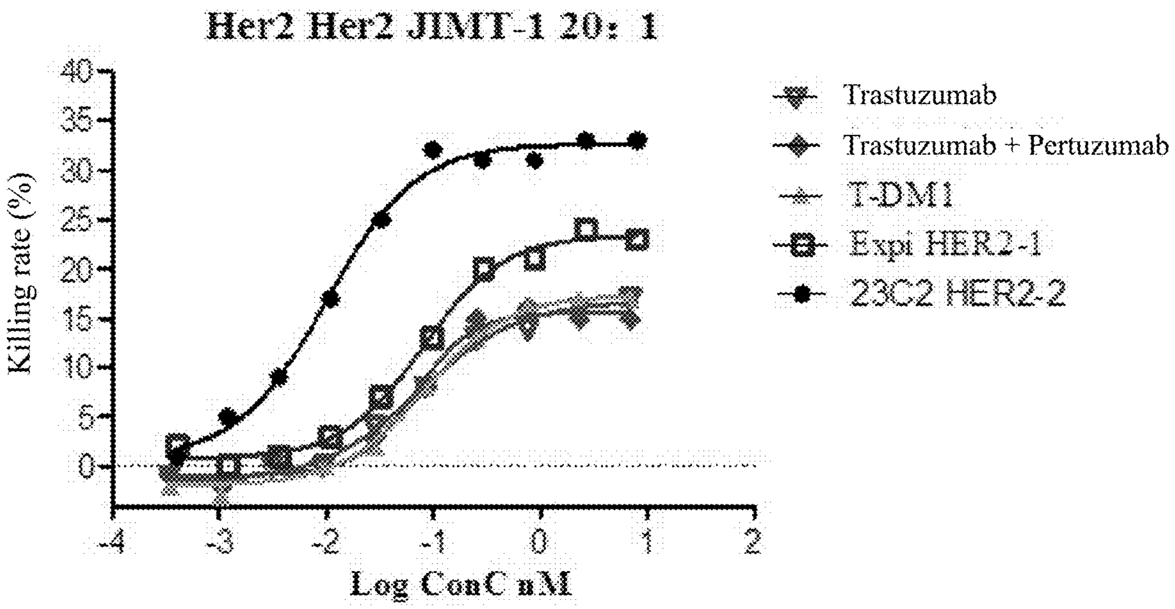
FIG. 3 shows the killing rates of anti-HER2 bispecific antibody, trastuzumab, T-DM1, and the combination of trastuzumab+pertuzumab against JIMT-1 tumor cells.

FIG. 3 shows the killing rate of the anti-Her2 bispecific antibodies against JIMT-1 tumor cells. The ADCC-enhanced anti-Her2 bispecific antibody 23C2 HER2-2 had a better killing effect on JIMT-1 tumor cells than the combination of trastuzumab and pertuzumab, trastuzumab, T-DM1, and Expi HER2-1; wherein the EC 50 of the ADCC-enhanced 23C2 HER2-2 is 0.01006 nM, the $EC_{50}$ of the combination of trastuzumab and pertuzumab is 0.06727 nM, the $EC_{50}$ of Expi HER2-1 is 0.08066 nM, the $EC_{50}$ of T-DM1 is 0.08357 nM, and the $EC_{50}$ of trastuzumab is 0.07443 nM; in addition, the anti-Her2 bispecific antibody 23C2 HER2-2 showed a higher cell lysis rate.

Example 11

Inhibition of Proliferation of BT474 Her2+++ Tumor Cells by Anti-Her2 Bispecific Antibodies 23C2 Her2-2, trastuzumab and pertuzumab were diluted with DMEM/F12 medium (GIBCO, Cat. No. 11330-032) containing 2% FBS (fetal bovine serum, manufacturer: GIBCO, Cat. No. 10099-141) to a final concentration of 3.2 μg/mL, and then serially diluted in a ratio of 1:1 until 9 concentrations (1.6 μg/mL, 0.8 μg/mL, 0.4 μg/mL, 0.2 μg/mL, 0.1 μg/mL, 0.05 μg/mL, 0.025 μg/mL, 0.0125 μg/mL and 0.00625 μg/mL) were obtained. BT474 Her2+++ cells growing at log phase were collected, adjusted to a density of $1\times10^5$ cells/mL, and plated at 100 μL per well, and a blank well without any cells was set as a control. The above serially diluted samples were added at 50 μL per well. The plate was incubated in an incubator at 37° C. with 5% $CO_2$ for 5 days. The culture medium was discarded, and CCK-8 (Dojindo, Japan, Cat. No. CK04) working solution was added at 100 μL per well. The plate was incubated for 4-5 h for color development and placed in a microplate reader (manufacturer: Thermo, Model: VarioskanFlash). The absorbance values at a wavelength of 450 nm were read and recorded using a reference wavelength of 630 nm. The proliferation inhibition rates against the tumor cells were calculated.

Figure 4:
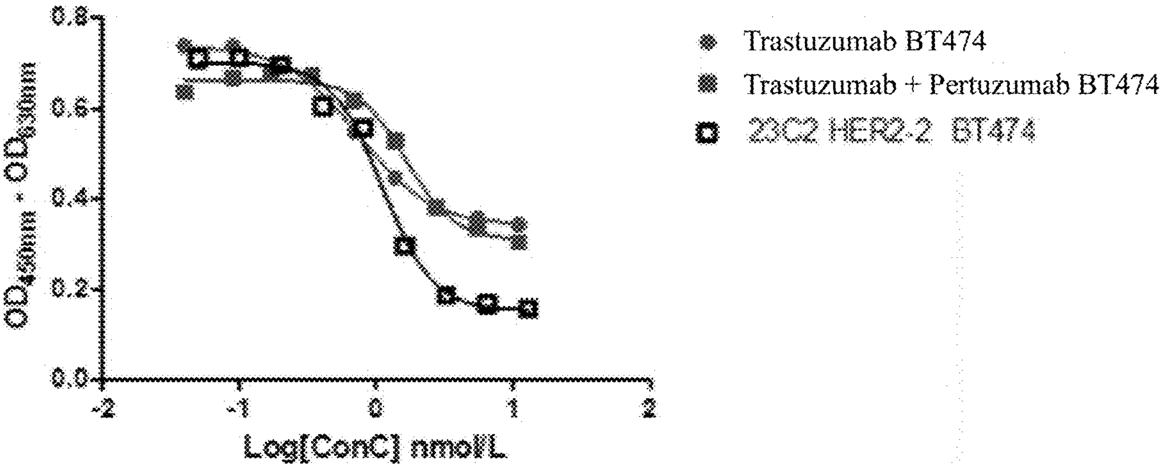
FIG. 4 shows the results of inhibition of anti-HER2 bispecific antibody, trastuzumab, and the combination of trastuzumab+pertuzumab on proliferation of BT474 tumor cells.

The results are shown in FIG. 4. The proliferation inhibition rate of the ADCC-enhanced anti-Her2 bispecific antibody 23C2 Her2-2 against BT474 tumor cells is 78.38%, which is better than that of trastuzumab (54.12%) and that of the combination of trastuzumab and pertuzumab (53.7%).

Example 12

Inhibition of NCI-N87 Her2++ Gastric Cancer Nude Mice Xenograft Tumor by Anti-Her2 Bispecific Antibodies The in vivo efficacy of the anti-Her2 bispecific antibodies was assessed in a mouse xenograft model using NCI-N87 Her2++ gastric cancer cells (the Cell Bank of Type Culture Collection Committee of the Chinese Academy of Sciences). NCI-N87 Her2++ gastric cancer cells were prepared at a concentration of $5\times10^7$ cells/mL and inoculated into nude mice (from Changzhou Cavens Laboratory Animal Ltd., 14-17 g, male, housed in an SPF environment) at the right side armpit at 0.1 mL/mouse.

The diameter of the nude mouse xenograft tumor was measured using a vernier caliper, and the animals were randomized into 5 groups when the tumors grew to 100-250 $mm^3$.

Group 1: control

Group 2: Expi Her2-1, 10 mg/kg

Group 3: 23C2 Her2-2, 5 mg/kg

Group 4: 23C2 Her2-2, 10 mg/kg

Group 5: Per+Tra (the combination of trastuzumab and pertuzumab), 5 mg/kg+5 mg/kg Each administration group was intravenously injected with a corresponding dose of the drug twice a week for about 3 consecutive weeks (6 injections). Each group was dosed at 10 mL/kg except that the two drugs in group 5 (the combination group) were each administered at 5 mL/kg. Group 1 was dosed i.v. with PBS (Hyclone; Cat. No. sh30256.01) at 10 mL/kg at the same time. In the combination group, trastuzumab was administered at least 30 min after pertuzumab was administered.

The anti-tumor effects of the test drugs were dynamically monitored by measuring the tumor volume.

The tumor volume was measured 2-3 times a week, and meanwhile the mice were weighed; the data were recorded. The general behavior of the mice was observed every day. Detection Index:

Tumor volume (TV), calculated as follows: TV=½×a×b$^2$, where a and b represent the length and width of the tumor, respectively.

Figure 6:
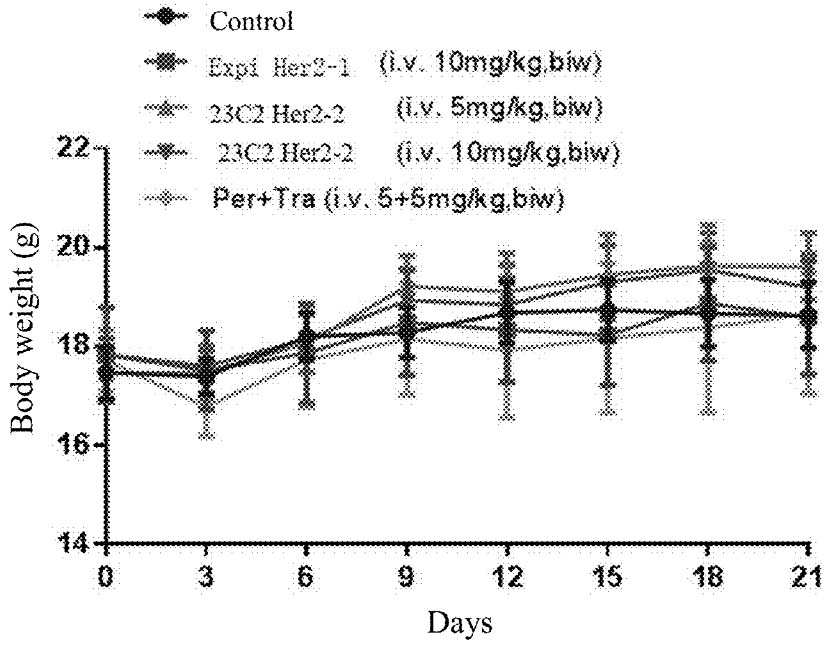
FIG. 6 shows the effect of anti-HER2 bispecific antibody, PBS vehicle control, and the combination of trastuzumab+pertuzumab on changes in mouse body weight in the gastric cancer N87 mouse xenograft tumor efficacy.
Figure 7:
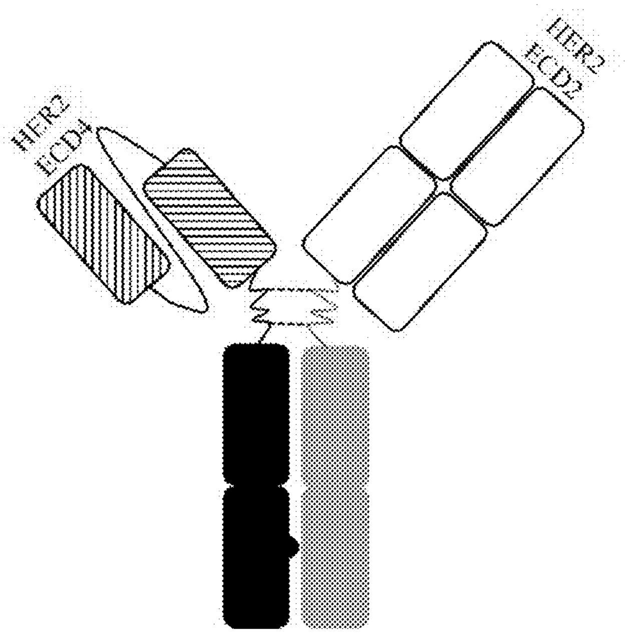
FIG. 7 shows a structure of some exemplary anti-HER2 bispecific antibodies, wherein a dimeric Fc is depicted with one chain shown in black (a first Fc polypeptide) and another chain shown in gray (a second Fc polypeptide), and one antigen-binding domain (a first antigen-binding fragment) is shown hatched and the other antigen-binding domain (a second antigen-binding fragment) is shown white; wherein the first antigen-binding fragment is an scFv and fused with the first Fc polypeptide, and the second antigen-binding fragment is an Fab and fused with the second Fc polypeptide.

In this experiment, administration was started on d0 and performed 6 times (on d0, d3, d7, d10, d14 and d17). By d21 of the experiment, no animals died. The mean body weight of the mice in each group showed an upward trend (FIG. 6). The drugs had no significantly toxic effect.

Figure 5:
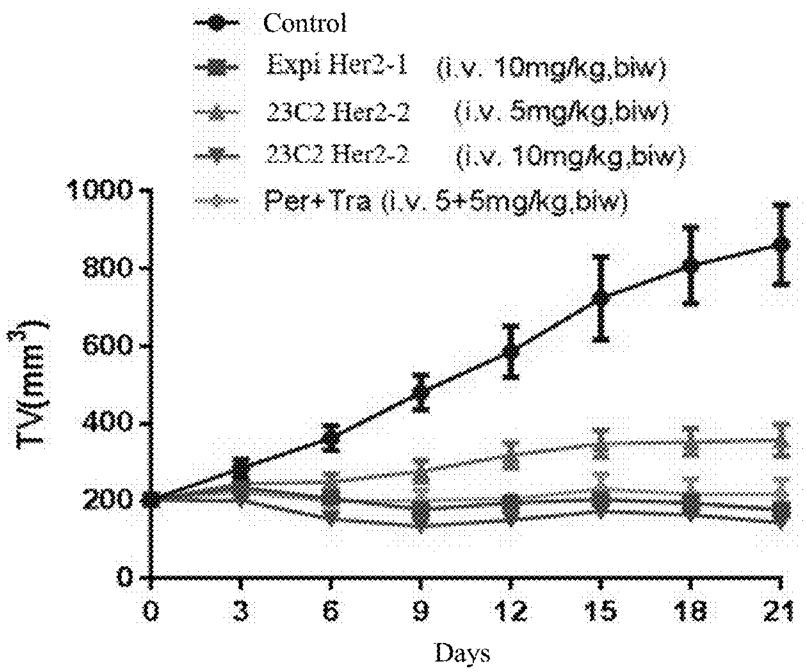
FIG. 5 shows the effect of anti-HER2 bispecific antibody, PBS vehicle control, and the combination of trastuzumab+pertuzumab (Per+Tra) on changes in mouse tumor volume in a gastric cancer N87 mouse xenograft tumor model.

By d21, the effect of each test sample of group 2 (10 mg/kg), group 3 (5 mg/kg), group 4 (10 mg/kg), and Per+Tra combination group (5 mg/kg+5 mg/kg) on the volume of NCI-N87 gastric cancer nude mouse xenograft tumor is shown in Table 8 and FIG. 5. 23C2 Her2-2 group (10 mg/kg) had a better inhibitory effect on the NCI-N87 gastric cancer nude mouse xenograft tumor than Expi Her2-1 (10 mg/kg) and the Per+Tra combination group (5 mg/kg+5 mg/kg).

TABLE 8

Effects of anti-HER2 bispecific antibodies on NCI-N87 gastric cancer nude mouse xenograft tumor volume (mean ± SD)

| Groups | Dose (mg/kg) | Route of administration | Number of animals (mice) d0 | Number of animals (mice) d21 | TV (mm$^3$) d0 | d3 | d6 | d9 | d12 | d15 | d18 | d21 |
|---|---|---|---|---|---|---|---|---|---|---|---|---|
| Control | — | i.v. | 6 | 6 | 204 ± 40 | 284 ± 58 | 363 ± 78 | 481 ± 109 | 586 ± 161 | 724 ± 261 | 808 ± 241 | 863 ± 251 |
| Expi Her2-1 | 10 | i.v. | 6 | 6 | 204 ± 23 | 235 ± 46 | 207 ± 35 | 179 ± 30 | 195 ± 24 | 204 ± 44 | 195 ± 50 | 178 ± 35 |
| 23C2 Her2-2 | 5 | i.v | 6 | 6 | 204 ± 31 | 246 ± 37 | 250 ± 47 | 277 ± 67 | 318 ± 79 | 348 ± 86 | 353 ± 84 | 358 ± 101 |
| 23C2 Her2-2 | 10 | i.v. | 6 | 6 | 204 ± 44 | 201 ± 39 | 154 ± 39 | 136 ± 33 | 151 ± 35 | 173 ± 46 | 165 ± 35 | 144 ± 29 |
| Per + Tra | 5 + 5 | i.v. | 6 | 6 | 204 ± 34 | 224 ± 48 | 199 ± 59 | 202 ± 65 | 205 ± 45 | 231 ± 93 | 218 ± 94 | 218 ± 91 |

Example 13

Synthesis of MC-GGFG-DXD

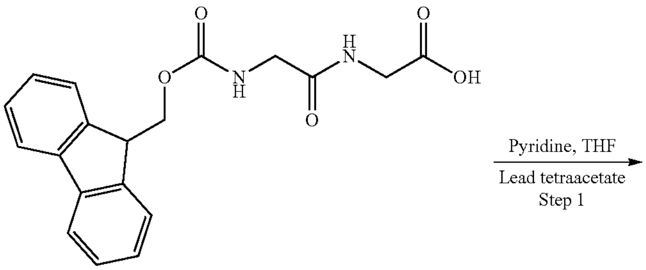

$SM_5$

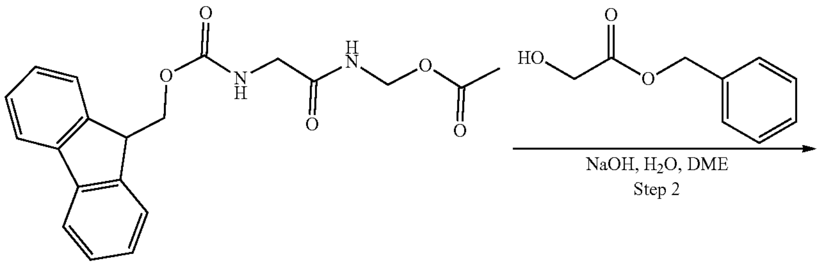

$A_5$

-continued
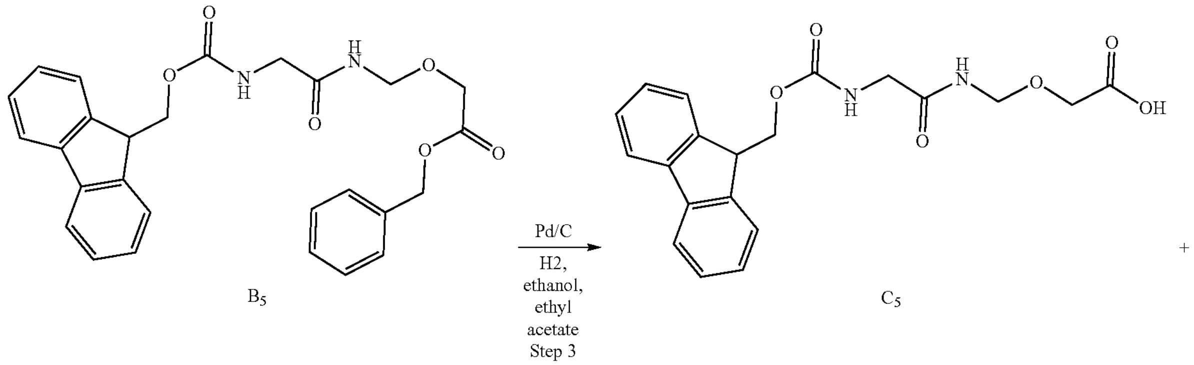
$B_5$ $C_5$
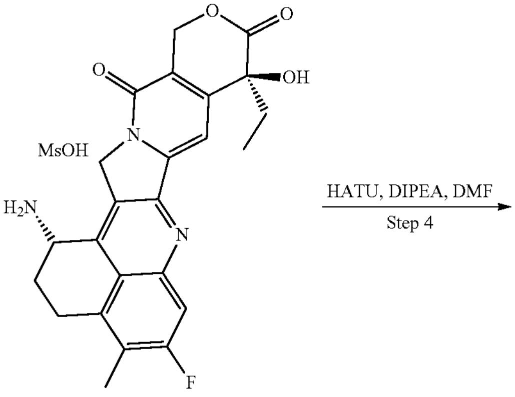
SM4
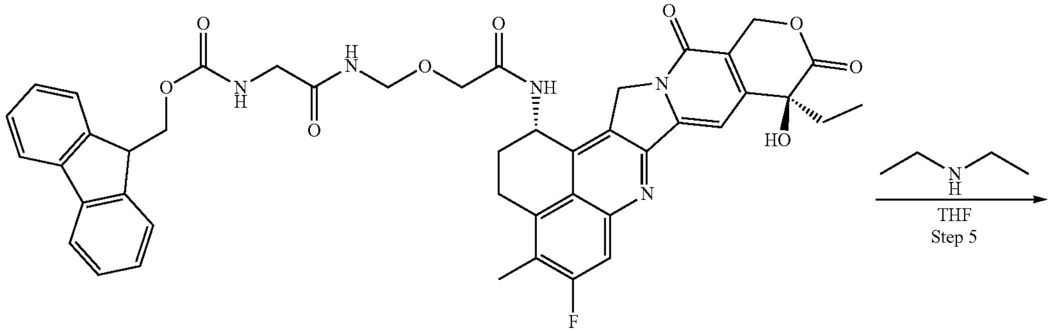
$D_5$
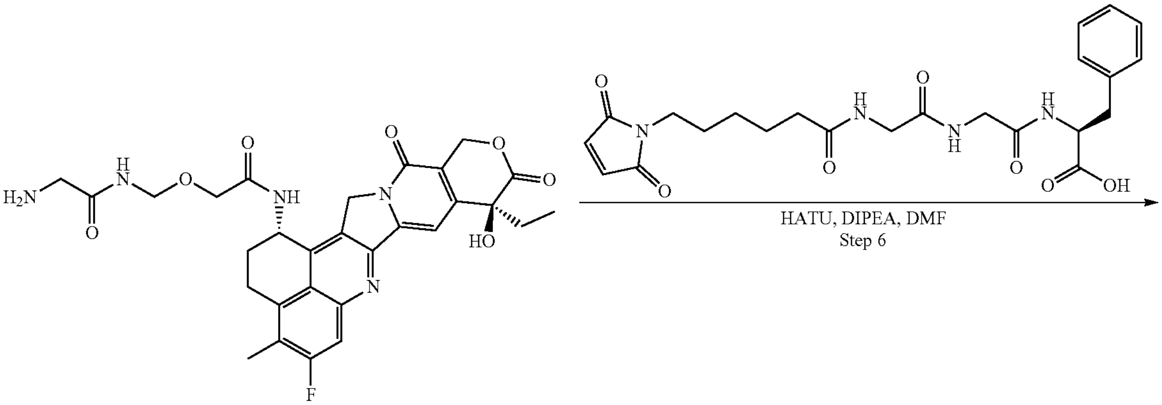
$E_5$ -continued

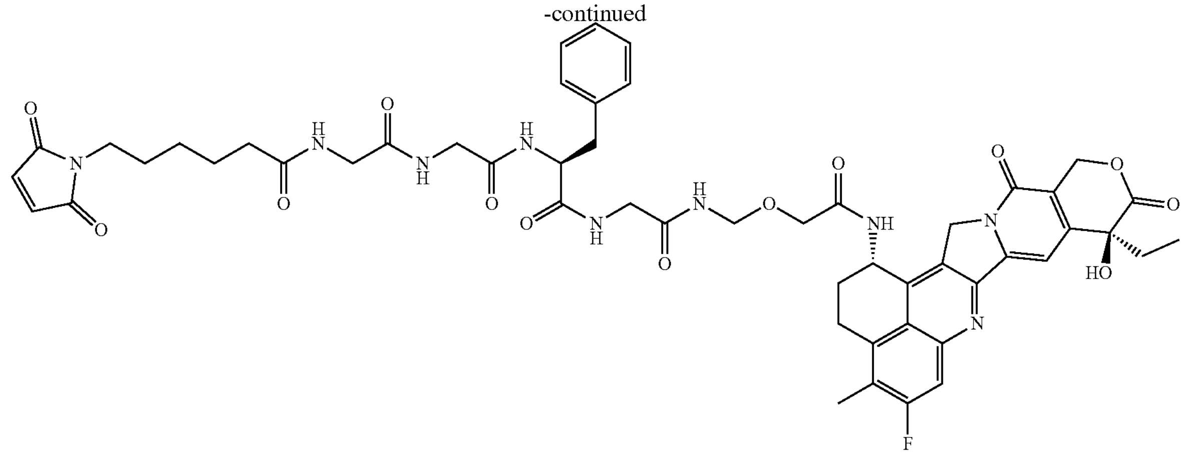

MC-GGFG-DXD

Step 1 Synthesis of A5 (({N-[(9H-fluoren-9-yl-methoxy)carbonyl]glycyl}amino) methyl acetate)

20 g of SM5 (N-[(9H-fluoren-9-ylmethoxy)carbonyl] glycylglycine) was weighed into a 1 L three-necked flask, 300 mL of tetrahydrofuran and 100 mL of toluene were added, and the mixture was stirred uniformly and then added with 30 g of lead tetraacetate and 5.4 g of pyridine. The mixture was heated to 65° C. and reacted for 4 h. The reaction solution was cooled to room temperature and the solid was filtered off. The organic phase was concentrated to dryness at 40° C. 300 mL of ethyl acetate and 300 mL of water were added to the concentrated dry organic phase. The organic phase was stirred for 20 min. The ethyl acetate phase was separated off. 100 mL of a saturated sodium chloride solution was added to the ethyl acetate phase, and the mixture was stirred for 20 min. The ethyl acetate phase was separated off and concentrated to dryness. The concentrate was subjected to silica gel column chromatography (petroleum ether:ethyl acetate=1:1) to obtain 13 g of A5. The yield was 63%. ESI-MS: m/z=391.1 $[M+Na]^+$.

Step 2 Synthesis of B5 ([({N-[(9H-fluoren-9-yl-methoxy)carbonyl]glycyl}amino)methoxy]benzyl acetate)

1.0 g of A5 was weighed into a 250 mL single neck flask, 15 mL of DME (ethylene glycol dimethyl ether) was added, 0.897 g benzyl glycolate was added, and the mixture was cooled to 0° C. in an ice-water bath. A solution was prepared from 0.27 mL of water and 0.108 g of NaOH. The prepared NaOH solution was added into the reaction solution. After 1 h of reaction at 0° C., 0.078 g of glacial acetic acid was added to the reaction solution. 100 mL of water and 100 mL of ethyl acetate were added, the mixture was stirred for 20 min at room temperature, and the organic phase was separated off and concentrated to dryness. The reaction solution was subjected to silica gel column chromatography (petroleum ether:ethyl acetate=1:1) to obtain 0.68 g of B5. The yield was 53%. ESI-MS: m/z=497.1 $[M+Na]^+$.

Step 3 Synthesis of C5 ([({N-[(9H-fluoren-9-yl-methoxy)carbonyl]glycyl}amino)methoxy]acetic acid)

0.68 g of B5 was weighed into a 250 mL hydrogenation flask, 20 mL of ethanol and 10 mL of ethyl acetate were added, and 0.34 g wet palladium on carbon (palladium content 10%) was added. The reaction solution was purged with hydrogen through the hydrogen balloon. The reaction system was reacted at room temperature for 1 h. The palladium on carbon was filtered off with celite. The filtrate was concentrated to dryness at 40° C. 425 mg of C5 was obtained. The yield was 77%. ESI-MS: m/z=407.1 $[M+Na]^+$.

Step 4 Synthesis of D5 ([({N-[(9H-fluoren-9-yl-methoxy)carbonyl]glycyl}amino)methoxy]acetyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6'7']indolizino[1,2-b]quinolin-1-yl]amino}-2-oxoethoxy)methyl]glycinamide)

50 mg of SM4 (exatecan mesylate) and 50 mg of C5 were weighed into a 100 mL single-neck flask, 2 mL of DMF (N,N-dimethylformamide) was added, the reaction system was cooled to 0° C., and 54 mg of HATU (2-(7-azabenzotriazol-1-yl)-N,N,N',N'-tetramethyluronium hexafluorophosphate) and 30 mg of DIEA (N,N-diisopropylethylamine) were added. The reaction system was warmed to room temperature. The reaction system was reacted at room temperature for 3 h. 100 mL of dichloromethane and 100 mL of water were added. The organic phase was stirred for 20 min. The organic phase was separated off and concentrated to dryness. The reaction solution was subjected to silica gel column chromatography (dichloromethane:methanol=10:1) to obtain 88 mg of D5. The yield was 84%. ESI-MS: m/z=802.4 $[M+H]^+$.

Step 5 Synthesis of E5 ({[(glycyl)amino] methoxy}acetyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6'7']indolizino [1,2-b]quinolin-1-yl]amino}-2-oxoethoxy)methyl] glycinamide)

78 mg of D5 was weighed into a 100 mL single-neck flask, 4 mL of tetrahydrofuran was added, the reaction system was cooled to 0° C. and 78 mg of ethylenediamine was added. The reaction system was warmed to room temperature. The reaction system was reacted for 5 h. The reaction solution was concentrated to dryness at 40° C. 55 mg of E5 was obtained. The yield was 98%. ESI-MS: m/z=580.3 $[M+H]^+$.

Step 6 Synthesis of MC-GGFG-DXD 55 mg of E5 was weighed into a 100 mg single-neck flask, 2 mL of N,N-dimethylformamide was added, 48 mg of MC-GGF-OH (maleimidocaproyl-glycyl-glycyl-phenylalanine) was added, and the reaction system was cooled to 0° C. 54 mg of HATU was added and 30 mg of DIEA was added. The reaction system was warmed to room temperature. The reaction system was reacted for 1 h. 100 mL of ethyl acetate and 100 mL of water were added thereto, and the mixture was stirred for 20 min. The organic phase was separated off. The organic phase was concentrated to dryness at 40° C. The reaction solution was subjected to silica gel column chromatography (ethyl acetate:methanol=10:1) to obtain 26 mg of MC-GGFG-DXD. The yield was 27%. ESI-MS: m/z=1034.51 ([M+H]$^+$). $^1$H-NMR (500 MHz, DMSO-$d_6$) 8.62 (1H, t, J=6.5 Hz), 8.50 (1H, d, J=9.0 Hz), 8.29 (1H, t, J=6.0 Hz), 8.12 (1H, d, J=8.0 Hz), 8.06 (1H, t, J=6.0 Hz), 8.00 (1H, t, J=6.0 Hz), 7.76 (1H, d, J=11 Hz), 7.30 (1H, s), 7.25~7.15 (5H, m), 6.90 (2H, s), 6.52 (1H, brs), 5.61~5.57 (1H, m), 5.42~5.40 (2H, m), 5.19~5.16 (2H, m), 4.64 (2H, d, J=7.0 Hz), 4.49~4.44 (1H, m), 4.05~4.01 (2H, m), 3.76~3.51 (6H, m), 3.37~3.32 (2H, m), 3.21~3.11 (2H, m), 3.02 (1H, dd, J=4.5, 14.0), 2.77 (1H, dd, J=9.5, 13.5), 2.37 (3H, s), 2.21~2.15 (2H, m), 2.09 (2H, t, J=7.5 Hz), 1.91~1.81 (2H, m), 1.49~1.42 (4H, m), 1.20~1.14 (2H, m), 0.87 (3H, t, J=6.5 Hz).

Example 14

Synthesis of Deuterated MC-GGFG-DXD (MC-GGFG-DDDXD), Deuterated DXD (DDDXD) and DXD

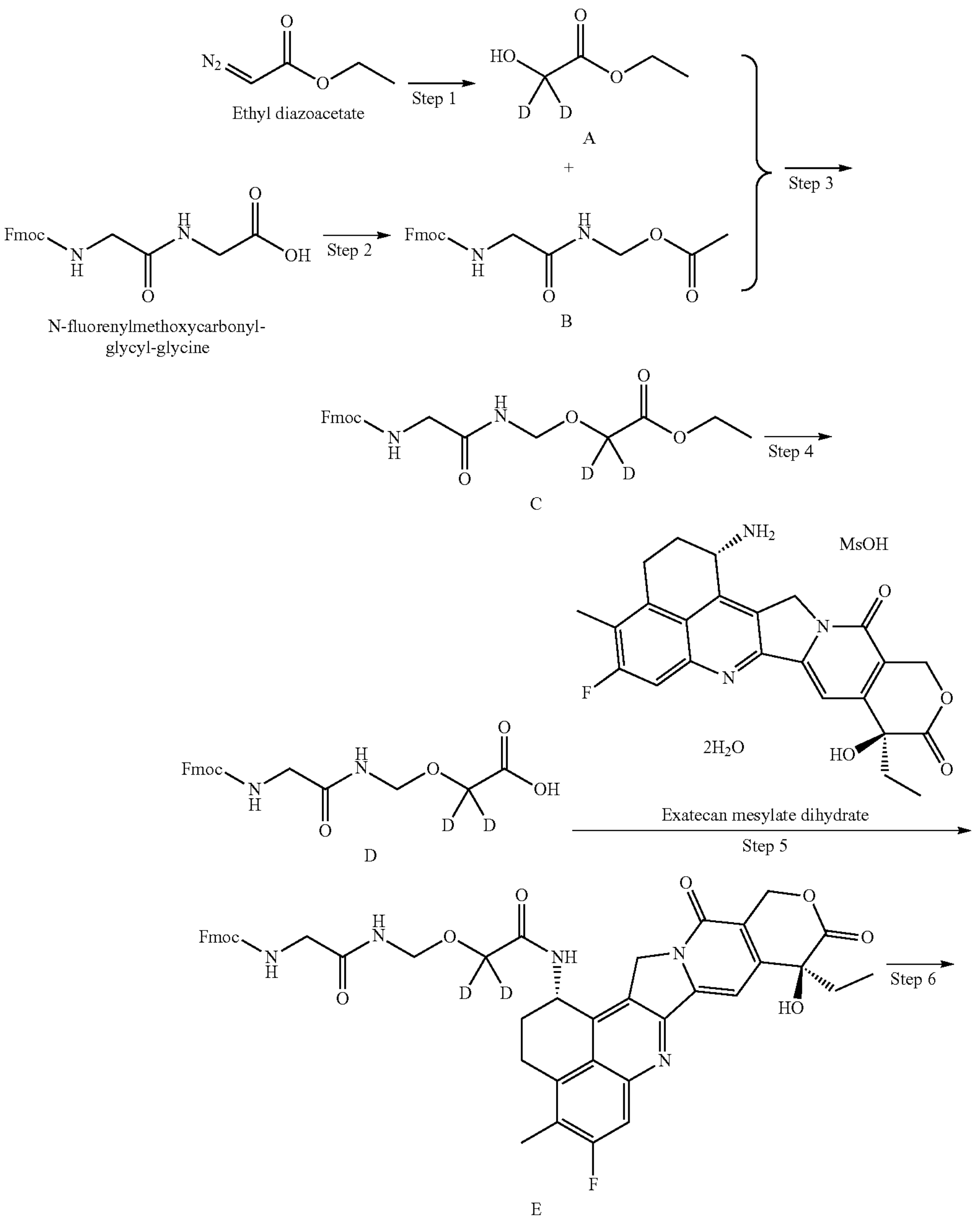

-continued

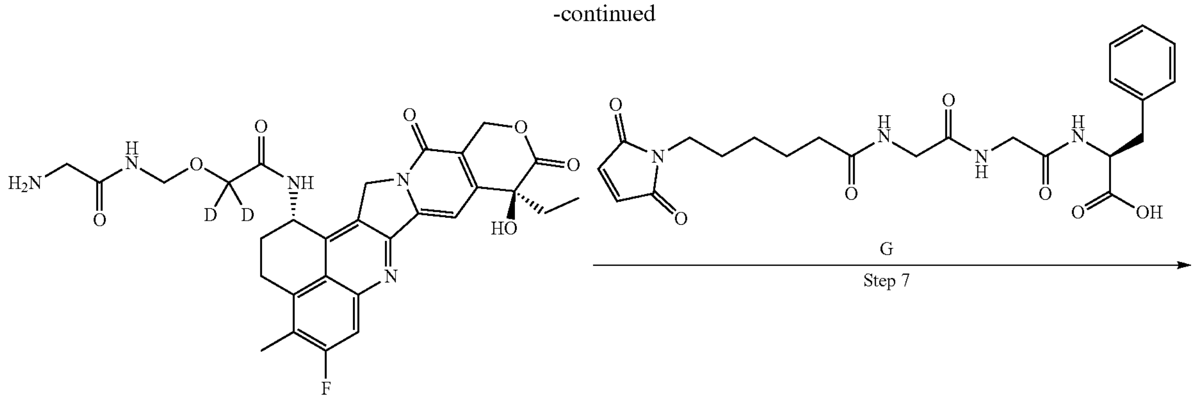

F

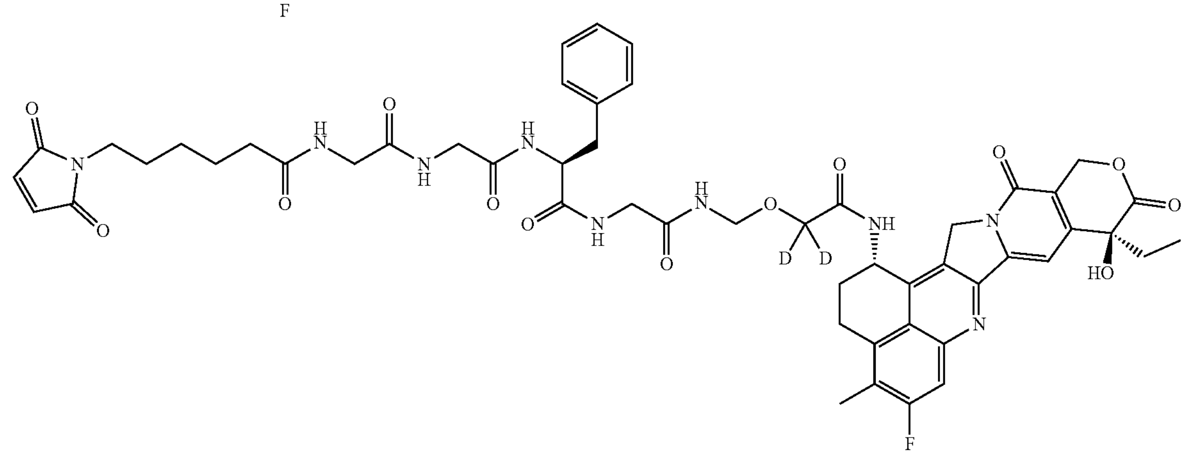

H
MC-GGFG-DDDXD

Step 1 Synthesis of Intermediate A 80 g of ethyl diazoacetate was placed in a 3 L single-neck flask under nitrogen atmosphere, and 800 mL of dichloromethane and 800 mL of a 1% deuterated acetic acid solution (8 g of deuterated acetic acid dissolved in 800 mL of deuterium water) were added. The reaction solution was stirred at room temperature for 75 h under a light-shielding condition. The organic phase was separated and collected, the aqueous phase was extracted 2 times with dichloromethane (200 mL×2), and the organic phases were combined. The organic phase was washed with 200 mL of deuterium water, the resulting organic phase was dried over anhydrous sodium sulfate, the sodium sulfate was removed by filtration, and the filtrate was concentrated to dryness under reduced pressure at 20° C. to obtain 49.25 g of intermediate A. The yield was 66%. $^{1}H$ NMR (500 MHz, $CDCl_3$) δ 4.27 (q, J=7.1 Hz, 1H), 1.31 (t, J=7.1 Hz, 2H).

Step 2 Synthesis of intermediate B 50 g of N-fluorenylmethoxycarbonyl-glycyl-glycine was weighed into a 2 L round-bottom flask, 750 mL of tetrahydrofuran and 150 mL of glacial acetic acid were added, the mixture was stirred at 40° C. for 20 min, 100 g of lead tetraacetate was added, and the reaction system was warmed to 80° C. and then reacted for 3 h. The reaction solution was cooled to room temperature and filtered under vacuum, and the filter cake was washed with 250 mL of ethyl acetate. The filtrate was concentrated to dryness. The filtrate was dissolved by adding 330 mL of dichloromethane and 670 mL of ethyl acetate to obtain organic phase. The organic phase was washed 3 times with 30% aqueous potassium bicarbonate (500 mL×3). The organic phase was dried over anhydrous sodium sulfate and filtered. The filtrate was concentrated to dryness under reduced pressure, and dissolved by adding 100 mL of dichloromethane; 100 mL of n-hexane was further added thereto, the mixture was stirred at room temperature until a solid was precipitated, and then 300 mL of a mixed solution of n-hexane and dichloromethane (n-hexane:dichloromethane=1:1) was added thereto and stirred overnight. The reaction solution was filtered, and the filter cake was dried in a vacuum oven at 40° C. for 4 h to obtain 37.3 g of intermediate B. The yield was 72%. LCMS (ESI) m/z: 391.09 $[M+Na]^+$.

Step 3 Synthesis of Intermediate C 78 g of intermediate B was weighed into a 3000 mL single-neck flask, 800 mL of dichloromethane was added thereto, and the mixture was added with 45 g of compound A. The 3000 mL single-neck flask was placed into an ice water bath, and the reaction system was cooled to 0° C. 16 g of lithium tert-butoxide was dissolved in 400 mL of dichloromethane to prepare a lithium tert-butoxide solution. The lithium tert-butoxide solution was added to a 3000 mL round-bottom flask. The reaction system was reacted at 0° C. for 3 h. The reaction solution was warmed to room temperature, added with 800 mL of water and stirred. The organic phase was separated and collected. The aqueous phase was extracted with 400 mL of dichloromethane. The organic phases were combined. The organic phase was washed with 800 mL of saturated brine for 1 time, dried over anhydrous sodium sulfate and filtered; the filtrate was concentrated under reduced pressure. The reaction solution was subjected to silica gel column chromatography (petroleum ether:ethyl acetate=3:1) to obtain 61 g of intermediate C. The yield was 70%. LCMS (ESI) m/z: 437.34 $[M+Na]^+$.

Step 4 Synthesis of Compound D 31.2 g of compound C was added to 270 mL of deuterated methanol and 70 mL of heavy water, and the mixture was stirred in an ice bath, followed by addition of 5.5 g of NaOH, and warmed to room temperature and stirred overnight. 300 mL of ethyl acetate and 300 mL of water were added to the reaction solution for extraction, and 20 mL of glacial acetic acid was added to the aqueous layer to adjust pH to 2-3; a solid precipitated out and filtered under vacuum to obtain 20.3 g of compound D. The yield was 69.8%. LCMS (ESI) m/z: 409.08 $[M+Na]^+$.

Step 5 Synthesis of Compound E 2.0 g of exatecan mesylate dihydrate and 1.63 g of compound D were weighed into a 100 mL round-bottom flask. 40 mL of N,N-dimethylformamide was added thereto, and the mixture was stirred. The reaction solution was cooled to 0° C. 2.0 g of 2-(7-azabenzotriazol-1-yl)-N,N,N',N'-tetramethyluronium hexafluorophosphate and 1.82 g of N,N-diisopropylethylamine were added successively thereto. The reaction system was reacted at 0° C. for 3 h. The reaction solution was poured into 120 mL of ice water. The reaction solution was stirred for 1 h and filtered. The filter cake was dissolved with dichloromethane. The reaction solution was subjected to column chromatography (100 g of 100-200 mesh silica gel, dichloromethane:methanol=30:1, 2 L) to obtain 2.6 g of compound E. The yield was 92%. LCMS (ESI) m/z: 804.84 $[M+H]^+$.

Step 6 Preparation of Compound F 0.38 g of 1,8-diazabicyclo[5.4.0]undec-7-ene was weighed into a 100 mL round-bottom flask. 20 mL of tetrahydrofuran was added to the round-bottom flask and the mixture was stirred. The reaction solution was cooled to 0° C. 2.0 g of compound E was weighed out and dissolved in 20 mL of tetrahydrofuran. The prepared solution of compound E was slowly added to a 100 mL round-bottom flask. The reaction system was naturally warmed to room temperature and reacted for 3 h. The reaction solution was filtered under nitrogen atmosphere. 1.45 g of compound F was obtained. The yield was 98%. LCMS (ESI) m/z: 582.39 $[M+H]^+$.

Step 7 Preparation of compound H 1.00 g of compound F and 0.97 g of compound G were weighed into a 100 mL round-bottom flask, and 10 mL of N,N-dimethylformamide was added thereto. The reaction solution was cooled to −20° C., and added with 0.34 g of 1-hydroxybenzotriazole and 0.49 g of 1-(3-dimethylaminopropyl)-3-ethylcarbodiimide hydrochloride. The reaction system was reacted at −20° C. for 3 h. 20 mL of DCM and 20 mL of water were added into the reaction solution, the mixture was stirred for 0.5 h and left standing for liquid separation, and the organic phase was collected. The organic phase was dried over anhydrous sodium sulfate and filtered. The filtrate was concentrated to dryness under reduced pressure. The reaction solution was subjected to silica gel column chromatography (dichloromethane:methanol=15:1) to obtain 400 mg of compound H. The yield was about 22%. MS m/s: 1037.08 $[M+H]^+$. H-NMR (500 MHz, DMSO-d6) 8.62 (1H, t, J=6.5), 8.49 (1H, d, J=8.5), 8.29 (1H, t, J=5.5), 8.12 (1H, d, J=8.0), 8.06 (1H, t, J=5.5), 8.00 (1H, t, J=5.5), 7.74 (1H, d, J=10.5), 7.30 (1H, s), 7.27~7.12 (5H, m), 6.98 (2H, s), 6.51 (1H, brs), 5.61~5.58 (1H, m), 5.45~5.37 (2H, m), 5.22~5.13 (2H, m), 4.64 (2H, d, J=6.5), 4.49~4.45 (1H, m), 3.76~3.57 (6H, m), 3.37~3.32 (2H, m), 3.24~3.09 (2H, m), 3.02 (1H, dd, J=4.5, 14.0), 2.77 (1H, dd, J=9.5, 13.5), 2.36 (3H, s), 2.23~2.14 (2H, m) 2.09 (2H, t, J=7.5), 1.91~1.79 (2H, m), 1.49~1.42 (4H, m), 1.20-1.14 (2H, m), 0.87 (3H, t, J=7.5).

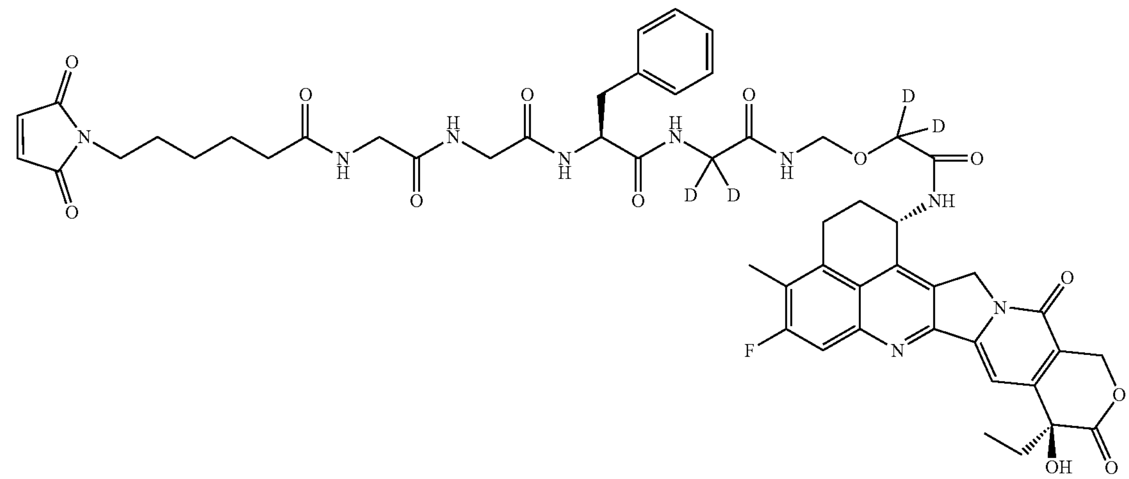

-continued

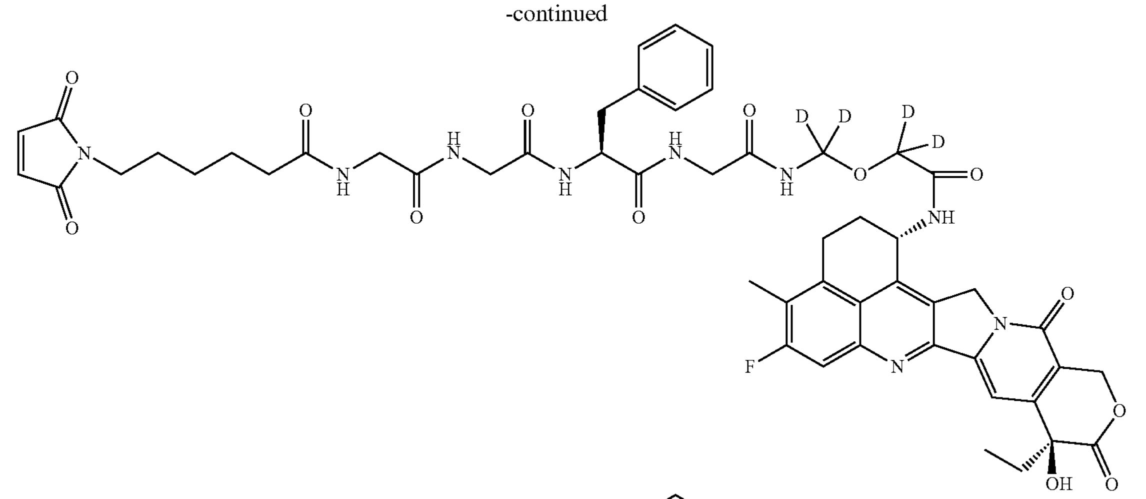

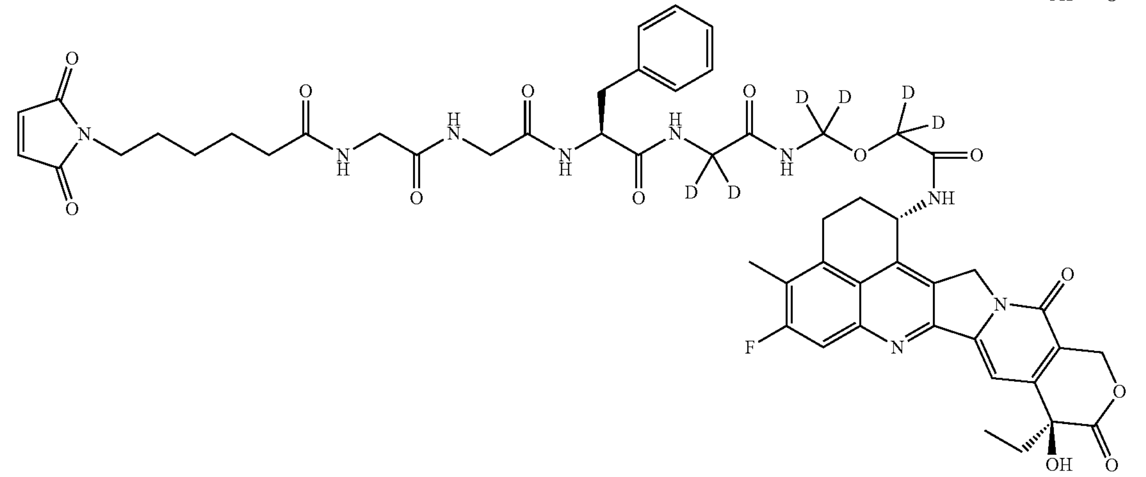

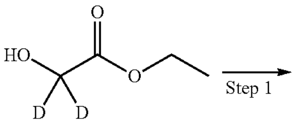

A

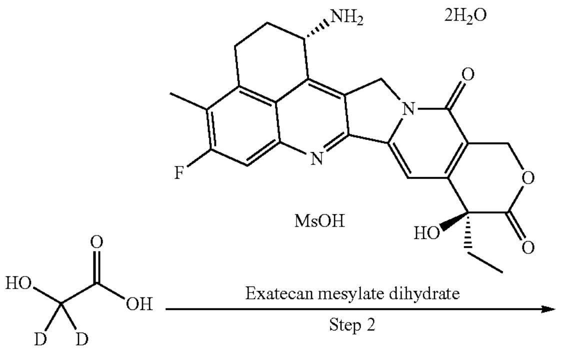

I

-continued

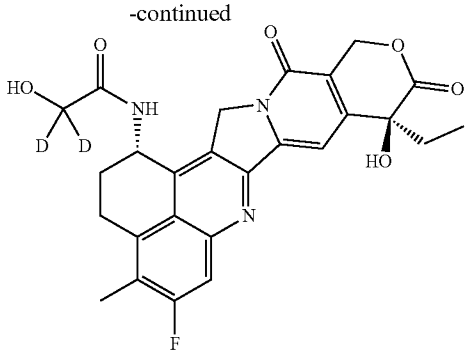

J
DDDXD

Step 1 Synthesis of Intermediate I 80 g of compound A was added to 9 mL of deuterated methanol and 1 mL of heavy water, and the mixture was stirred in an ice bath, followed by addition of 0.32 g of sodium hydroxide, and stirred at room temperature overnight. The reaction solution was concentrated under reduced pressure at 40° C. to obtain compound I, which was directly used in the next step without purification.

Step 2 Synthesis of compound J (DDDXD)

0.30 g of exatecan mesylate dihydrate and 0.056 g of intermediate I were added to 3 mL of N,N-dimethylformamide. The mixture was stirred in an ice bath, followed by addition of 0.32 g of 1H-benzotriazol-1-yl-oxytripyrrolidinyl hexafluorinephosphate and 0.22 g of N,N-diisopropylethylamine, and stirred at room temperature for 4 h. The reaction solution was subjected to liquid chromatography to prepare 0.18 g of compound J. The yield was 64.3%. LC-MS (ESI) m/z: 496.37 $[M+H]^+$. $^1$H-NMR (500 MHz, DMSO-$d_6$) 8.39 (d, J=8.9 Hz, 1H), 7.70 (d, J=10.9 Hz, 1H), 7.29 (s, 1H), 6.52 (s, 1H), (m, 1H), 5.47 (s, 1H), 5.40 (s, 2H), 5.17~5.02 (m, 2H), 3.24~3.03 (m, 2H), 2.34 (s, 3H), 2.25~2.09 (m, 2H), 1.92~1.80 (m, 2H), 0.87 (t, J=7.3 Hz, 3H).

In addition, DXD was prepared by reference to the method disclosed in Example 76 of the specification of Patent WO2014057687.

DXD

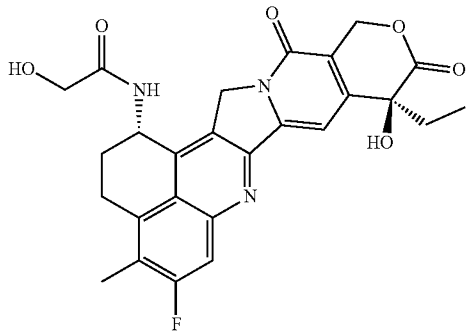

Example 15

Preparation of Antibody-Drug Conjugates

Reagents:

- Solution A: PBS buffer at pH 7.4
- Solution B: 10 mM aqueous TCEP (tris(2-carboxyethyl) phosphine hydrochloride)
- Solution C: DMSO (dimethyl sulfoxide)
- Solution D: histidine buffer (containing 0.89 mg/mL L-histidine and 4.04 mg/mL L-histidine hydrochloride monohydrate)
- Solution E: 700 mg/mL sucrose solution (formulated with solution D)
- Solution F: 20 mg/mL Tween 80 (formulated with solution D)
- Antibody: trastuzumab, 23C2 Her2-2
- Linker-payload (linker-cytotoxic drug moiety): MC-GGFG-DXD and MC-GGFG-DDDXD

TABLE 9

| Experimental conditions and groups: | |
|---|---|
| Antibody (N1):TCEP (N2) | Antibody (N1):compound (N3) |
| 1:6/1:6.6 | 1:11.6/1:9.6 |
| Serial number | Groups |
| 1 | Saturated conjugation of Trastuzumab to MC-GGFG-DXD (N1:N2 = 1:6, N1:N3 = 1:11.6) |
| 2 | Saturated conjugation of Trastuzumab to MC-GGFG-DDDXD (N1:N2 = 1:6, N1:N3 = 1:11.6) |
| 3 | Saturated conjugation of 23C2 Her2-2 to MC-GGFG-DXD (N1:N2 = 1:6.6, N1:N3 = 1:9.6) |
| 4 | Saturated conjugation of 23C2 Her2-2 to MC-GGFG-DDDXD (N1:N2 = 1:6.6, N1:N3 = 1:9.6) |

TABLE 9-continued

Procedures:

1. Antibody Replacement
   a. an ultrafiltration centrifuge tube with 30 KD was fully wet using the solution A;
   b. the antibody was replaced into solution A;
   c. an appropriate amount of solution A was added to adjust antibody concentration to 5 mg/mL (23C2 Her2-2) and 7.5 mg/mL (trastuzumab).
2. Antibody Reduction
   a. the molar weight of the antibody was calculated and recorded as N1;
   b. an appropriate amount of solution B was added into the antibody solution to ensure that the molar weight of TCEP in the reaction system was N2;
   c. the ultrafiltration centrifuge tube was wrapped with aluminum foil, placed on a rotary culture instrument and shaken at low speed (20 rpm) and reacted for 1 h at 37° C. in the dark.
3. Conjugation
   a. an appropriate amount of linker-payload was taken and dissolved in DMSO to adjust a final concentration to 10 mg/mL;
   b. DMSO was added into the antibody solution to make the antibody concentration be 5 wt %, and then the mixture was added with an appropriate amount of linker-payload solution to make the molar concentration be N3;
   c. the ultrafiltration centrifuge tube was wrapped with aluminum foil, placed on a rotary culture instrument and shaken at low speed (20 rpm) and reacted for 2 h at 20° C. in the dark.
4. Conjugation Termination
   a. an ultrafiltration centrifuge tube was wet by using the solution D;
   b. the antibody was replaced into the solution D, an appropriate amount of solutions E and F were added, and the concentration of sucrose and Tween 80 was adjusted to 90 mg/mL and 0.3 mg/mL, respectively, and the mixture was frozen and stored at −80° C.

Determination of DAR Value (Mean Number of Drug Linkages Per Molecule of Antibody) of Antibody-Drug Conjugates DAR values were determined by LC-MS method. 50 lug of the prepared ADC sample was added with 1 μL of glycosidase PNGaseF (RHINO BIO, China) and incubated at 37° C. for 20 h. The mass spectrometer used in the experiment was a high resolution Xevo G2-XS (Waters, USA). The concentration of the sample was adjusted to 5 μM, and mass spectrum data were collected in a positive ion mode by adopting a direct sampling method. The collected non-denaturing mass spectral data were analyzed and processed using the software UNIFI 1.8.2.169 (Waters, USA).

Determination of Protein Concentration of Antibody-Drug Conjugates

Protein concentration was detected by lowry method. Trastuzumab and 23C2 Her2-2 were used as standard substance. The absorbance values of the standard substance and the prepared ADC sample at OD650 wavelength were detected by using a microplate reader, a standard curve wad fitted, the absorbance value of the sample was substituted into the standard curve, and the protein concentration was calculated.

The following antibody-drug conjugates were prepared and assayed by the above method:
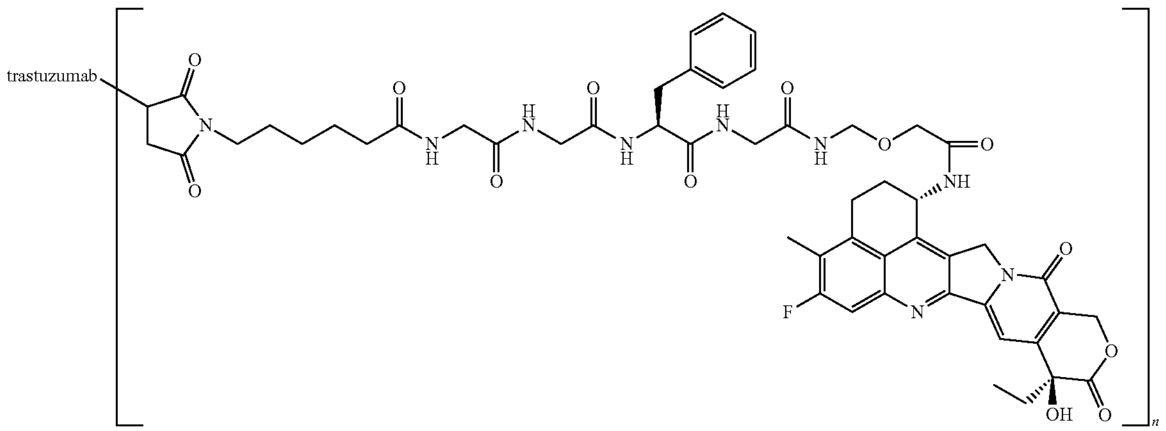
Trastuzumab-DXD, antibody concentration: 4.25 mg/mL, DAR: 7.6.
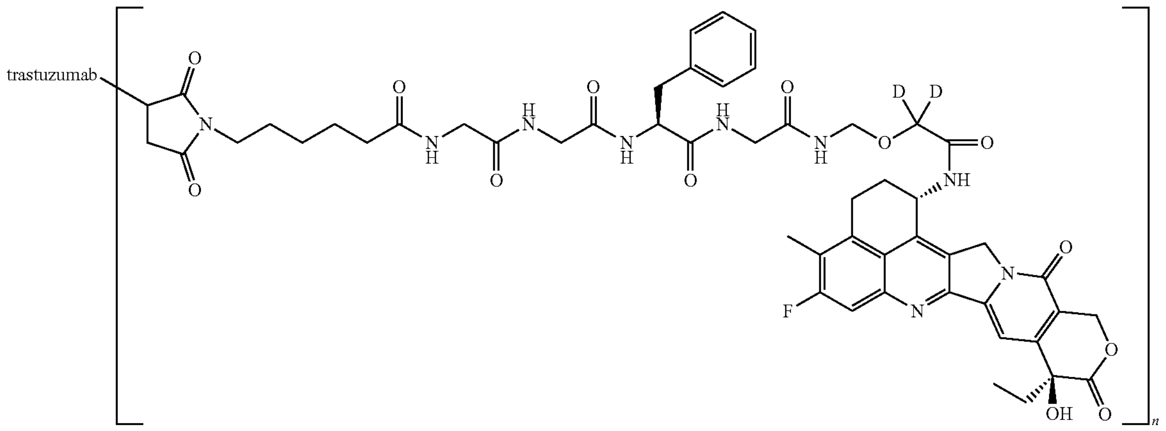
Trastuzumab-DDDXD, antibody concentration: 4.29 mg/mL, DAR: 7.7.
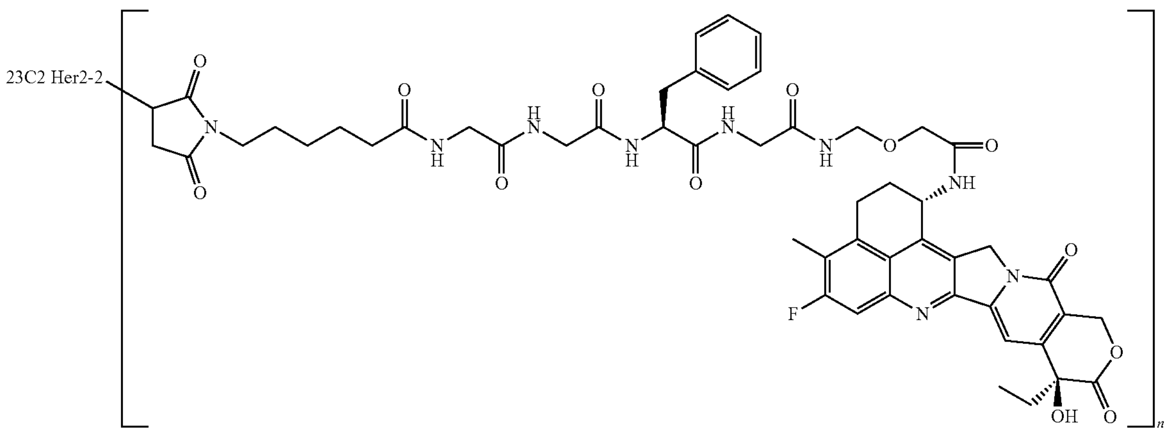

23C2 Her2-2-DXD, antibody concentration: 4.35 mg/mL, DAR: 5.7.

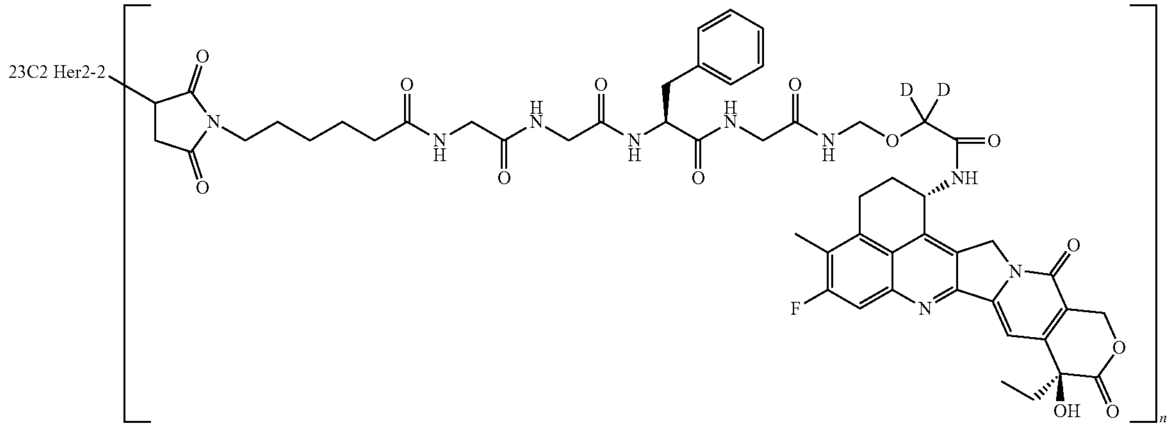

23C2 Her2-2-DDDXD, antibody concentration: 4.16 mg/mL, DAR: 5.8.

Example 16

In Vitro Enzymatic Activity of Deuterated DXD (DDDXD)

1. Reagent material preparation
   a. 1% agarose electrophoresis gel was formulated;
   b. gelred dye soaking solution was formulated and stored in the dark;
   c. a working solution of topoisomerase I was formulated by ultrapure water and buffer.
2. Sample formulation
   a. compound (DDDXD) was re-dissolved and diluted in DMSO (serially diluted 10-fold from the initial concentration of 200 μM to 5 concentrations).
3. Reaction system
   a. positive control: 15 μL of ultrapure water+2 μL of 10×DNA Topoismerasel Buffer+2 μL 0.1% BSA+1 μL pBR322DNA;
   b. negative control: 14 μL of ultrapure water+2 μL of 10×DNA Topoismerasel Buffer+2 μL of 0.1% BSA+1 μL of pBR322DNA+1 μL of topoisomerase I working solution;
   c. sample group: 12 laL of ultrapure water+2 μL of 10×DNA Topoismerasel Buffer+2 μL of 0.1% BSA+1 μL of pBR322DNA+1 μL of topoisomerase I working solution+2 μL of compound.
4. Procedures
   a. the above reaction system was placed in a water bath at 37° C. for 30 min;
   b. 2 μL of loading buffer was added into each tube system to terminate the reaction;
   c. agarose gel electrophoresis was performed for 1.5 h under the voltage of 2-2.5 V/cm;
   d. the gel after electrophoresis was stained with gelred dark bubbles for 1.5 h and photographed with a gel imager.

Example 17

Antigen Binding Assays of Antibody-Drug Conjugates

With reference to the method of Example 6, the measured affinities of Trastuzumab, 23C2 HER2-2, Trastuzumab-DDDXD and 23C2 HER2-2-DDDXD for HER2 protein are shown in Table 10 below:

| Sample | ka (1/Ms) | kd (1/s) | KD (M) |
|---|---|---|---|
| Trastuzumab | 1.23E+05 | 1.12E−04 | 9.16E−10 |
| 23C2 HER2-2 | 1.73E+05 | 6.06E−05 | 3.49E−10 |
| Trastuzumab-DDDXD | 1.28E+05 | 1.19E−04 | 9.25E−10 |
| 23C2 HER2-2-DDDXD | 1.28E+05 | 3.26E−05 | 2.55E−10 |

The results show that the anti-Her2 bispecific antibody had a stronger antigen binding activity compared with trastuzumab, and the anti-Her2 bispecific antibody ADC had a stronger antigen binding activity compared with trastuzumab ADC.

Example 18

Endocytosis Assay of Antibody-Drug Conjugates

The experimental method: 1 vial of cells in the logarithmic growth phase (NCI-N87 cells and SK-BR-3 cells) were collected, the cell density was adjusted to $2.5\times10^6$ cells/mL, and the cells were added to a 96-well plate at 20 μL/well. ADC samples Trastuzumab-DDDXD and 23C2 HER2-2-DDDXD prepared in Example 15 were pre-diluted to a concentration of 40)(g/mL and labeled as S1, and then subjected to 3-fold gradient dilution to obtain corresponding samples S1-S9. In addition, DS-8201, control IgG1 (a non-HER2 target-specific IgG1; Sino Biological, Cat No. HG1K), and DDDXD Conjugate IgG1-DDDXD were used as controls. The sample solution diluted in gradient and labeled endocytosis reagent (sartorius, 90564) were added to the cell plate at 20 μL/well and incubated at 37° C. for 15 min. The 96-well cell culture plate was taken and added with the two cells at 20 μL/well, and then the cell culture plate was incubated at 37° C. for 2 h. The 96-well cell culture plate was removed and placed in a flow cytometer to measure signal intensity.

Figure 8:
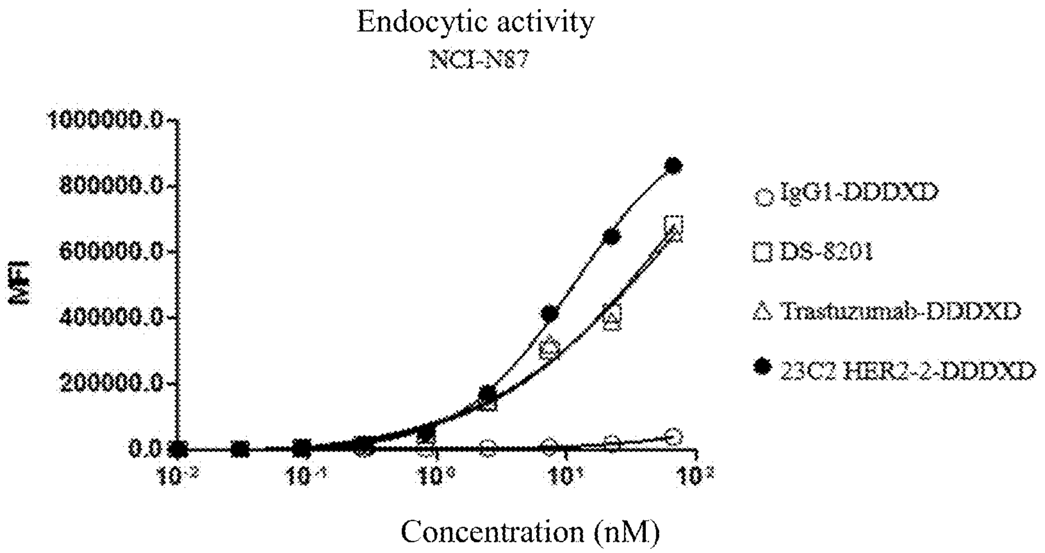
FIG. 8 shows the endocytic activity of drug conjugates of different antibodies (monoclonal antibody-DDDXD and bispecific antibody-DDDXD) in NCI-N87 tumor cells.
Figure 9:
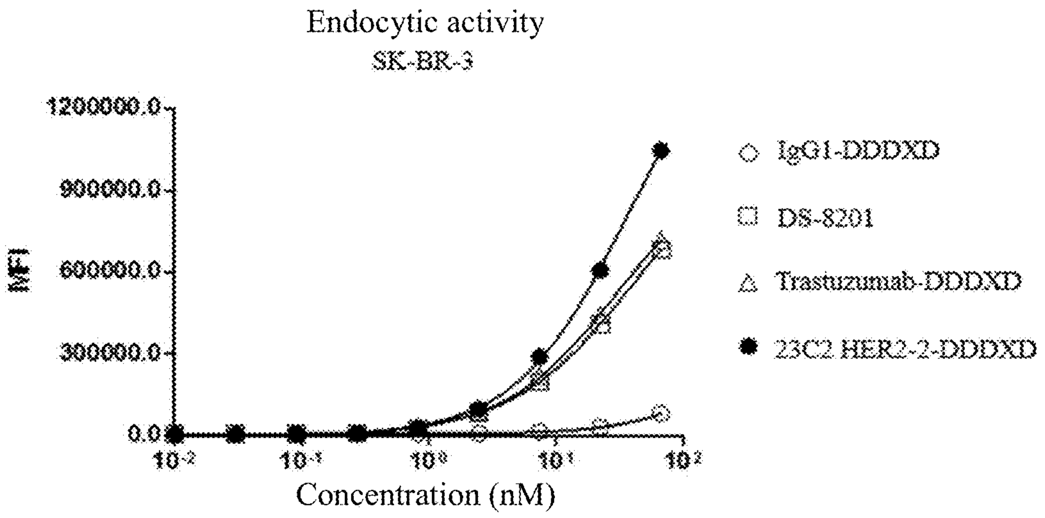
FIG. 9 shows the endocytic activity of drug conjugates of different antibodies (monoclonal antibody-DDDXD and bispecific antibody-DDDXD) in SK-BR-3 tumor cells.

Results of endocytosis experiments on NCI-N87 and SK-BR-3 two HER2 positive cells are shown in FIGS. 8 and 9, which show that the endocytosis of the anti-Her2 bispecific antibody ADC was stronger than that of the trastuzumab ADC.

Example 19

Cellular Activity of Deuterated DXD and Antibody-Drug Conjugates

DXD and DDDXD were pre-diluted to 140,000 ng/mL in culture medium and labeled as S1, and then five-fold serially diluted to obtain their corresponding reference samples S1-S9; the final drug concentration range was 35000 ng/mL to 0.0896 ng/mL with 9 concentrations in total. HER2 positive tumor cells NCI-N87 in the logarithmic growth phase were collected, adjusted to a density of $1\times10^5$ cells/mL, and plated at 100 μL per well, and a blank well without any cells was set as a control. The above serially diluted two samples were added at 50 μL per well. The plate was incubated in an incubator at 37° C. with 5% $CO_2$ for 5 days. The culture medium was discarded, and CCK-8 (Dojindo, Japan, Cat. No. CK04) working solution was added at 100 μL per well. The plate was incubated for 4-5 h for color developing and placed in a microplate reader (manufacturer: Thermo, Model: VarioskanFlash). The absorbance values at a wavelength of 450 nm were read and recorded using a reference wavelength of 630 nm. The proliferation inhibition against the tumor cells were calculated.

The results of the NCI-N87 cell experiment are shown in Table 11 below:

| Sample | $IC_{50}$ (nM) |
|---|---|
| DXD | 4.45 |
| DDDXD | 4.01 |

DDDXD showed stronger tumor cell proliferation inhibitory activity than DXD.

The antibody to be detected and the antibody-drug conjugate prepared in Example 15 were pre-diluted to 20)(g/mL by using a culture medium and labeled as S1, and then five-fold serially diluted to obtain their corresponding samples S1-S9. The final concentration range of the drug was 5000 ng/mL to 0.0128 ng/mL with 9 concentrations in total. The HER2 positive tumor cells (NCI-N87, BT474 and SK-BR-3) in the logarithmic growth phase were collected, each adjusted to a density of $2\times10^4$ cells/mL, and plated at 100 μL per well, and a blank well without any cells was set as a control. The serially diluted samples were added at 50 μL per well. The plate was incubated in an incubator at 37° C. with 5% $CO_2$. The culture medium was discarded, 100 μL of CTG detection medium (Promega, Cat. No. G7572) was added to each well, and the plate was incubated for 10 min for color developing and placed in a microplate reader (manufacturer Thermo, model: VarioskanFlash) to read the chemiluminescence value. The proliferation inhibition rates against the tumor cells were calculated.

The results of the NCI-N87 cell experiment are shown in Table 12 below:

| Sample | Inhibition rate % |
|---|---|
| Trastuzumab | 34.51 |
| Trastuzumab-DDDXD | 70.81 |
| 23C2 HER2-2 | 75.73 |
| 23C2 HER2-2-DDDXD | 90.08 |

The results of the BT474 cell experiment are shown in Table 13 below:

| Sample | Inhibition rate % |
|---|---|
| Trastuzumab | 67.91 |
| Trastuzumab-DDDXD | 47.82 |
| 23C2 HER2-2 | 75.56 |
| 23C2 HER2-2-DDDXD | 73.76 |

The results of the SK-BR-3 cell experiments are shown in Table 14 below:

| Sample | Inhibition rate % |
|---|---|
| Trastuzumab | 20.36 |
| Trastuzumab-DDDXD | 67.15 |
| 23C2 HER2-2 | 62.89 |
| 23C2 HER2-2-DDDXD | 75.56 |

It can be seen from the above results that the cell killing ability of the anti-Her2 bispecific antibody ADC was better than that of trastuzumab ADC.

Example 20

In Vitro Stability Assay in Liver Microsome

Each incubation system contained phosphate buffered saline (PBS, pH 7.4), liver microsomal protein, substrate (acetonitrile solution of the sample to be tested) and NADPH, and incubation was performed in a 37° C. water bath, and the reaction was terminated by adding the same volume of ice-cold acetonitrile after 0, 5, 15, 30 and 60 min. Negative controls were incubated with heat-inactivated liver microsomes of the corresponding species. The remaining content of the original substrate was detected by LC/MS/MS method.

Example 21

In Vivo Pharmacokinetic Experiments of Antibody-Drug Conjugates

The in vivo metabolic pathways and pharmacokinetic parameters of the antibody-drug conjugate of the present application were determined by reference to the methods described in Yoko Nagai, et al., Comprehensive Preclinical Pharmacokinetic Evaluations of Trastuzumab Deruxtecan (DS-8201a), an HER2-targeting antibody-drug conjugate, in Cynomolgus Monkeys, *Xenobiotica,* 2019, 49(9), 1086-1096.

Example 22

Inhibitory Effect of Antibody-Drug Conjugates on JIMT-1 Her2 Positive Breast Cancer Nude Mouse Xenograft Tumor JIMT-1 breast cancer cells were prepared at a concentration of $2\times10^7$ mL×0.1 mL/mouse, and inoculated under aseptic conditions into the right side armpit of nude mice. Animals were randomly divided into 3 groups after subcutaneous xenograft tumor inoculation until the tumor volume was around 100-300 $mm^3$: model group: solvent (comprising L-histidine 0.89 mg/mL, L-histidine hydrochloride 4.04 mg/mL, polysorbate 80 0.3 mg/mL, sucrose 90 mg/mL), 6 animals; 23C2 Her2-2-DXD group: 1.68 mg/kg, qw, i.v. 6 animals; 23C2 Her2-2-DDDXD group: 1.59 mg/kg, qw, i.v. 6 animals. Measuring the tumor volume 2-3 times per week, weighing the mouse, and recording data; animal performance was observed daily.

The relative weight (RWt) was calculated using the following formula:

$$RWC(\%) = \frac{w_t}{w_{t0}} \times 100\% - 100\%$$

wherein $Wt_0$ is the animal body weight at the time of cage administration (i.e., d0) and Wt is the animal body weight at each measurement.

The tumor growth inhibition (TGI) was calculated using the following formula:

$$TGI(\%) = \left(1\frac{TW}{TW_0}\right) \times 100\%$$

wherein TW is the tumor weight of administration group and $TW_0$ is the tumor weight of model group.

The body weights are shown in Table 15 below:

| Groups | Dosage mg/kg | Frequency of administration | Route of administration | Number of animals d0 | d24 | Relative body weight change (%) Mean ± SD d6 | d12 | d18 | d24 |
|---|---|---|---|---|---|---|---|---|---|
| Model group | — | qw | i.v. | 6 | 6 | 5.8 ± 3.1 | 9.1 ± 3.9 | 9.6 ± 3.8 | 15.8 ± 5.4 |
| 23C2 Her2-2-DXD | 1.68 | qw | i.v. | 6 | 6 | 6.7 ± 6.6 | 9.9 ± 5.6 | 10.2 ± 4.3 | 14.5 ± 4.7 |
| 23C2 Her2-2-DDDXD | 1.59 | qw | i.v. | 6 | 6 | 8.8 ± 3.5 | 11.5 ± 5.0 | 12.4 ± 2.9 | 15.0 ± 5.4 |

The drug effect is shown in Table 16 below:

| Groups | Dosage mg/kg | Frequency of administration | Route of administration | Number of animals d0 | d24 | Tumor weight Mean ± SD | TGI (%) |
|---|---|---|---|---|---|---|---|
| Model group | — | qw | i.v. | 6 | 6 | 0.594 ± 0.166 | — |
| 23C2 Her2-2-DXD | 1.68 | qw | i.v. | 6 | 6 | 0.189 ± 0.072 | 68.2% |
| 23C2 Her2-2-DDDXD | 1.59 | qw | i.v. | 6 | 6 | 0.145 ± 0.056 | 75.6% |

The results show that: the 23C2 Her2-2-DXD and 23C2 Her2-2-DDDXD had significant drug effects on a JIMT-1 mouse xenograft tumor model of human breast cancer cells, and the 23C2 Her2-2-DDDXD had stronger tumor inhibition effect compared with the 23C2 Her2-2-DXD.

According to the content disclosed in the present application, the methods of the present application have been described in terms of preferred embodiments. However, it will be apparent to those skilled in the art that changes and recombinations may be applied to the products, elements, methods and the steps or the sequence of steps of the methods described herein without departing from the concept, spirit and scope of the present application.

All patents, patent applications and other publications are explicitly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates or the content of these documents. Moreover, in any country or region, any reference to these publications herein is not to be construed as an admission that the publications form part of the commonly recognized knowledge in the art. The disclosed contents of all documents cited herein are hereby incorporated by reference to the extent that they provide exemplary, procedural and other details supplementary to those described herein.

The invention claimed is:

1. An antibody-drug conjugate of general formula Ab-(L-U) n, wherein Ab represents an antibody moiety, L represents a linker moiety, U represents a cytotoxic drug moiety, and wherein the antibody-drug conjugate has a structure of formula VII below:

VII

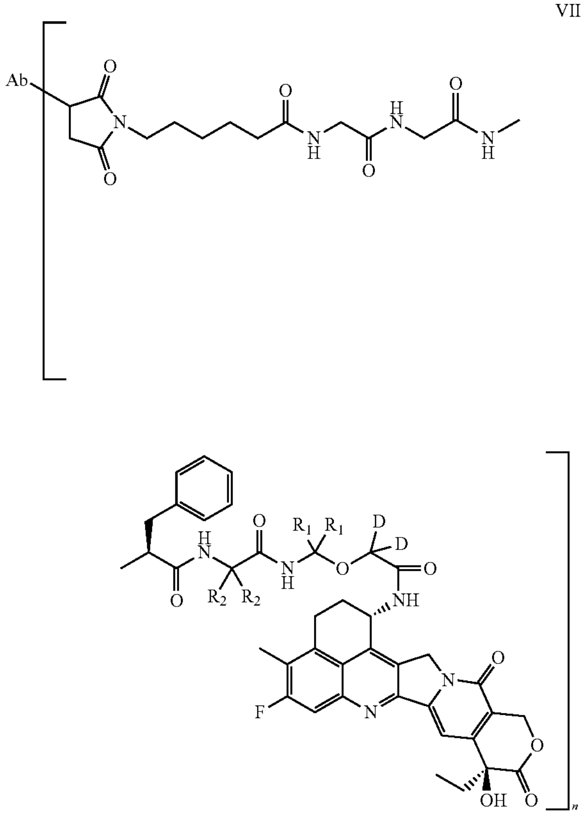

wherein the Ab represents an antibody moiety comprising a first antigen-binding fragment that binds to ECD4 epitope of HER2 and a second antigen-binding fragment that binds to ECD2 epitope of HER2, wherein the first antigen-binding fragment is an scFv and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 43, 28 and 29, respectively, and the light chain CDR1, the light chain CDR2 and the light chain CDR3 comprising amino acid sequences set forth in SEQ ID NOs: 30, 31 and 32, respectively, the second antigen-binding fragment is an Fab and comprises a heavy chain CDR1, a heavy chain CDR2, a heavy chain CDR3, a light chain CDR1, a light chain CDR2 and a light chain CDR3, the heavy chain CDR1, the heavy chain CDR2 and the heavy chain CDR3 comprising amino acid sequences set forth in SEQ ID NOs: 45, 46 and 47, respectively, and the light chain CDR1, the light chain CDR2 and the light chain CDR3 comprising amino acid sequences set forth in SEQ ID NOs: 48, 49 and 50, respectively, n is an integer or a decimal selected from the group consisting of 1 to 10, and $R_1$ and $R_2$ are each independently selected from the group consisting of hydrogen (H) and deuterium (D).

2. The antibody-drug conjugate according to claim 1, wherein the first antigen-binding fragment comprises a heavy chain variable region and a light chain variable region, the heavy chain variable region comprising amino acid sequence set forth in SEQ ID No: 35, and the light chain variable region comprising amino acid sequence set forth in SEQ ID No: 36.

3. The antibody-drug conjugate according to claim 2, wherein a VH and VL of the first antigen-binding fragment is arranged from N-terminus to C-terminus in the following order: VH-linker-VL.

4. The antibody-drug conjugate according to claim 1, wherein the second antigen-binding fragment comprises a heavy chain variable region and a light chain variable region comprising amino acid sequences set forth in SEQ ID NOs: 37 and 38, respectively.

5. The antibody-drug conjugate according to claim 1, wherein the antibody moiety Ab comprises an immunoglobulin functional domain operably linked to the first antigen-binding fragment and/or the second antigen-binding fragment, the immunoglobulin functional domain comprising: i. one or more of CL, CH1, CH2 or CH3, or ii. an Fc.

6. The antibody-drug conjugate according to claim 5, wherein the CL, CH1, CH2, CH3 and Fc are derived from CL, CH1, CH2, CH3 and Fc of human IgG, respectively;

the CL, CH1, CH2, CH3 or Fc has a modification or does not have a modification.

7. The antibody-drug conjugate according to claim 5, wherein the Fc is a dimeric Fc comprising a first Fc polypeptide and a second Fc polypeptide, the first antigen-binding fragment is operably linked to the first Fc polypeptide, and the second antigen-binding fragment is operably linked to the second Fc polypeptide.

8. The antibody-drug conjugate according to claim 1, wherein the antibody moiety Ab is a bivalent bispecific antibody, comprising: a heavy chain set forth in SEQ ID NO: 11, a heavy chain set forth in SEQ ID NO: 13, and a light chain set forth in SEQ ID NO: 15.

9. The antibody-drug conjugate according to claim 1, wherein the formula VII is of a structure of VII-1, VII 2, VII 3, or VII-4 below:

VII-1

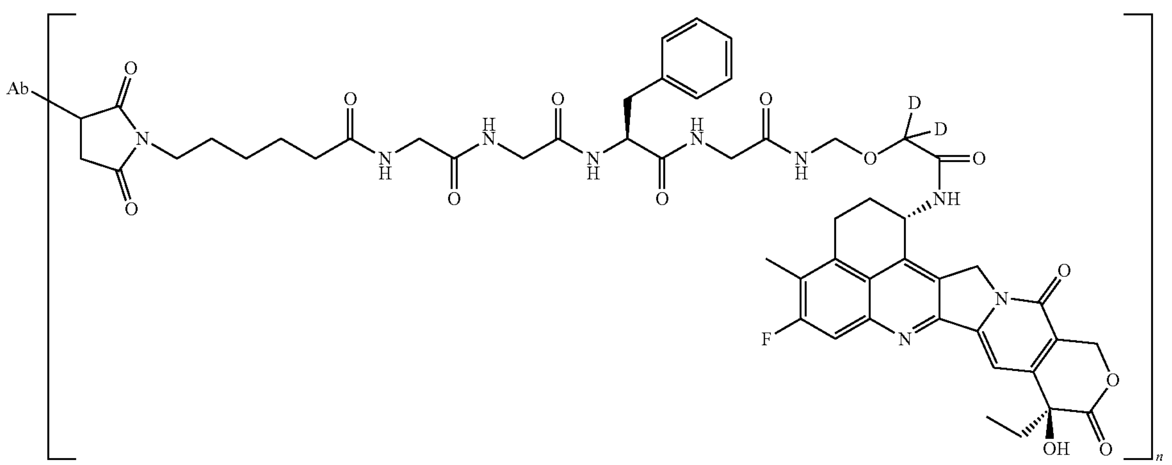

VII-2

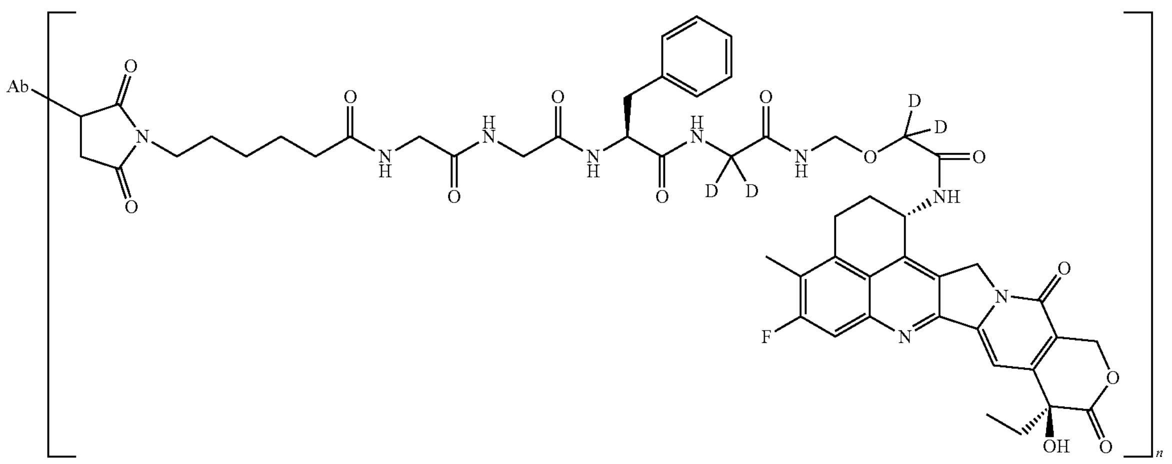

-continued

VII-3

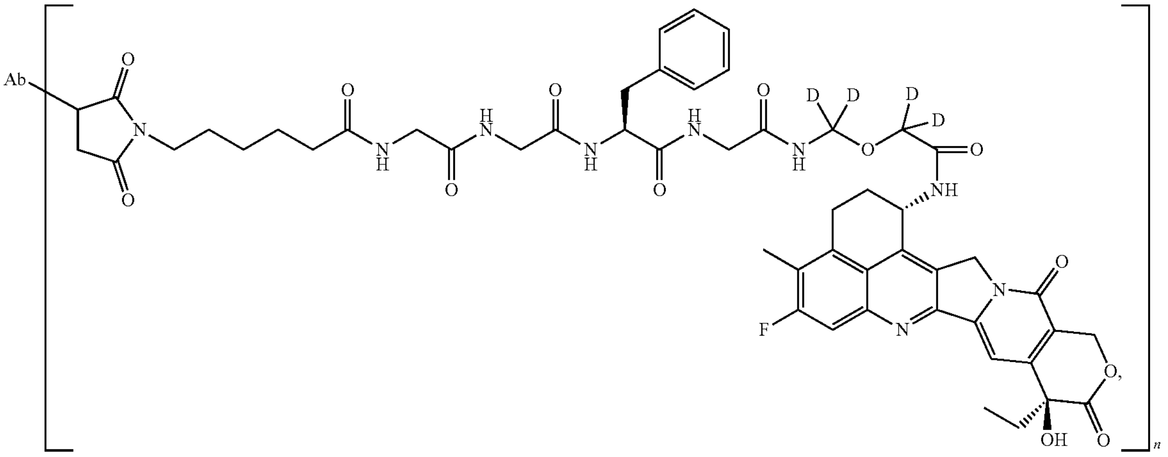

or

VII-4

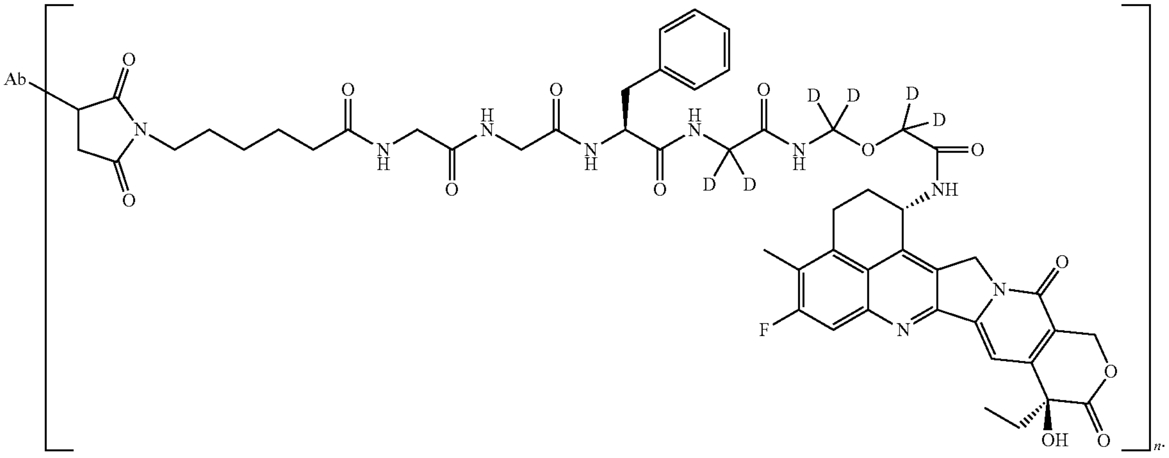

10. A method of treating cancer, comprising administering to a patient in need thereof a therapeutically effective amount of the antibody-drug conjugate according to claim 1, or a pharmaceutical composition comprising the antibody-drug conjugate and a pharmaceutically acceptable carrier.

11. The method according to claim 10, wherein the cancer is HER2 positive cancer.

12. A pharmaceutical composition comprising the antibody-drug conjugate according to claim 1, and a pharmaceutically acceptable carrier.

* * * * *

SEQUENCE LISTING

```
<160> NUMBER OF SEQ ID NOS: 50

<210> SEQ ID NO 1
<211> LENGTH: 475
<212> TYPE: PRT
<213> ORGANISM: Artificial Sequence
<220> FEATURE:
<223> OTHER INFORMATION: Amino acid sequence of anti-Her2 scFv-Fc

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys Gly Glu Pro Lys Ser Ser Asp Lys Thr His Thr Cys Pro Pro
                245                 250                 255
```

-continued

```
Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 2
<211> LENGTH: 1425
<212> TYPE: DNA
<213> ORGANISM: Artificial Sequence
<220> FEATURE:
<223> OTHER INFORMATION: Encoding DNA sequence of anti-Her2 scFv-Fc

<400> SEQUENCE: 2

```
gaggtgcagc tggtggagtc tggaggagga ctggtgcagc caggaggcag cctgcggctg      60

tcttgtgccg cttccggctt caacatcaag gacacctaca tccattgggt gaggcaggct     120

ccaggcaagg gactggagtg ggtggctcgg atctatccta ccaatggcta cacaagatat     180

gccgactccg tgaagggccg gtttaccatc agcgccgata cctctaagaa cacagcttac     240

ctgcagatga attccctgag ggccgaggac acagccgtgt actattgcag cagatgggga     300

ggcgacggct tctacgctat ggattattgg ggccagggca ccctggtgac agtgtccagc     360

ggcggcggcg gctctggagg aggaggatcc ggaggaggag gaagcgatat ccagatgacc     420

cagtcccctt cttccctgtc tgcctccgtg ggcgacagag tgaccatcac atgtcgcgct     480

agccaggatg tgaacacagc cgtggcttgg taccagcaga agccaggcaa ggcccccaag     540

ctgctgatct actccgcctc cttcctgtat tccggagtgc caagcaggtt ttccggaagc     600

cggtctggaa ccgacttcac cctgacaatc agctctctgc agcctgagga ttttgccaca     660

tactattgcc agcagcacta taccacaccc cctaccttcg gccagggcac aaaggtggag     720

atcaagggcg agccaaagtc cagcgacaag acccatacat gcccaccatg tcctgctcca     780

gagctgctgg gcggcccttc cgtgttcctg tttcctccaa agccaaagga taccctgatg     840
```

```
atctctagaa cccctgaggt gacatgcgtg gtggtggacg tgtcccacga ggatccagag    900

gtgaagttta actggtacgt ggacggcgtg gaggtgcata atgccaagac caagccaaga    960

gaggagcagt acaattctac ctatcgcgtg gtgtccgtgc tgacagtgct gcaccaggat   1020

tggctgaacg gcaaggagta taagtgcaag gtgagcaata aggccctgcc cgctcccatc   1080

gagaagacca tctctaaggc taagggccag cccagagagc ctcaggtgta cacactgccc   1140

cctagccgcg aggagatgac caagaaccag gtgtctctga catgtctggt gaagggcttt   1200

tatccatctg acatcgccgt ggagtgggag tccaatggcc agcccgagaa caattacaag   1260

accacaccac ccgtgctgga ctctgatggc tccttctttc tgtattccaa gctgaccgtg   1320

gataagagcc gctggcagca gggcaacgtg ttctcctgca gcgtgatgca tgaggctctg   1380

cacaatcatt acacacagaa gtctctgtcc ctgagccctg gcaag                   1425


<210> SEQ ID NO 3
<211> LENGTH: 475
<212> TYPE: PRT
<213> ORGANISM: Artificial Sequence
<220> FEATURE:
<223> OTHER INFORMATION: Amino acid sequence of anti-Her2-scFv-VL-F53Y-
      Fc

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Tyr Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys Gly Glu Pro Lys Ser Ser Asp Lys Thr His Thr Cys Pro Pro
                245                 250                 255
```

```
Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 4
<211> LENGTH: 1425
<212> TYPE: DNA
<213> ORGANISM: Artificial Sequence
<220> FEATURE:
<223> OTHER INFORMATION: Encoding DNA sequence of anti-Her2-scFv-VL-F53Y-Fc

<400> SEQUENCE: 4

```
gaggtgcagc tggtggagtc tggaggagga ctggtgcagc caggaggcag cctgcggctg     60

tcttgtgccg cttccggctt caacatcaag gacacctaca tccattgggt gaggcaggct    120

ccaggcaagg gactggagtg ggtggctcgg atctatccta ccaatggcta cacaagatat    180

gccgactccg tgaagggccg gtttaccatc agcgccgata cctctaagaa cacagcttac    240

ctgcagatga attccctgag ggccgaggac acagccgtgt actattgcag cagatgggga    300

ggcgacggct tctacgctat ggattattgg ggccagggca ccctggtgac agtgtccagc    360

ggcggcggcg gctctggagg aggaggatcc ggaggaggag gaagcgatat ccagatgacc    420

cagtcccctt cttccctgtc tgcctccgtg ggcgacagag tgaccatcac atgtcgcgct    480

agccaggatg tgaacacagc cgtggcttgg taccagcaga agccaggcaa ggcccccaag    540

ctgctgatct actccgcctc ctacctgtat tccggagtgc caagcaggtt ttccggaagc    600

cggtctggaa ccgacttcac cctgacaatc agctctctgc agcctgagga ttttgccaca    660

tactattgcc agcagcacta taccacaccc cctaccttcg gccagggcac aaaggtggag    720

atcaagggcg agccaaagtc cagcgacaag acccatacat gcccaccatg tcctgctcca    780
```

```
gagctgctgg gcggcccttc cgtgttcctg tttcctccaa agccaaagga taccctgatg    840

atctctagaa cccctgaggt gacatgcgtg gtggtggacg tgtcccacga ggatccagag    900

gtgaagttta actggtacgt ggacggcgtg gaggtgcata atgccaagac caagccaaga    960

gaggagcagt acaattctac ctatcgcgtg gtgtccgtgc tgacagtgct gcaccaggat   1020

tggctgaacg gcaaggagta taagtgcaag gtgagcaata aggccctgcc cgctcccatc   1080

gagaagacca tctctaaggc taagggccag cccagagagc ctcaggtgta cacactgccc   1140

cctagccgcg aggagatgac caagaaccag gtgtctctga catgtctggt gaagggcttt   1200

tatccatctg acatcgccgt ggagtgggag tccaatggcc agcccgagaa caattacaag   1260

accacaccac ccgtgctgga ctctgatggc tccttctttc tgtattccaa gctgaccgtg   1320

gataagagcc gctggcagca gggcaacgtg ttctcctgca gcgtgatgca tgaggctctg   1380

cacaatcatt acacacagaa gtctctgtcc ctgagccctg gcaag                   1425


<210> SEQ ID NO 5
<211> LENGTH: 475
<212> TYPE: PRT
<213> ORGANISM: Artificial Sequence
<220> FEATURE:
<223> OTHER INFORMATION: Amino acid sequence of anti-Her2-scFv-VL-F53A-
      Fc

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Ala Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240
```

-continued

```
Ile Lys Gly Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475


<210> SEQ ID NO 6
<211> LENGTH: 1425
<212> TYPE: DNA
<213> ORGANISM: Artificial Sequence
<220> FEATURE:
<223> OTHER INFORMATION: Encoding DNA sequence of anti-Her2-scFv-VL-
      F53A-Fc

<400> SEQUENCE: 6

gaggtgcagc tggtggagtc tggaggagga ctggtgcagc caggaggcag cctgcggctg      60

tcttgtgccg cttccggctt caacatcaag gacacctaca tccattgggt gaggcaggct     120

ccaggcaagg gactggagtg ggtggctcgg atctatccta ccaatggcta cacaagatat     180

gccgactccg tgaagggccg gtttaccatc agcgccgata cctctaagaa cacagcttac     240

ctgcagatga attccctgag ggccgaggac acagccgtgt actattgcag cagatgggga     300

ggcgacggct tctacgctat ggattattgg ggccagggca ccctggtgac agtgtccagc     360

ggcggcggcg gctctggagg aggaggatcc ggaggaggag gaagcgatat ccagatgacc     420

cagtcccctt cttccctgtc tgcctccgtg ggcgacagag tgaccatcac atgtcgcgct     480

agccaggatg tgaacacagc cgtggcttgg taccagcaga agccaggcaa ggcccccaag     540

ctgctgatct actccgcctc cgccctgtat tccggagtgc caagcaggtt ttccggaagc     600

cggtctggaa ccgacttcac cctgacaatc agctctctgc agcctgagga ttttgccaca     660

tactattgcc agcagcacta taccacaccc cctaccttcg gccagggcac aaaggtggag     720
```

```
atcaagggcg agccaaagtc cagcgacaag acccatacat gcccaccatg tcctgctcca    780

gagctgctgg gcggcccttc cgtgttcctg tttcctccaa agccaaagga taccctgatg    840

atctctagaa cccctgaggt gacatgcgtg gtggtggacg tgtcccacga ggatccagag    900

gtgaagttta actggtacgt ggacggcgtg gaggtgcata atgccaagac caagccaaga    960

gaggagcagt acaattctac ctatcgcgtg gtgtccgtgc tgacagtgct gcaccaggat   1020

tggctgaacg gcaaggagta taagtgcaag gtgagcaata aggccctgcc cgctcccatc   1080

gagaagacca tctctaaggc taagggccag cccagagagc ctcaggtgta cacactgccc   1140

cctagccgcg aggagatgac caagaaccag gtgtctctga catgtctggt gaagggcttt   1200

tatccatctg acatcgccgt ggagtgggag tccaatggcc agcccgagaa caattacaag   1260

accacaccac ccgtgctgga ctctgatggc tccttctttc tgtattccaa gctgaccgtg   1320

gataagagcc gctggcagca gggcaacgtg ttctcctgca gcgtgatgca tgaggctctg   1380

cacaatcatt acacacagaa gtctctgtcc ctgagccctg gcaag                  1425
```

```
<210> SEQ ID NO 7
<211> LENGTH: 475
<212> TYPE: PRT
<213> ORGANISM: Artificial Sequence
<220> FEATURE:
<223> OTHER INFORMATION: Amino acid sequence of anti-Her2-scFv-VL-F53R-
      Fc

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Arg Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
```

```
225                 230                 235                 240

Ile Lys Gly Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 8
<211> LENGTH: 1427
<212> TYPE: DNA
<213> ORGANISM: Artificial Sequence
<220> FEATURE:
<223> OTHER INFORMATION: Encoding DNA sequence of anti-Her2-scFv-VL-
F53R-Fc

<400> SEQUENCE: 8

```
gaggtgcagc tggtggagtc tggaggagga ctggtgcagc caggaggcag cctgcggctg      60

tcttgtgccg cttccggctt caacatcaag gacacctaca tccattgggt gaggcaggct     120

ccaggcaagg gactggagtg ggtggctcgg atctatccta ccaatggcta cacaagatat     180

gccgactccg tgaagggccg gtttaccatc agcgccgata cctctaagaa cacagcttac     240

ctgcagatga attccctgag ggccgaggac acagccgtgt actattgcag cagatgggga     300

ggcgacggct tctacgctat ggattattgg ggccagggca ccctggtgac agtgtccagc     360

ggcggcggcg gctctggagg aggaggatcc ggaggaggag gaagcgatat ccagatgacc     420

cagtcccctt cttccctgtc tgcctccgtg ggcgacagag tgaccatcac atgtcgcgct     480

agccaggatg tgaacacagc cgtggcttgg taccagcaga agccaggcaa ggcccccaag     540

ctgctgatct actccgcctc caggctgtat tccggagtgc caagcaggtt ttccggaagc     600

cggtctggaa ccgacttcac cctgacaatc agctctctgc agcctgagga ttttgccaca     660
```

-continued

```
tactattgcc agcagcacta taccacaccc cctaccttcg gccagggcac aaaggtggag    720

atcaagggcg agccaaagtc cagcgacaag acccatacat gcccaccatg tcctgctcca    780

gagctgctgg gcggcccttc cgtgttcctg tttcctccaa agccaaagga taccctgatg    840

atctctagaa cccctgaggt gacatgcgtg gtggtggacg tgtcccacga ggatccagag    900

gtgaagttta actggtacgt ggacggcgtg gaggtgcata atgccaagac caagccaaga    960

gaggagcagt acaattctac ctatcgcgtg gtgtccgtgc tgacagtgct gcaccaggat   1020

tggctgaacg gcaaggagta taagtgcaag gtgagcaata aggccctgcc cgctcccatc   1080

gagaagacca tctctaaggc taagggccag cccagagagc ctcaggtgta cacactgccc   1140

cctagccgcg aggagatgac caagaaccag gtgtctctga catgtctggt gaagggcttt   1200

tatccatctg acatcgccgt ggagtgggag tccaatggcc agcccgagaa caattacaag   1260

accacaccac ccgtgctgga ctctgatggc tccttctttc tgtattccaa gctgaccgtg   1320

gataagagcc gctggcagca gggcaacgtg ttctcctgca gcgtgatgca tgaggctctg   1380

cacaatcatt acacacagaa gtctctgtcc ctgagccctg gcaagta                1427


<210> SEQ ID NO 9
<211> LENGTH: 475
<212> TYPE: PRT
<213> ORGANISM: Artificial Sequence
<220> FEATURE:
<223> OTHER INFORMATION: Amino acid sequence of anti-Her2-scFv-VH-K30E-
      Fc

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Glu Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220
```

Gln His Tyr Thr Thr Pro Pro Thr Phe Gly Gln Gly Thr Lys Val Glu
225 230 235 240

Ile Lys Gly Glu Pro Lys Ser Ser Asp Lys Thr His Thr Cys Pro Pro
245 250 255

Cys Pro Ala Pro Glu Leu Leu Gly Gly Pro Ser Val Phe Leu Phe Pro
260 265 270

Pro Lys Pro Lys Asp Thr Leu Met Ile Ser Arg Thr Pro Glu Val Thr
275 280 285

Cys Val Val Val Asp Val Ser His Glu Asp Pro Glu Val Lys Phe Asn
290 295 300

Trp Tyr Val Asp Gly Val Glu Val His Asn Ala Lys Thr Lys Pro Arg
305 310 315 320

Glu Glu Gln Tyr Asn Ser Thr Tyr Arg Val Val Ser Val Leu Thr Val
325 330 335

Leu His Gln Asp Trp Leu Asn Gly Lys Glu Tyr Lys Cys Lys Val Ser
340 345 350

Asn Lys Ala Leu Pro Ala Pro Ile Glu Lys Thr Ile Ser Lys Ala Lys
355 360 365

Gly Gln Pro Arg Glu Pro Gln Val Tyr Thr Leu Pro Pro Ser Arg Glu
370 375 380

Glu Met Thr Lys Asn Gln Val Ser Leu Thr Cys Leu Val Lys Gly Phe
385 390 395 400

Tyr Pro Ser Asp Ile Ala Val Glu Trp Glu Ser Asn Gly Gln Pro Glu
405 410 415

Asn Asn Tyr Lys Thr Thr Pro Pro Val Leu Asp Ser Asp Gly Ser Phe
420 425 430

Phe Leu Tyr Ser Lys Leu Thr Val Asp Lys Ser Arg Trp Gln Gln Gly
435 440 445

Asn Val Phe Ser Cys Ser Val Met His Glu Ala Leu His Asn His Tyr
450 455 460

Thr Gln Lys Ser Leu Ser Leu Ser Pro Gly Lys
465 470 475

<210> SEQ ID NO 10
<211> LENGTH: 1425
<212> TYPE: DNA
<213> ORGANISM: Artificial Sequence
<220> FEATURE:
<223> OTHER INFORMATION: Encoding DNA sequence of anti-Her2-scFv-VH-K30E-Fc

<400> SEQUENCE: 10
gaggtgcagc tggtggagtc tggaggagga ctggtgcagc caggaggcag cctgcggctg 60
tcttgtgccg cttccggctt caacatcgag gacacctaca tccattgggt gaggcaggct 120
ccaggcaagg gactggagtg ggtggctcgg atctatccta ccaatggcta cacaagatat 180
gccgactccg tgaagggccg gtttaccatc agcgccgata cctctaagaa cacagcttac 240
ctgcagatga attccctgag ggccgaggac acagccgtgt actattgcag cagatgggga 300
ggcgacggct tctacgctat ggattattgg ggccagggca ccctggtgac agtgtccagc 360
ggcggcggcg gctctggagg aggaggatcc ggaggaggag gaagcgatat ccagatgacc 420
cagtcccctt cttccctgtc tgcctccgtg ggcgacagag tgaccatcac atgtcgcgct 480
agccaggatg tgaacacagc cgtggcttgg taccagcaga agccaggcaa ggcccccaag 540
ctgctgatct actccgcctc cttcctgtat tccggagtgc caagcaggtt ttccggaagc 600

```
cggtctggaa ccgacttcac cctgacaatc agctctctgc agcctgagga ttttgccaca    660

tactattgcc agcagcacta taccacaccc cctaccttcg gccagggcac aaaggtggag    720

atcaagggcg agccaaagtc cagcgacaag acccatacat gcccaccatg tcctgctcca    780

gagctgctgg gcggcccttc cgtgttcctg tttcctccaa agccaaagga taccctgatg    840

atctctagaa cccctgaggt gacatgcgtg gtggtggacg tgtcccacga ggatccagag    900

gtgaagttta actggtacgt ggacggcgtg gaggtgcata atgccaagac caagccaaga    960

gaggagcagt acaattctac ctatcgcgtg gtgtccgtgc tgacagtgct gcaccaggat   1020

tggctgaacg gcaaggagta taagtgcaag gtgagcaata aggccctgcc cgctcccatc   1080

gagaagacca tctctaaggc taagggccag cccagagagc ctcaggtgta cacactgccc   1140

cctagccgcg aggagatgac caagaaccag gtgtctctga catgtctggt gaagggcttt   1200

tatccatctg acatcgccgt ggagtgggag tccaatggcc agcccgagaa caattacaag   1260

accacaccac ccgtgctgga ctctgatggc tccttctttc tgtattccaa gctgaccgtg   1320

gataagagcc gctggcagca gggcaacgtg ttctcctgca gcgtgatgca tgaggctctg   1380

cacaatcatt acacacagaa gtctctgtcc ctgagccctg gcaag                   1425
```

<210> SEQ ID NO 11
<211> LENGTH: 480
<212> TYPE: PRT
<213> ORGANISM: Artificial Sequence
<220> FEATURE:
<223> OTHER INFORMATION: Amino acid sequence of anti-Her2-scFv-VH-K30E-VL-F53Y-Fc

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Glu Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Tyr Leu Tyr Ser Gly Val Pro Ser Arg Phe Ser Gly Ser Arg Ser Gly
        195                 200                 205
```

-continued

```
Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Gly Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Cys Arg Glu Glu Met Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480
```

<210> SEQ ID NO 12
<211> LENGTH: 1443
<212> TYPE: DNA
<213> ORGANISM: Artificial Sequence
<220> FEATURE:
<223> OTHER INFORMATION: Nucleotide sequence of anti-Her2-scFv-VH-K30E-VL-F53Y-Fc

<400> SEQUENCE: 12

```
gaggtgcaac tggtggaatc cggcggggga ctggtccaac ctggagggag cctgcggctg      60

tcttgcgccg cctctggctt caacatcgag gatacctaca tccactgggt gcggcaggcc     120

cctggcaagg gcctggaatg ggtcgctaga atctacccta ccaacggcta caccagatac     180

gccgactctg taaagggcag attcaccatc tctgccgata catctaagaa caccgcctac     240

ctgcagatga actccctgag agccgaggac accgccgtgt actactgctc ccggtggggc     300

ggtgacggct tttacgccat ggactactgg ggacaaggca cacttgttac ggtgtcctct     360

ggaggcggcg gctccggcgg cggcggctct ggcggaggcg gctctggcgg cggcggatct     420

gatatccaga tgacccagtc tcctagctcc ctctccgcct ccgtgggcga cagagtgaca     480

atcacctgca gagcttctca ggacgtgaac accgctgtgg cctggtacca gcagaagcct     540
```

```
ggcaaggccc ctaagctgct gatctactct gcttcctacc tgtactccgg cgtgcccagc    600

cggttctccg gctctcggtc cggcaccgac ttcactctga ccatctccag cctgcagcct    660

gaagatttcg ccacctacta ctgccagcag cactacacca cccctcccac cttcggccag    720

ggcaccaaag tggagatcaa gggcgagccc aagtcctccg ataaaaccca cacctgtcct    780

ccttgccctg cccctgaact actgggcggc ccttctgtgt tcctgttccc tcctaagccc    840

aaggacaccc tgatgatctc tagaacccct gaagtgacct gcgtggtggt ggatgtgtct    900

cacgaggacc ctgaggtcaa gttcaactgg tacgtggacg gcgtggaagt gcataacgcc    960

aagaccaagc ctagagaaga gcagtacaac tccacctaca gagtggtctc cgtgctgacc   1020

gtgctgcacc aggactggct gaacggcaaa gagtacaagt gcaaggtgtc caacaaggct   1080

ctgcctgctc ctatcgagaa gacaatctcc aaggccaaag gccagcctcg ggagcctcag   1140

gtgtacaccc tgcctccttg tagagaggaa atgaccaaga accaggtgtc tctgtggtgc   1200

ctggtgaagg gcttctaccc atccgacatc gccgtcgagt gggagtccaa cggacagccc   1260

gagaacaact acaagactac cccacctgtg ctggactccg atggctcctt cttcctgtac   1320

tccaagctga ccgtggacaa gtccagatgg cagcagggca acgtgttctc ctgctccgtg   1380

atgcacgagg ccctgcacaa ccactacacc cagaaatccc tgtctctgtc ccctggcaag   1440

tga                                                                  1443
```

```
<210> SEQ ID NO 13
<211> LENGTH: 449
<212> TYPE: PRT
<213> ORGANISM: Artificial Sequence
<220> FEATURE:
<223> OTHER INFORMATION: Amino acid sequence of anti-Her2-domain2-HC-Fc

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445

Lys
```

<210> SEQ ID NO 14
<211> LENGTH: 1350
<212> TYPE: DNA
<213> ORGANISM: Artificial Sequence
<220> FEATURE:
<223> OTHER INFORMATION: Nucleotide sequence ofanti-Her2-domain2-HC-Fc

<400> SEQUENCE: 14

```
gaagtgcagc tggttgaatc tggcggcgga ttggttcagc ctggcggatc tctgagactg      60

tcttgtgccg cctctggctt caccttcacc gactacacca tggactgggt ccgacaggct     120

cctggcaaag gactggaatg ggtcgccgac gtgaacccta attccggcgg ctccatctac     180

aaccagcggt tcaagggcag attcaccctg tccgtggacc ggtctaagaa caccctgtac     240

ctgcagatga actccctgag agccgaggac accgccgtgt actactgcgc cagaaacctg     300

ggaccttcct tctacttcga ctactggggc cagggcaccc tggtcacagt ttcttccgct     360

tccaccaagg gacccagcgt gttccctctg gctccttcca gcaagtctac ctctggcgga     420

acagctgctc tgggctgcct ggtcaaggac tactttcctg agcctgtgac cgtgtcctgg     480

aactctggcg ctctgacatc tggcgtgcac acctttccag ctgtgctgca gtcctccggc     540

ctgtactctc tgtcctctgt cgtgaccgtg ccttccagct ctctgggaac ccagacctac     600
```

```
atctgcaatg tgaaccacaa gccttccaac accaaggtgg acaagaaggt ggaacccaag    660

tcctgcgaca agacccacac ctgtcctcca tgtcctgctc cagaactgct cggcggacct    720

tccgtgttcc tgtttcctcc aaagcctaag gataccctga tgatctctcg gacccctgaa    780

gtgacctgcg tggtggtgga tgtgtctcac gaggatcccg aagtgaagtt caattggtac    840

gtggacggcg tggaagtgca caacgccaag accaagccta gagaggaaca gtacaactcc    900

acctacagag tggtgtccgt gctgaccgtg ctgcaccagg attggctgaa cggcaaagag    960

tacaagtgca aggtgtccaa caaggccctg cctgctccta tcgaaaagac catctccaag   1020

gccaagggcc agcctcggga acctcaagtc tgtaccctgc ctcctagccg ggaagagatg   1080

accaagaacc aggtgtccct gtcctgtgcc gtgaagggct tctacccttc cgatatcgcc   1140

gtggaatggg agagcaatgg ccagcctgag aacaactaca agacaacccc tcctgtgctg   1200

gactccgacg gctcattctt cctggtgtcc aagctgacag tggacaagtc cagatggcag   1260

cagggcaacg tgttctcctg ctccgtgatg cacgaggccc tgcacaacag gttcacccag   1320

aagtccctgt ctctgagccc cggcaaatga                                    1350
```

<210> SEQ ID NO 15
<211> LENGTH: 214
<212> TYPE: PRT
<213> ORGANISM: Artificial Sequence
<220> FEATURE:
<223> OTHER INFORMATION: Amino acid sequence of anti-Her2-domain2-LC

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 16
<211> LENGTH: 645
<212> TYPE: DNA
<213> ORGANISM: Artificial Sequence
<220> FEATURE:
<223> OTHER INFORMATION: Nucleotide sequence of anti-Her2-domain2-LC

<400> SEQUENCE: 16
gatatccaga tgacccagtc tccttccagc ctgtctgcct ctgtgggcga cagagtgacc 60
atcacatgca aggcctctca ggacgtgtcc atcggcgtgg catggtatca gcagaagcct 120
ggcaaggccc ctaagctgct gatctactcc gcctcctaca gatacacagg cgtgccctcc 180
agattctccg gctctggctc tggcacagac tttaccctga caatctccag cctgcagcct 240
gaggacttcg ccacctacta ctgccagcag tactacatct acccctacac cttcggccag 300
ggcaccaagg tggaaatcaa gagaaccgtg gccgctcctt ccgtgttcat cttcccacct 360
tccgacgagc agctgaagtc tggcaccgct tctgtcgtgt gcctgctgaa caacttctac 420
cctcgggaag ccaaggtgca gtggaaggtg gacaatgccc tgcagtccgg caactcccaa 480
gagtctgtga ccgagcagga ctccaaggac agcacctata gcctgtcctc cacactgacc 540
ctgtccaagg ccgactacga gaagcacaag gtgtacgcct gcgaagtgac ccatcagggc 600
ctgtctagtc ccgtgaccaa gtctttcaac cggggcgagt gttga 645

<210> SEQ ID NO 17
<211> LENGTH: 481
<212> TYPE: PRT
<213> ORGANISM: Artificial Sequence
<220> FEATURE:
<223> OTHER INFORMATION: Amino acid sequence of anti-Her2-scFv-VL-VH-Fc

<400> SEQUENCE: 17

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Gly Gly Ser Gly Gly
100 105 110

Gly Ser Gly Gly Gly Ser Gly Gly Gly Ser Gly Gly Gly Ser Gly Glu
115 120 125

Val Gln Leu Val Glu Ser Gly Gly Gly Leu Val Gln Pro Gly Gly Ser
130 135 140

Leu Arg Leu Ser Cys Ala Ala Ser Gly Phe Asn Ile Lys Asp Thr Tyr
145 150 155 160

Ile His Trp Val Arg Gln Ala Pro Gly Lys Gly Leu Glu Trp Val Ala
165 170 175

Arg Ile Tyr Pro Thr Asn Gly Tyr Thr Arg Tyr Ala Asp Ser Val Lys
180 185 190

Gly Arg Phe Thr Ile Ser Ala Asp Thr Ser Lys Asn Thr Ala Tyr Leu

-continued

```
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Ile
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Arg Tyr Met Thr Trp Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 18
<211> LENGTH: 1443
<212> TYPE: DNA
<213> ORGANISM: Artificial Sequence
<220> FEATURE:
<223> OTHER INFORMATION: Nucleotide sequence of anti-Her2-scFv-VL-VH-Fc

<400> SEQUENCE: 18

```
gatatccaga tgacccagtc cccttcctca ctgtctgcct ccgtgggaga cagagtgaca      60

atcacctgca gagcttccca ggatgtgaac accgcagtgg cctggtacca gcagaagcct     120

ggcaaggctc ctaagctgct gatctactct gcttccttcc tgtactccgg cgtcccttct     180

cggttctctg gctcccggtc tggcaccgac tttaccctga ccatctccag cctgcagcct     240

gaagacttcg ccacctacta ctgccagcag cactacacca ctccacccac cttcggtcag     300

ggcaccaagg tcgagatcaa gggcggctcc ggcgggggct ccggcggcgg ctctggcggc     360

ggaagcggag gcggaagtgg cgaagtgcaa ctggtcgagt ctggaggcgg cctggttcag     420
```

-continued

```
cctggcggaa gcctacggct gtcttgcgcc gcctctggct ttaacatcaa ggacacctac    480

atccactggg tgcggcaggc tcccggcaag ggcctggaat gggtggccag aatctaccct    540

accaatggct acaccagata cgccgattct gtgaaaggta gattcacaat ctccgccgac    600

acctccaaga ataccgccta cctgcagatg aactccctga gagccgagga tacagctgtc    660

tactactgtt ccagatgggg cggcgatggc ttctacgcca tggactactg gggccagggc    720

acactggtga ccgtgtcctc cgctgctgag cctaagtcct ccgacaaaac ccacacctgt    780

ccccccttgtc ctgctccaga actcctgggc ggcccttccg tgtttctgtt ccccccgaag    840

cctaaagata ccctgatgat ctctcgcacc ccagaagtga catgcgtggt agtcgacgtg    900

tctcatgagg accctgaggt gaagttcaac tggtatgtgg acggcgtgga agtgcacaac    960

gccaagacca agcctagaga agagcagtac aactctacct accgggtggt gtctgtgctg   1020

acagtgctgc accaggactg gctgaacggc aaagagtaca agtgcaaggt gtccaacaag   1080

gccctgcctg ctcccatcga gaagaccatt tctaaggcca agggacagcc cagagaacct   1140

caagtgtata ccctgcctcc tagccgggac gagctgacca agaaccaggt gtccctgatc   1200

tgcctggtga agggcttcta ccccagcgac atcgccgtgg agtgggagtc caacggccaa   1260

cctgagaacc ggtacatgac ctggcctcct gtgctggact ccgacggcag cttcttcctg   1320

tactctaagc tgaccgtgga caagagtaga tggcagcaag gcaacgtgtt ctcctgctcg   1380

gtgatgcacg aggctctgca taaccactac acccagaaat ccctgtcttt gagccctggc   1440

aag                                                                  1443
```

<210> SEQ ID NO 19
<211> LENGTH: 448
<212> TYPE: PRT
<213> ORGANISM: Artificial Sequence
<220> FEATURE:
<223> OTHER INFORMATION: Amino acid sequence of anti-Her2-domain2-HC-Fc-2

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
        435                 440                 445
```

<210> SEQ ID NO 20
<211> LENGTH: 1344
<212> TYPE: DNA
<213> ORGANISM: Artificial Sequence
<220> FEATURE:
<223> OTHER INFORMATION: Nucleotide sequence of anti-Her2-domain2-HC-Fc-2

<400> SEQUENCE: 20

```
gaggtgcagc tggtcgagtc tggaggaggt ctggtgcagc ctggaggctc tctgcggctg     60

tcctgtgccg cttctggctt caccttcacc gactacacca tggactgggt gcggcaggcc    120

cctggcaagg ggctggaatg ggtggccgac gtgaatccta actctggcgg ctccatctac    180

aaccagcggt tcaagggcag attcacactg tccgtggaca gatccaagaa caccctgtac    240

ctgcagatga acagcctgag agccgaggac accgctgtgt actactgcgc ccggaacctg    300

ggacccagct tctacttcga ctactggggc caaggcaccc tggtcaccgt gtccagcgcc    360

agcaccaaag gccctagtgt ctttcctctg gctcccagct ctaagtccac ctccggcggc    420

accgctgctc tgggctgtct ggtgaaggac tatttccctg agcctgtgac cgtctcttgg    480
```

-continued

```
aactccggcg ctctgacctc tggcgtgcat acctttcccg ccgtgctgca gtccagcggc    540

ctgtactctt tgtcttctgt cgtgacagtg ccttcttcct ctctcggcac acagacctac    600

atctgcaacg tgaaccacaa gccatctaac accaaagtgg acaagaaggt ggaacccaag    660

agctgcgaca aaacccacac ctgtccacct tgtcctgccc ctgagctgct gggcggacct    720

tccgtgttcc tgttcccccc taagcctaag gatacactga tgatctccag aacccccgag    780

gtgacctgcg tggtggtgga tgtttcccat gaagatcctg aagtgaagtt caactggtac    840

gtggacggcg tggaagtgca caacgccaag accaagccta gagaggaaca gtacaactct    900

acctacagag tggtttctgt gctcactgtg ctgcaccagg attggctgaa cggcaaagag    960

tacaagtgca aggtgtccaa caaggccctg cctgctccta tcgagaagac catcagcaag   1020

gctaagggcc agcctcgcga acctcaggtg tacgtgtatc ctccttcccg ggacgagctg   1080

accaagaacc aagtgtctct gacctgcctg gtgaaaggct tctacccctc cgacatcgcc   1140

gtggaatggg agtccaatgg ccagcccgag aacaactaca agaccacccc tccagtgctg   1200

gactccgatg gctccttcgc cctggtgtcc aagctgacag tagacaagtc tagatggcag   1260

cagggcaacg tgttctcctg ctccgtgatg cacgaggccc tgcacaatag attcacacag   1320

aagtccctgt ctctgtcccc tggc                                          1344
```

```
<210> SEQ ID NO 21
<211> LENGTH: 480
<212> TYPE: PRT
<213> ORGANISM: Artificial Sequence
<220> FEATURE:
<223> OTHER INFORMATION: Amino acid sequence of b-anti-Her2-scFv-VH-
      K30E-Fc

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Glu Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205
```

```
Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Gly Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Cys Arg Glu Glu Met Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480
```

<210> SEQ ID NO 22
<211> LENGTH: 1443
<212> TYPE: DNA
<213> ORGANISM: Artificial Sequence
<220> FEATURE:
<223> OTHER INFORMATION: Nucleotide sequence of b-anti-Her2-scFv-VH-K30E-Fc

<400> SEQUENCE: 22

```
gaggtgcaac tggtggaatc cggcggggga ctggtccaac ctggagggag cctgcggctg     60

tcttgcgccg cctctggctt caacatcgag gatacctaca tccactgggt gcggcaggcc    120

cctggcaagg gcctggaatg ggtcgctaga atctacccta ccaacggcta caccagatac    180

gccgactctg taaagggcag attcaccatc tctgccgata catctaagaa caccgcctac    240

ctgcagatga actccctgag agccgaggac accgccgtgt actactgctc ccggtggggc    300

ggtgacggct tttacgccat ggactactgg ggacaaggca cacttgttac ggtgtcctct    360

ggaggcggcg gctccggcgg cggcggctct ggcggaggcg gctctggcgg cggcggatct    420

gatatccaga tgacccagtc tcctagctcc ctctccgcct ccgtgggcga cagagtgaca    480
```

-continued

```
atcacctgca gagcttctca ggacgtgaac accgctgtgg cctggtacca gcagaagcct    540

ggcaaggccc ctaagctgct gatctactct gcttccttcc tgtactccgg cgtgcccagc    600

cggttctccg gctctcggtc cggcaccgac ttcactctga ccatctccag cctgcagcct    660

gaagatttcg ccacctacta ctgccagcag cactacacca cccctcccac cttcggccag    720

ggcaccaaag tggagatcaa gggcgagccc aagtcctccg ataaaaccca cacctgtcct    780

ccttgccctg cccctgaact actgggcggc ccttctgtgt tcctgttccc tcctaagccc    840

aaggacaccc tgatgatctc tagaacccct gaagtgacct gcgtggtggt ggatgtgtct    900

cacgaggacc ctgaggtcaa gttcaactgg tacgtggacg gcgtggaagt gcataacgcc    960

aagaccaagc ctagagaaga gcagtacaac tccacctaca gagtggtctc cgtgctgacc   1020

gtgctgcacc aggactggct gaacggcaaa gagtacaagt gcaaggtgtc caacaaggct   1080

ctgcctgctc ctatcgagaa gacaatctcc aaggccaaag gccagcctcg ggagcctcag   1140

gtgtacaccc tgcctccttg tagagaggaa atgaccaaga accaggtgtc tctgtggtgc   1200

ctggtgaagg gcttctaccc atccgacatc gccgtcgagt gggagtccaa cggacagccc   1260

gagaacaact acaagactac ccccacctgtg ctggactccg atggctcctt cttcctgtac   1320

tccaagctga ccgtggacaa gtccagatgg cagcagggca acgtgttctc ctgctccgtg   1380

atgcacgagg ccctgcacaa ccactacacc cagaaatccc tgtctctgtc ccctggcaag   1440

tga                                                                 1443


<210> SEQ ID NO 23
<211> LENGTH: 480
<212> TYPE: PRT
<213> ORGANISM: Artificial Sequence
<220> FEATURE:
<223> OTHER INFORMATION: Amino acid sequence of b-anti-Her2-scFv-VL-
      F53Y-Fc

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
```

-continued

```
            180                 185                 190

Tyr Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Gly Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Cys Arg Glu Glu Met Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480


<210> SEQ ID NO 24
<211> LENGTH: 1443
<212> TYPE: DNA
<213> ORGANISM: Artificial Sequence
<220> FEATURE:
<223> OTHER INFORMATION: Nucleotide sequence of b-anti-Her2-scFv-VL-
      F53Y-Fc

<400> SEQUENCE: 24

gaggtgcaac tggtggaatc cggcgggggga ctggtccaac ctggagggag cctgcggctg      60

tcttgcgccg cctctggctt caacatcaag gatacctaca tccactgggt gcggcaggcc     120

cctggcaagg gcctggaatg ggtcgctaga atctacccta ccaacggcta caccagatac     180

gccgactctg taaagggcag attcaccatc tctgccgata catctaagaa caccgcctac     240

ctgcagatga actccctgag agccgaggac accgccgtgt actactgctc ccggtggggc     300

ggtgacggct tttacgccat ggactactgg ggacaaggca cacttgttac ggtgtcctct     360
```

ggaggcggcg gctccggcgg cggcggctct ggcggaggcg gctctggcgg cggcggatct 420
gatatccaga tgacccagtc tcctagctcc ctctccgcct ccgtgggcga cagagtgaca 480
atcacctgca gagcttctca ggacgtgaac accgctgtgg cctggtacca gcagaagcct 540
ggcaaggccc ctaagctgct gatctactct gcttcctacc tgtactccgg cgtgcccagc 600
cggttctccg gctctcggtc cggcaccgac ttcactctga ccatctccag cctgcagcct 660
gaagatttcg ccacctacta ctgccagcag cactacacca cccctcccac cttcggccag 720
ggcaccaaag tggagatcaa gggcgagccc aagtcctccg ataaaaccca cacctgtcct 780
ccttgccctg cccctgaact actgggcggc ccttctgtgt tcctgttccc tcctaagccc 840
aaggacaccc tgatgatctc tagaacccct gaagtgacct gcgtggtggt ggatgtgtct 900
cacgaggacc ctgaggtcaa gttcaactgg tacgtggacg gcgtggaagt gcataacgcc 960
aagaccaagc ctagagaaga gcagtacaac tccacctaca gagtggtctc cgtgctgacc 1020
gtgctgcacc aggactggct gaacggcaaa gagtacaagt gcaaggtgtc caacaaggct 1080
ctgcctgctc ctatcgagaa gacaatctcc aaggccaaag gccagcctcg ggagcctcag 1140
gtgtacaccc tgcctccttg tagagaggaa atgaccaaga accaggtgtc tctgtggtgc 1200
ctggtgaagg gcttctaccc atccgacatc gccgtcgagt gggagtccaa cggacagccc 1260
gagaacaact acaagactac cccacctgtg ctggactccg atggctcctt cttcctgtac 1320
tccaagctga ccgtggacaa gtccagatgg cagcagggca acgtgttctc ctgctccgtg 1380
atgcacgagg ccctgcacaa ccactacacc cagaaatccc tgtctctgtc ccctggcaag 1440
tga 1443

<210> SEQ ID NO 25
<211> LENGTH: 480
<212> TYPE: PRT
<213> ORGANISM: Artificial Sequence
<220> FEATURE:
<223> OTHER INFORMATION: Amino acid sequence of anti-Her2-scFv-VH-VL-Fc

<400> SEQUENCE: 25

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Asp Ile Gln Met
130 135 140

Thr Gln Ser Pro Ser Ser Leu Ser Ala Ser Val Gly Asp Arg Val Thr
145 150 155 160

Ile Thr Cys Arg Ala Ser Gln Asp Val Asn Thr Ala Val Ala Trp Tyr

```
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Gly Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Cys Arg Glu Glu Met Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480
```

<210> SEQ ID NO 26
<211> LENGTH: 1440
<212> TYPE: DNA
<213> ORGANISM: Artificial Sequence
<220> FEATURE:
<223> OTHER INFORMATION: Nucleotide sequence of anti-Her2-scFv-VH-VL-Fc

<400> SEQUENCE: 26

```
gaggtgcaac tggtggaatc cggcggggga ctggtccaac ctggagggag cctgcggctg      60

tcttgcgccg cctctggctt caacatcaag gatacctaca tccactgggt gcggcaggcc     120

cctggcaagg gcctggaatg ggtcgctaga atctacccta ccaacggcta caccagatac     180

gccgactctg taaagggcag attcaccatc tctgccgata catctaagaa caccgcctac     240

ctgcagatga actccctgag agccgaggac accgccgtgt actactgctc ccggtggggc     300
```

-continued

```
ggtgacggct tttacgccat ggactactgg ggacaaggca cacttgttac ggtgtcctct    360

ggaggcggcg gctccggcgg cggcggctct ggcggaggcg gctctggcgg cggcggatct    420

gatatccaga tgacccagtc tcctagctcc ctctccgcct ccgtgggcga cagagtgaca    480

atcacctgca gagcttctca ggacgtgaac accgctgtgg cctggtacca gcagaagcct    540

ggcaaggccc ctaagctgct gatctactct gcttccttcc tgtactccgg cgtgcccagc    600

cggttctccg gctctcggtc cggcaccgac ttcactctga ccatctccag cctgcagcct    660

gaagatttcg ccacctacta ctgccagcag cactacacca cccctcccac cttcggccag    720

ggcaccaaag tggagatcaa gggcgagccc aagtcctccg ataaaaccca cacctgtcct    780

ccttgccctg cccctgaact actgggcggc ccttctgtgt tcctgttccc tcctaagccc    840

aaggacaccc tgatgatctc tagaacccct gaagtgacct gcgtggtggt ggatgtgtct    900

cacgaggacc ctgaggtcaa gttcaactgg tacgtggacg gcgtggaagt gcataacgcc    960

aagaccaagc ctagagaaga gcagtacaac tccacctaca gagtggtctc cgtgctgacc   1020

gtgctgcacc aggactggct gaacggcaaa gagtacaagt gcaaggtgtc caacaaggct   1080

ctgcctgctc ctatcgagaa gacaatctcc aaggccaaag gccagcctcg ggagcctcag   1140

gtgtacaccc tgcctccttg tagagaggaa atgaccaaga accaggtgtc tctgtggtgc   1200

ctggtgaagg gcttctaccc atccgacatc gccgtcgagt gggagtccaa cggacagccc   1260

gagaacaact acaagactac ccccacctgtg ctggactccg atggctcctt cttcctgtac   1320

tccaagctga ccgtggacaa gtccagatgg cagcagggca acgtgttctc ctgctccgtg   1380

atgcacgagg ccctgcacaa ccactacacc cagaaatccc tgtctctgtc ccctggcaag   1440
```

<210> SEQ ID NO 27
<211> LENGTH: 10
<212> TYPE: PRT
<213> ORGANISM: Artificial Sequence
<220> FEATURE:
<223> OTHER INFORMATION: synthetic polypeptide
<220> FEATURE:
<221> NAME/KEY: UNSURE
<222> LOCATION: (5)..(5)
<223> OTHER INFORMATION: Xaa is K or E

<400> SEQUENCE: 27

```
Gly Phe Asn Ile Xaa Asp Thr Tyr Ile His
1               5                   10
```

<210> SEQ ID NO 28
<211> LENGTH: 17
<212> TYPE: PRT
<213> ORGANISM: Mus musculus

<400> SEQUENCE: 28

```
Arg Ile Tyr Pro Thr Asn Gly Tyr Thr Arg Tyr Ala Asp Ser Val Lys
1               5                   10                  15

Gly
```

<210> SEQ ID NO 29
<211> LENGTH: 12
<212> TYPE: PRT
<213> ORGANISM: Mus musculus

<400> SEQUENCE: 29

```
Trp Gly Gly Asp Gly Phe Tyr Ala Met Asp Tyr Trp
1               5                   10
```

<210> SEQ ID NO 30
<211> LENGTH: 13
<212> TYPE: PRT
<213> ORGANISM: Mus musculus

<400> SEQUENCE: 30

Cys Arg Ala Ser Gln Asp Val Asn Thr Ala Val Ala Trp
1 5 10

<210> SEQ ID NO 31
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 31

Ser Ala Ser Tyr Leu Tyr Ser
1 5

<210> SEQ ID NO 32
<211> LENGTH: 9
<212> TYPE: PRT
<213> ORGANISM: Mus musculus

<400> SEQUENCE: 32

Gln Gln His Tyr Thr Thr Pro Pro Thr
1 5

<210> SEQ ID NO 33
<211> LENGTH: 7
<212> TYPE: PRT
<213> ORGANISM: Mus musculus

<400> SEQUENCE: 33

Ser Ala Ser Phe Leu Tyr Ser
1 5

<210> SEQ ID NO 34
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: UNSURE
<222> LOCATION: (4)..(4)
<223> OTHER INFORMATION: Xaa is F or Y

<400> SEQUENCE: 34

Ser Ala Ser Xaa Leu Tyr Ser
1 5

<210> SEQ ID NO 35
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 35

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Glu Asp Thr
20 25 30

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 36
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 37
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110
```

```
Thr Leu Val Thr Val Ser Ser
        115


<210> SEQ ID NO 38
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105


<210> SEQ ID NO 39
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 40
<211> LENGTH: 120
<212> TYPE: PRT
<213> ORGANISM: Artificial Sequence
<220> FEATURE:
<223> OTHER INFORMATION: synthetic polypeptide

<400> SEQUENCE: 40

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 41
<211> LENGTH: 120
<212> TYPE: PRT
<213> ORGANISM: Artificial Sequence
<220> FEATURE:
<223> OTHER INFORMATION: synthetic polypeptide
<220> FEATURE:
<221> NAME/KEY: UNSURE
<222> LOCATION: (30)..(30)
<223> OTHER INFORMATION: Xaa is K or E

<400> SEQUENCE: 41

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Xaa Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 42
<211> LENGTH: 107
<212> TYPE: PRT
<213> ORGANISM: Artificial Sequence
<220> FEATURE:
<223> OTHER INFORMATION: synthetic polypeptide
<220> FEATURE:
<221> NAME/KEY: UNSURE
<222> LOCATION: (53)..(53)
<223> OTHER INFORMATION: Xaa is F or Y

<400> SEQUENCE: 42

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

-continued

```
Val Ala Trp Tyr Gln Gln Lys Pro Gly Lys Ala Pro Lys Leu Leu Ile
        35                  40                  45

Tyr Ser Ala Ser Xaa Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 43
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 43

Gly Phe Asn Ile Glu Asp Thr Tyr Ile His
1               5                   10


<210> SEQ ID NO 44
<211> LENGTH: 10
<212> TYPE: PRT
<213> ORGANISM: Mus musculus

<400> SEQUENCE: 44

Gly Phe Asn Ile Lys Asp Thr Tyr Ile His
1               5                   10


<210> SEQ ID NO 45
<211> LENGTH: 10
<212> TYPE: PRT
<213> ORGANISM: Mus musculus

<400> SEQUENCE: 45

Gly Phe Thr Phe Thr Asp Tyr Thr Met Asp
1               5                   10


<210> SEQ ID NO 46
<211> LENGTH: 17
<212> TYPE: PRT
<213> ORGANISM: Mus musculus

<400> SEQUENCE: 46

Asp Val Asn Pro Asn Ser Gly Gly Ser Ile Tyr Asn Gln Arg Phe Lys
1               5                   10                  15

Gly


<210> SEQ ID NO 47
<211> LENGTH: 10
<212> TYPE: PRT
<213> ORGANISM: Mus musculus

<400> SEQUENCE: 47

Asn Leu Gly Pro Ser Phe Tyr Phe Asp Tyr
1               5                   10


<210> SEQ ID NO 48
<211> LENGTH: 11
<212> TYPE: PRT
<213> ORGANISM: Mus musculus
```

-continued

```
<400> SEQUENCE: 48

Lys Ala Ser Gln Asp Val Ser Ile Gly Val Ala
1               5                   10


<210> SEQ ID NO 49
<211> LENGTH: 7
<212> TYPE: PRT
<213> ORGANISM: Mus musculus

<400> SEQUENCE: 49

Ser Ala Ser Tyr Arg Tyr Thr
1               5


<210> SEQ ID NO 50
<211> LENGTH: 9
<212> TYPE: PRT
<213> ORGANISM: Mus musculus

<400> SEQUENCE: 50

Gln Gln Tyr Tyr Ile Tyr Pro Tyr Thr
1               5
```